US012655173B2

(12) United States Patent
Burke et al.

(10) Patent No.: US 12,655,173 B2
(45) Date of Patent: Jun. 16, 2026

(54) HYBRID AMIDE DERIVATIVES OF AMPHOTERICIN B

(71) Applicant: The Board of Trustees of the University of Illinois, Urbana, IL (US)

(72) Inventors: Martin D. Burke, Champaign, IL (US); Arun Maji, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 518 days.

(21) Appl. No.: 18/020,119

(22) PCT Filed: Aug. 9, 2021

(86) PCT No.: PCT/US2021/045205

§ 371 (c)(1),
(2) Date: Feb. 7, 2023

(87) PCT Pub. No.: WO2022/035752

PCT Pub. Date: Feb. 17, 2022

(65) Prior Publication Data

US 2023/0357303 A1 Nov. 9, 2023

Related U.S. Application Data

(60) Provisional application No. 63/175,771, filed on Apr. 16, 2021, provisional application No. 63/063,655, filed on Aug. 10, 2020.

(51) Int. Cl.

*C07H 17/08* (2006.01)
*A61P 31/10* (2006.01)

(52) U.S. Cl.

CPC .............. *C07H 17/08* (2013.01); *A61P 31/10* (2018.01)

(58) Field of Classification Search

CPC ............................ C07H 17/08; A61K 31/7048
See application file for complete search history.

(56) References Cited

U.S. PATENT DOCUMENTS

| | | | | |
|---|---|---|---|---|
| 4,783,527 | A * | 11/1988 | Falkowski | A61P 31/04 536/6.5 |
| 9,738,677 | B2 | 8/2017 | Burke et al. | |
| 10,323,057 | B2 | 6/2019 | Burke et al. | |
| 11,028,114 | B2 | 6/2021 | Burke et al. | |
| 11,117,920 | B2 | 9/2021 | Burke et al. | |
| 11,970,512 | B2 | 4/2024 | Burke et al. | |
| 2003/0040493 | A1 | 2/2003 | Chang et al. | |
| 2016/0215012 | A1 | 7/2016 | Burke et al. | |
| 2016/0304548 | A1 | 10/2016 | Burke et al. | |
| 2017/0088572 | A1 | 3/2017 | Burke et al. | |
| 2019/0135847 | A1 | 5/2019 | Miyazaki et al. | |
| 2019/0345187 | A1 | 11/2019 | Burke et al. | |
| 2020/0002368 | A1 | 1/2020 | Burke et al. | |
| 2022/0056066 | A1 | 2/2022 | Burke et al. | |
| 2023/0016424 | A1 | 1/2023 | Burke et al. | |
| 2023/0357303 | A1 | 11/2023 | Burke et al. | |

FOREIGN PATENT DOCUMENTS

| | | | |
|---|---|---|---|
| WO | WO-2015/175875 | A1 | 11/2015 |
| WO | WO-2020/051465 | A1 | 3/2020 |
| WO | WO-2021/026250 | A1 | 2/2021 |
| WO | WO-2021/026520 | A1 | 2/2021 |
| WO | WO-2022/035752 | A1 | 2/2022 |

OTHER PUBLICATIONS

Supplementary European Search Report for EP Application No. 21856507.5 dated Nov. 5, 2024.
International Search Report and Written Opinion for International Application No. PCT/US21/45205 mailed Nov. 17, 2021.
PubChem CID 130198287 (9 pages) Modified Oct. 16, 2021.
Tevyashova et al., "Structure-antifungal activity relationships of polyene antibiotics of the amphotericin B group." Antimicrobial Agents and Chemotherapy 57.8 (2013): 3815-3822.

* cited by examiner

*Primary Examiner* — Layla D Berry

(74) *Attorney, Agent, or Firm* — Foley Hoag LLP; Dana M. Gordon; Laura A. Wzorek

(57) ABSTRACT

Disclosed are C16 amide derivatives of C2'-epi-amphotericin B (C2'epiAmB) and salts thereof, characterized by improved clinical efficacy with reduced toxicity compared to AmB. Also disclosed are pharmaceutical compositions, comprising any of the disclosed compounds or salts thereof, as well as methods of treatment and therapeutic uses of the same.

13 Claims, 38 Drawing Sheets

| PK Parameters | 1 mg/kg | 5 mg/kg |
|---|---|---|
| $T_{1/2}$(h) | 8.37 | 9.60 |
| Cl (mL/min/kg) | 0.891 | 1.05 |
| $AUC_{0\text{-}inf}$ (ng·h/mL) | 18785 | 79575 |

*Chromatogram Peaks*

| Peak | Start | RT | End | Height | Area | Area % | SNR |
|---|---|---|---|---|---|---|---|
| 1 | 1.601 | 1.616 | 1.629 | 12 | 13 | 1.22 | |
| 2 | 1.821 | 1.873 | 1.895 | 6 | 15 | 1.49 | |
| 3 | 5.643 | 5.719 | 5.855 | 322 | 1029 | 100.00 | |

HYBRID AMIDE DERIVATIVES OF AMPHOTERICIN B

CROSS REFERENCE TO RELATED APPLICATIONS

This application is a 371 National Stage Application of International Application No. PCT/US2021/045205, filed Aug. 9, 2021; which claims the benefit of priority to U.S. Provisional Patent Application No. 63/063,655, filed Aug. 10, 2020; and U.S. Provisional Patent Application No. 63/175,771, filed Apr. 16, 2021.

GOVERNMENT SUPPORT

This invention was made with government support under grant AI135812 awarded by the National Institutes of Health. The government has certain rights in the invention.

BACKGROUND OF THE INVENTION

Morbidity and mortality from invasive fungal infections are significant, and largely caused by two genera of fungal pathogens: *Candida* and *Aspergillus. Candida* species are the 4th most common pathogen isolated in all bloodstream infections. Treatment for invasive candidiasis has a limited (50-70%) success rate, and this is typically only in the healthiest patients. Attributable mortality for invasive candidiasis is substantial (20-30%). The incidence of invasive aspergillosis due to *A. fumigatus* has increased three-fold in the last decade and its mortality has risen by over 300%. Moreover, current therapy for invasive aspergillosis has a lower 40-50% treatment success rate. Invasive aspergillosis is consistently a leading killer in immunocompromised patients. Moreover, invasive mold infections (fusariosis, scedosporosis, and mucromycosis) have even higher mortality rates and no effective therapeutic options. The current guideline-recommended first line therapeutic for invasive aspergillosis, as well as most other invasive mold infections, is the triazole antifungal voriconazole. However, pan-triazole resistance in *Aspergillus* is as high as 30% in some locations and amongst certain high-risk patient groups. Recognizing this lack of effective treatments, the *Infectious Diseases Society of America* highlighted *A. fumigatus* as one of only six pathogens where a "substantive breakthrough is urgently needed."

Amphotericin B (AmB) is an exceptionally promising starting point, because this drug has potent and dose-dependent fungicidal activity against a broad range of fungal pathogens and has evaded resistance for over half a century The fungicidal, as opposed to fungistatic, activity of AmB is essential in immunocompromised patients which lack a robust immune system to help clear an infection. Broad antifungal activity is especially important in critically ill patients when the identity of the pathogen is unknown and immediate empirical therapy is required. An international expert panel recently mandated that novel therapeutic approaches centered around AmB, with no resistance issues, are required. The problem is that AmB is exceptionally toxic, which limits its use to low-dose protocols that often fail to eradicate disease.

A new, paradigm-shifting mechanistic understanding of AmB that evaded the field for half a century was achieved. Previous studies report AmB binding to sterols, which was thought primarily to drive formation of membrane-permeabilizing pores to kill both fungal and human cells. After 10 years of intensive synthesis-enabled atomistic interrogations of this natural product and frontier SSNMR experiments, it is alternatively discovered that AmB primarily kills both fungal and human cells by forming a cytocidal extramembranous sterol sponge. This large aggregate sits on the surface of lipid bilayers and rapidly extracts membrane sterols, which leads to cell death. Membrane permeabilization is not required. Based on this new mechanism and increasingly refined structural information, it is proposed that a small molecule-based ligand-selective allosteric effect could enable selective binding of ergosterol over cholesterol. Guided by this model, the elimination of cholesterol binding and thus mammalian toxicity in the form of a new derivative, C2'epiAmB, was achieved.

A limitation with C2'epiAmB, however, is a relative lack of potency against a number of clinically relevant yeast and molds. An AmB derivative that retains potent, broad spectrum, and resistance-evasive fungicidal activity but lacks dose-limiting toxicities would enable a new high dose treatment paradigm with improved clinical efficacy.

SUMMARY OF THE INVENTION

In certain aspects, provided herein is a compound selected from the group consisting

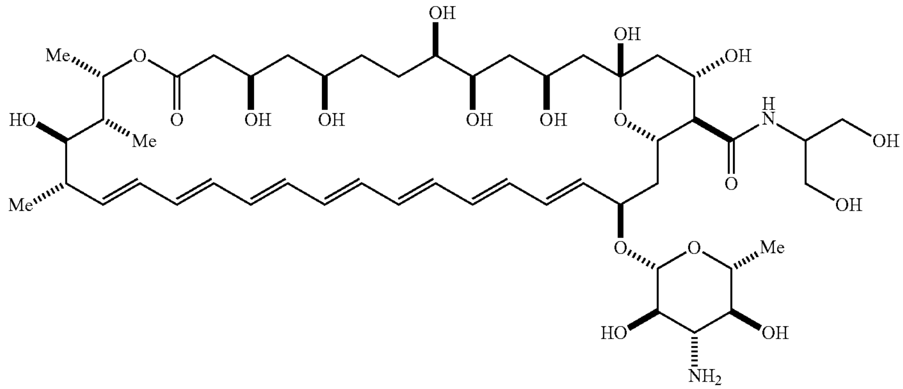

and

-continued

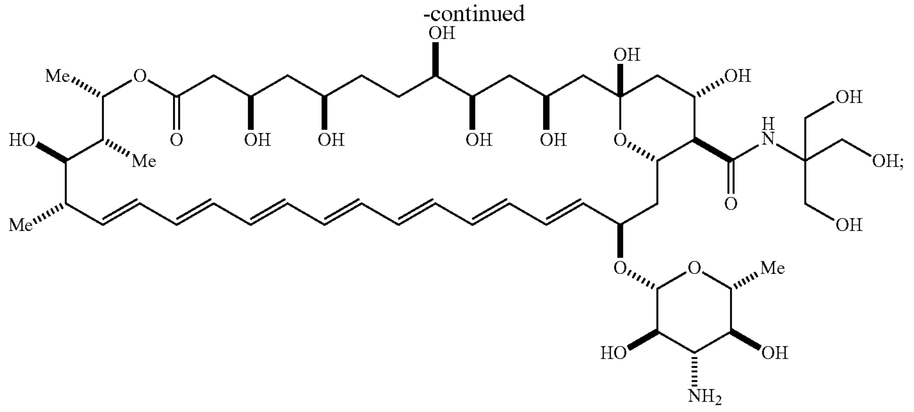

or a pharmaceutically acceptable salt thereof.

In other aspects, provided herein are pharmaceutical compositions comprising one of the disclosed compounds, or a pharmaceutically acceptable salt thereof; and a pharmaceutically acceptable carrier.

In yet other aspects, provided herein are methods of treating fungal infections, the methods comprising administering to a subject in need thereof a therapeutically effective amount of a disclosed compound or a pharmaceutically acceptable salt thereof, thereby treating the fungal infections.

In still other aspects, provided herein is use of a disclosed compound or a pharmaceutically acceptable salt thereof in the manufacture of a medicament for the treatment of a fungal infection.

In certain aspects, provided herein are compounds and pharmaceutical compositions for use as medicaments, and for use in treating fungal infections.

BRIEF DESCRIPTION OF THE FIGURES

FIG. 20A: Neurotoxicity; FIG. 20B: Hepatotoxicity; FIG. 20C: Cardiotoxicity; and FIG. 20D: Hemotoxicity.

DETAILED DESCRIPTION OF THE INVENTION

Figure 1A:
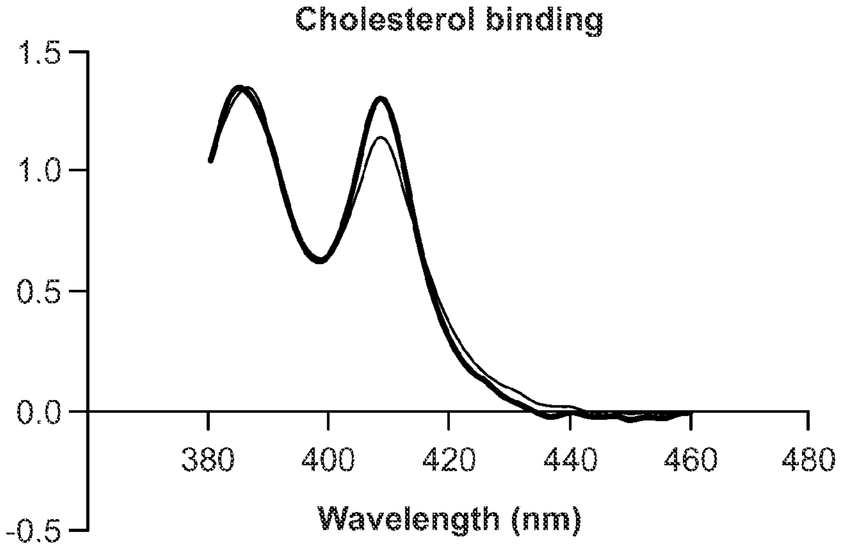
FIGS. 1A-1B depict the results of in vitro safety studies using Compound 1.

Amphotericin B (AmB) is a polyene macrolide with a mycosamine appendage, the compound having the following structure:

The present invention relates, at least in part, to the discovery by the inventors of further derivatives of AmB which also are characterized by improved therapeutic index compared to AmB. The various derivatives, i.e., compounds of the invention, can be semi-synthetic or fully synthetic. An aspect of the invention is the development of a new synthetic derivative of AmB that retains potent binding of ergosterol but shows no detectable binding of cholesterol. This derivative retains fungicidal potency against many yeasts and molds but shows no detectable mammalian toxicity. This demonstrates that differential binding of ergosterol over cholesterol is possible and provides a non-toxic variant of AmB that preserves desirable antifungal properties. Compounds of the invention enable a new high-dose treatment strategy to eradicate life-threatening invasive fungal infections with a significantly improved safety profile.

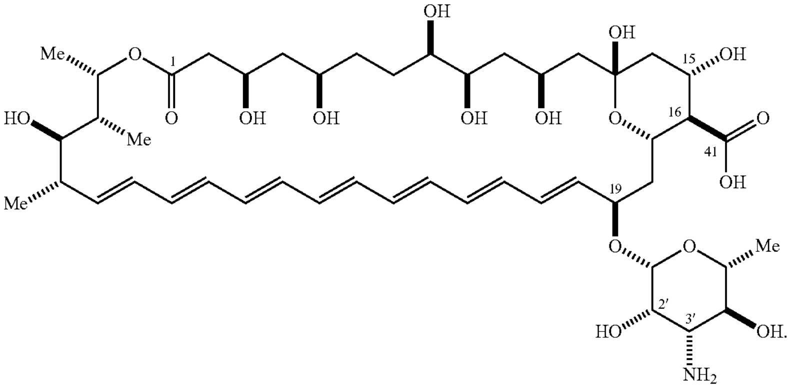

Amphotericin B

AmB is generally obtained from a strain of *Streptomyces nodosus*. It is currently approved for clinical use in the United States for the treatment of progressive, potentially life-threatening fungal infections, including such infections as systemic or deep tissue candidiasis, aspergillosis, cryptococcosis, blastomycosis, coccidioidomycosis, histoplasmosis, and mucormycosis, among others. It is generally formulated for intravenous injection. Amphotericin B is commercially available, for example, as Fungizone® (Squibb), Amphocin® (Pfizer), Abelcet® (Enzon), and Ambisome® (Astellas). Due to its undesirable toxic side effects, dosing is generally limited to a maximum of about 1.0 mg/kg/day and total cumulative doses not to exceed about 3 g in humans.

AmB kills both fungal and human cells by forming a cytocidal extramembranous sterol sponge. Anderson, T. M. et al., *Nat Chem Biol* 2014, 10 (5), 400-6. This large aggregate sits on the surface of lipid bilayers and rapidly extracts membrane sterols, which leads to cell death. Membrane permeabilization is not required. Based on this mechanism, a small molecule-based ligand-selective allosteric effect would enable selective binding of ergosterol over cholesterol and would eliminate the mammalian toxicity of AmB (in the form of C2'epiAmB). See Wilcock, B. C. et al., *J Am Chem Soc* 2013, 135 (23), 8488-91. The present invention discloses the $K_{DS}$ for the binding of both ergosterol and cholesterol to the AmB sterol sponge, which provides a quantitative and mechanistically-grounded biophysical parameter to guide rational optimization of the therapeutic index of this clinically significant natural product.

Compounds of the invention and pharmaceutical compositions of the invention are useful for inhibiting the growth of a fungus. In one embodiment, an effective amount of a compound of the invention is contacted with a fungus, thereby inhibiting growth of the fungus. In one embodiment, a compound of the invention, or a pharmaceutically acceptable salt thereof, is added to or included in tissue culture medium.

Compounds of the invention and pharmaceutical compositions of the invention are useful for the treatment of fungal infections in a subject. In one embodiment, a therapeutically effective amount of a compound of the invention, or a pharmaceutically acceptable salt thereof, is administered to a subject in need thereof, thereby treating the fungal infection.

Yeasts are eukaryotic organisms classified in the kingdom Fungi. Fungi include yeasts, molds, and larger organisms including mushrooms. Yeasts and molds are of clinical relevance as infections agents. Yeasts are typically described as budding forms of fungi. Of particular importance in connection with the invention are species of yeast that can cause infections in mammalian hosts. Such infections most commonly occur in immunocompromised hosts, including hosts with compromised barriers to infection (e.g. burn victims) and hosts with compromised immune systems (e.g., hosts receiving chemotherapy or immune suppressive therapy, and hosts infected with HIV). Pathogenic yeasts include, without limitation, various species of the genus *Candida*, as well as of *Cryptococcus*. Of particular note among pathogenic yeasts of the genus *Candida* are *C.*

*albicans, C. tropicalis, C. stellatoidea, C. glabrata, C. krusei, C. parapsilosis, C. guilliermondii, C. viswanathii*, and *C. lusitaniae*. The genus *Cryptococcus* specifically includes *Cryptococcus neoformans*. Yeast can cause infections of mucosal membranes, for example oral, esophageal, and vaginal infections in humans, as well as infections of bone, blood, urogenital tract, and central nervous system. This list is exemplary and is not limiting in any way.

A number of fungi (apart from yeast) can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic fungi (apart from yeast) include, without limitation, species of *Aspergillus. Rhizopus, Mucor, Histoplasma, Coccidioides, Blastomyces, Trichophyton, Microsporum*, and *Epidermophyton*. Of particular note among the foregoing are *A. fumigatus, A. flavus, A. niger, H. capsulatum, C. immitis*, and *B. dermatitidis*. Fungi can cause systemic and deep tissue infections in lung, bone, blood, urogenital tract, and central nervous system, to name a few. Some fungi are responsible for infections of the skin and nails.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito. 1999; Smith and March, March's Advanced Organic Chemistry, 5$^{th}$ Edition, John Wiley & amp; Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPFC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, NY 1962); and Wilen, Tables of Resolving Agents and Optical Resolutions p. 268 (E. F. Eliel, Ed., Univ. of Notre Dame Press, Notre Dame, IN 1972).

The invention additionally encompasses compounds described herein as individual isomers substantially free of other isomers, and alternatively, as mixtures of various isomers.

The following terms are intended to have the meanings presented therewith below and are useful in understanding the description and intended scope of the present invention.

When describing; the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine. N-methylglucamine and the like. Salts further include, by way of example only, sodium potassium, calcium, magnesium, ammonium, tetraalkylammonium, and the like; and when the compound contains a basic functionality, salts of nontoxic organic or inorganic acids, such as hydrochloride, hydrobromide, tartrate, mesylate, acetate, maleate, oxalate and the like.

"Pharmaceutically acceptable cation" refers to an acceptable cationic counterion of an acidic functional group. Such cations are exemplified by sodium, potassium, calcium, magnesium, ammonium, tetraalkylammonium cations, and the like (see, e. g., Berge, et al, *J. Pharm. Sci.* 66 (1):1-79 (January 77).

"Pharmaceutically acceptable vehicle" refers to a diluent, adjuvant, excipient or carrier with which a compound of the invention is administered.

A "subject" to which administration is contemplated includes, but is not limited to, humans (i.e., a male or female of any age group, e.g., a pediatric subject (e.g, infant, child, adolescent) or adult subject (e.g., young adult, middle aged adult or senior adult) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

An "effective amount" means the amount of a compound that, when administered to a subject for treating or preventing a disease, is sufficient to effect such treatment or prevention. The "effective amount" can vary, depending on the compound, the disease and its severity, and the age, weight, etc., of the subject to be treated. A "therapeutically effective amount" refers to the effective amount for therapeutic treatment. A "prophylactically effective amount" refers to the effective amount for prophylactic treatment.

"Preventing" or "prevention" or "prophylactic treatment" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

"Prophylaxis" is related to "prevention," and refers to a measure or procedure the purpose of which is to prevent, rather than to treat or cure a disease. Non limiting examples of prophylactic measures may include the administration of vaccines; the administration of low molecular weight heparin to hospital patients at risk for thrombosis due, for example, to immobilization, and the administration of an anti-malarial agent such as chloroquine, in advance of a visit to a geographical region where malaria is endemic or the risk of contracting malaria is high.

"Treating" or "treatment" or "therapeutic treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^{2}H$ or D), carbon-13 ($^{13}C$) nitrogen-15 ($^{15}N$), or the like. It will be understood that, in a compound where such isotopic substitution is made, the following atoms, where present, may vary, so that for example, any hydrogen may be "$^{2}H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radio-active isotopes tritium, i.e., $^{3}H$, and carbon-14, i.e., $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope of the invention.

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 95% by weight R-compound and at most about 5% by weight S-compound, at least about 99% by weight R-compound and at most about 1% by weight S-compound, or at least about 99.9% by weight R-compound and at most about 0.1% by weight S-compound. In certain embodiments, the weights are based upon total weight of compound.

As used herein and unless otherwise indicated, the term "enantiomerically pure S-compound" or "S-compound" refers to at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight k-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compounds of the Invention
In certain aspects, provided herein is a compound selected from the group consisting of:
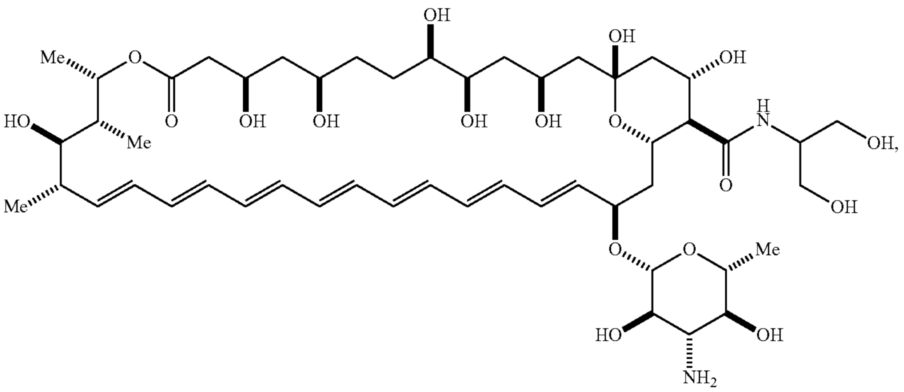
and
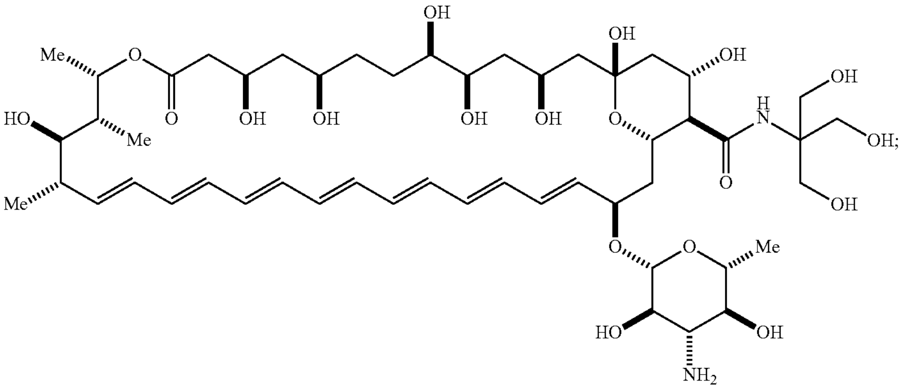
or a pharmaceutically acceptable salt thereof.
In certain embodiments, the compound is:
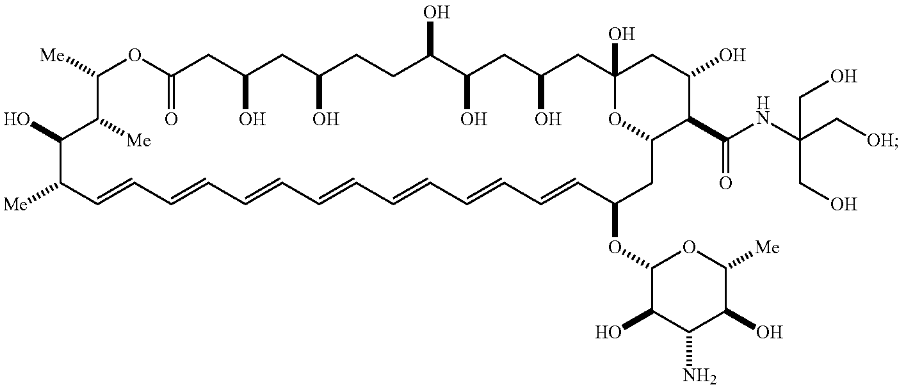
or a pharmaceutically acceptable salt thereof.

In other embodiments, the compound is:
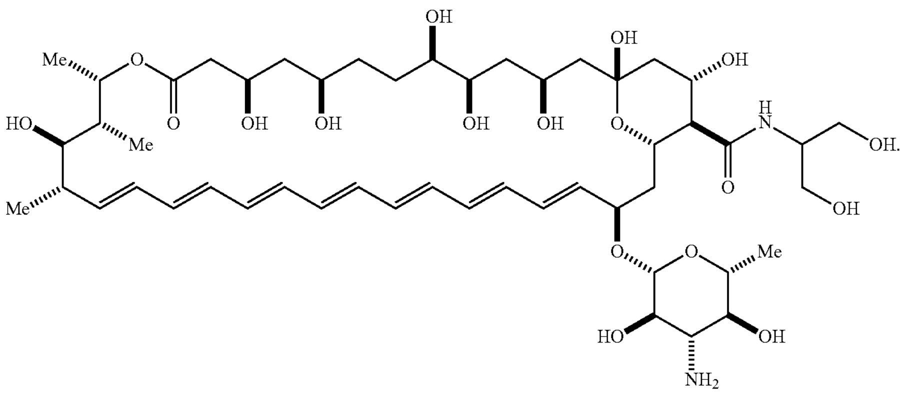
In further embodiments, the compound is:
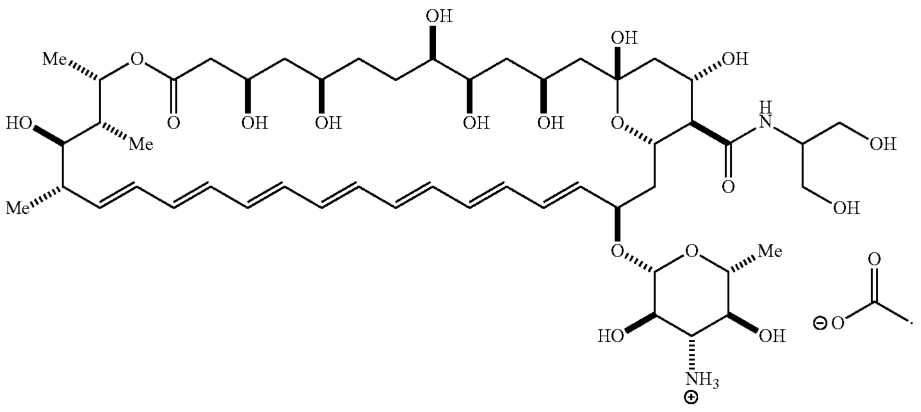
In yet other embodiments, the compound is:
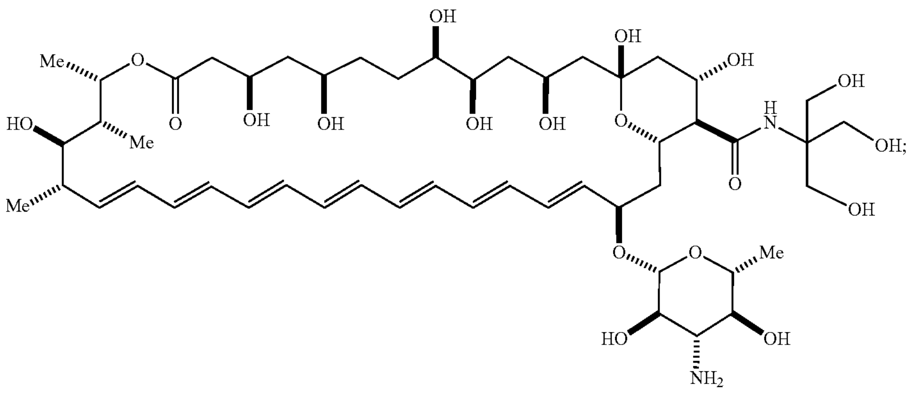
or a pharmaceutically acceptable salt thereof.

In still other embodiments, the compound is:

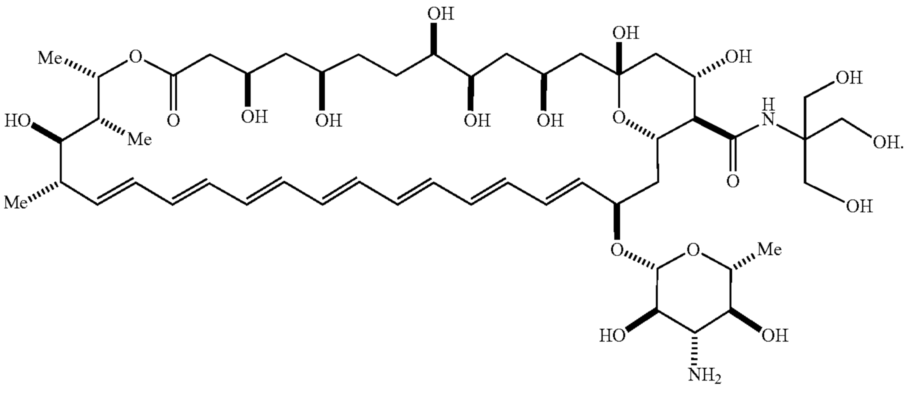

In further embodiments, the compound is:

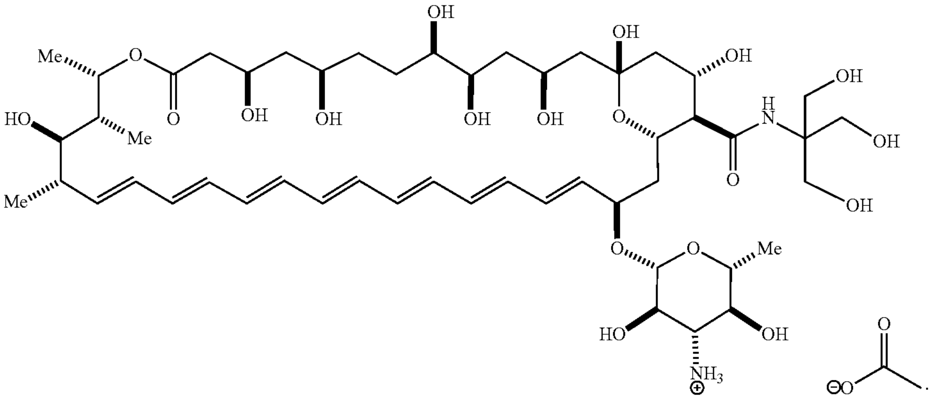

In other aspects, provided herein are pharmaceutical compositions comprising a disclosed compound, or a pharmaceutically acceptable salt thereof; and a pharmaceutically acceptable carrier. In certain embodiments, the pharmaceutical composition is an intravenous dosage form. In other embodiments, the pharmaceutical composition is an oral dosage form.

In yet other aspects, provided herein is a method of treating a fungal infection, the method comprising administering to a subject in need thereof a therapeutically effective amount of a disclosed compound or a pharmaceutically acceptable salt thereof, thereby treating the fungal infection. In certain embodiments, the compound is administered intravenously. In other embodiments, the compound is administered orally.

In still other aspects, provided herein is use of a disclosed compound or a pharmaceutically acceptable thereof in the manufacture of a medicament for the treatment of a fungal infection.

In certain aspects, provided herein are compounds and pharmaceutically acceptable salts thereof for use as medicaments, and for use in treating fungal infections.

Pharmaceutical Compositions

The invention also provides pharmaceutical compositions of a disclosed compound or salt thereof, and methods for preparing such compositions.

An aspect of the invention is a pharmaceutical composition comprising a compound of the invention; and a pharmaceutically acceptable carrier. In certain embodiments, the invention is a pharmaceutical composition, comprising a compound of the invention, or a pharmaceutically acceptable salt thereof, and a pharmaceutically acceptable carrier. The term "pharmaceutically acceptable carrier" means one or more compatible solid or liquid filler, diluent, or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficacy.

In certain embodiments, the pharmaceutical composition is an intravenous dosage form.

In certain embodiments, the pharmaceutical composition is an oral dosage form.

In certain embodiments, the pharmaceutical composition is a lyophilized preparation of a liposome-intercalated or liposome-encapsulated active compound.

In certain embodiments, the pharmaceutical composition is a lipid complex of the compound in aqueous suspension.

The foregoing embodiments of pharmaceutical compositions of the invention are meant to be exemplary and are not limiting.

Also provided is a method for making such pharmaceutical compositions. The method comprises admixing a compound of the invention, or a pharmaceutically acceptable salt thereof, and a pharmaceutically acceptable carrier.

Methods of the Invention

Compounds of the invention are useful for inhibiting growth of fungi and yeast, including, in particular, fungi and yeast of clinical significance as pathogens.

Advantageously, the compounds of the invention have improved therapeutic indices compared to AmB, thereby providing agents with improved efficacy and reduced toxicity as compared to AmB. Compounds of the invention are useful in methods of treating fungal and yeast infections, including, in particular, systemic fungal and yeast infections. Compounds of the invention are also useful in the manufacture of medicaments for treating fungal and yeast infections, including, in particular, systemic fungal and yeast infections. The invention further provides the use of compounds of the invention for the treatment of fungal and yeast infections, including, in particular, systemic fungal and yeast infections.

An aspect of the invention is a method of treating a fungal infection, comprising administering to a subject in need thereof a therapeutically effective amount of a compound of the invention or salt thereof, thereby treating the fungal infection.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent (%) compared to control.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease. For example, in one embodiment the terms "treating" and "treat" refer to performing an intervention that results in (a) inhibiting a fungal infection, e.g., slowing or arresting its development; or (b) relieving or ameliorating a fungal infection, e.g., causing regression of the fungal infection.

A "fungal infection" as used herein refers to an infection in or of a subject with a fungus as defined herein. In one embodiment the term "fungal infection" includes a yeast infection. A "yeast infection" as used herein refers to an infection in or of a subject with a yeast as defined herein.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In one embodiment a subject is a human.

As used herein, a "subject having a fungal infection" refers to a subject that exhibits at least one objective manifestation of a fungal infection. In one embodiment a subject having a fungal infection is a subject that has been diagnosed as having a fungal infection and is in need of treatment thereof. Methods of diagnosing a fungal infection are well known and need not be described here in any detail.

As used herein, a "subject having a yeast infection" refers to a subject that exhibits at least one objective manifestation of a yeast infection. In one embodiment a subject having a yeast infection is a subject that has been diagnosed as having a yeast infection and is in need of treatment thereof. Methods of diagnosing a yeast infection are well known and need not be described here in any detail.

In certain embodiments, the compound is administered intravenously.

In certain embodiments, the compound is administered orally.

In certain embodiments, the compound is administered systemically.

In certain embodiments, the compound is administered parenterally.

In certain embodiments, the compound is administered intraperitoneally.

In certain embodiments, the compound is administered enterally.

In certain embodiments, the compound is administered intraocularly.

In certain embodiments, the compound is administered topically.

Additional routes of administration of compounds of the invention are contemplated by the invention, including, without limitation, intravesicularlly (urinary bladder), pulmonary, and intrathecally.

As used herein, the phrase "effective amount" refers to any amount that is sufficient to achieve a desired biological effect.

As used herein, the phrase "therapeutically effective amount" refers to an amount that is sufficient to achieve a desired therapeutic effect, e.g., to treat a fungal or yeast infection.

For any compound described herein, a therapeutically effective amount can, in general, be initially determined from in vitro studies, animal models, or both in vitro studies and animal models. In vitro methods are well known and can include determination of minimum inhibitory concentration (MIC), minimum fungicidal concentration (MFC), concentration at which growth is inhibited by 50 percent ($IC_{50}$), concentration at which growth is inhibited by 90 percent ($IC_{90}$), and the like. A therapeutically effective amount can also be determined from human data for compounds of the invention which have been tested in humans and for compounds which are known to exhibit similar pharmacological activities, such as other related active agents (e.g., AmB). Higher doses may be required for parenteral administration. The applied dose can be adjusted based on the relative bioavailability and potency of the administered compound. Adjusting the dose to achieve maximal efficacy based on the methods described herein and other methods as are well-known in the art is well within the capabilities of the ordinarily skilled artisan.

For any compound described herein, a therapeutically effective amount for use in human subjects can be initially determined from in vitro studies, animal models, or both in vitro studies and animal models, A therapeutically effective amount for use in human subjects can also be determined from human data for compounds of the invention which have been tested in humans and for compounds which are known to exhibit similar pharmacological activities, such as other related active agents (e.g., AmB) Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

Dosing and Formulation

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents include other antifungal agents, including AmB, as well as other antibiotics, anti-viral agents, anti-inflammatory agents, immunosuppressive agents, and anti-cancer agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits, Multiple doses per day are contemplated to achieve appropriate systemic levels of compounds.

In one embodiment, intravenous administration of a compound of the invention may typically be from 0.1 mg/kg/day to 20 mg/kg/day. Intravenous dosing thus may be similar to, or advantageously, may exceed maximal tolerated doses of AmB, Intravenous dosing also may be similar to, or advantageously, may exceed maximal tolerated daily doses of AmB. Intravenous dosing also may be similar to, or advantageously, may exceed maximal tolerated cumulative doses of AmB.

Intravenous dosing also may be similar to, or advantageously, may exceed maximal recommended doses of AmB. Intravenous dosing also may be similar to, or advantageously, may exceed maximal recommended daily doses of AmB. Intravenous dosing also may be similar to, or advantageously, may exceed maximal recommended cumulative doses of AmB.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

Amphotericin B is commercially available in a number of formulations, including deoxycholate-based (sometimes referred to as desoxycholate-based) formulations and lipid-based (including liposomal) formulations. Amphotericin B derivative compounds of the invention similarly may be formulated, for example, and without limitation, as deoxycholate-based formulations and lipid-based (including liposomal) formulations.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, pulmonary (e.g., inhalation), and topical.

For intravenous and other parenteral routes of administration, the compounds of the invention generally may be formulated similarly to AmB. For example, a compound of the invention can be formulated as a lyophilized preparation with deoxycholic acid, as a lyophilized preparation of liposome-intercalated or -encapsulated active compound, as a lipid complex in aqueous suspension, or as a cholesteryl sulfate complex. Lyophilized formulations are generally reconstituted in suitable aqueous solution, e.g., in sterile water or saline, shortly prior to administration.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., J Appl Biochem 4: 185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate, Cationic detergents which can be used and can include benzalkoniumn chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e, g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., Pharm Res 7:565-569 (1990); Adjei et al., Int J Pharmaceutics 63:135-144 (1990) (leuprolide acetate); Braquet et al., J Cardiovasc Pharmacol 13(suppl. 5):143-146 (1989) (endothelin-1); Hubbard et al., Annal Int Med 3:206-212 (1989) (α1-antitrypsin); Smith et al., 1989, J Clin Invest 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, J Immunol 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn U nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mil of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafiuoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (p m), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation, Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, Science 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally at least one additional therapeutic agent included in a pharmaceutically acceptable carrier.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) Macromolecules 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

INCORPORATION BY REFERENCE

All U.S. patent application publications and U.S. patents mentioned herein are hereby incorporated by reference in their entirety as if each individual publication or patent was specifically and individually indicated to be incorporated by reference. In case of conflict, the application, including any definitions herein, will control.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the embodiments described herein is not intended to be limited to the above Description, but rather is as set forth in the appended claims. Those of ordinary skill in the art will appreciate that various changes and modifications to this description may be made without departing from the spirit or scope of the invention, as defined in the following claims.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1. Synthetic Procedure and HPLC Method for Disclosed Compounds

General Synthetic Procedure for Amides of AmB:

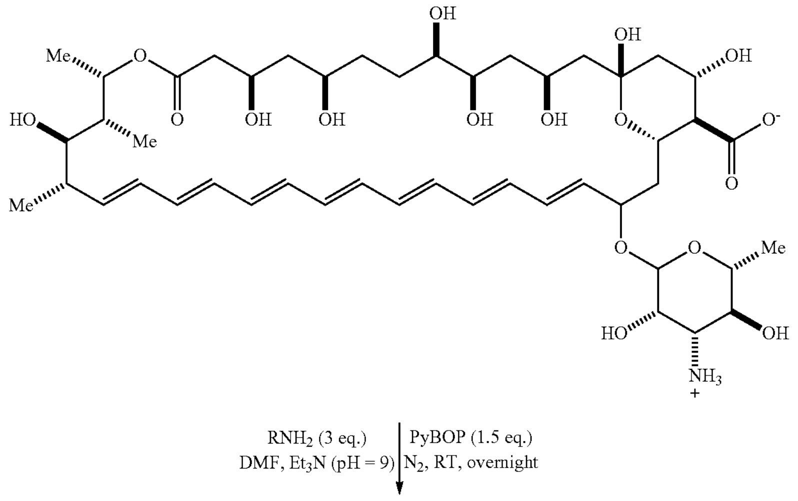

-continued

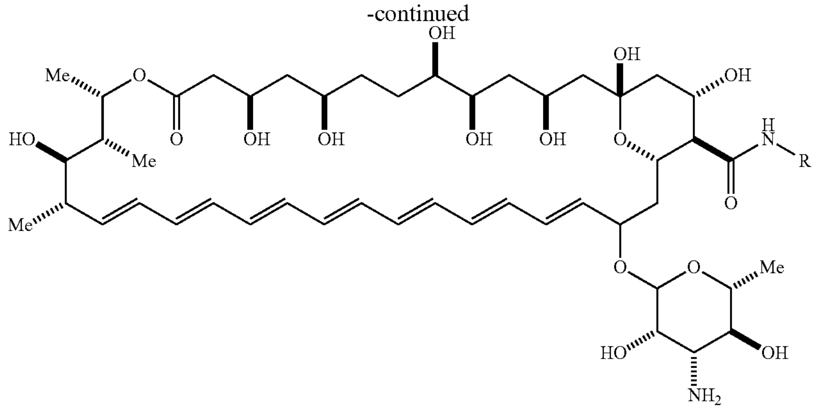

Freshly distilled $Et_3N$ was added drop wise to a solution of Amphotericin B (10 mg; 0.01 mmol) and amine (3 eq) in DMF (500 μL) until pH=9 is reached (by pH paper). The reaction mixture was stirred for 15 minutes at room temperature. Solid PyBOP (1.5 eq; 8.4 mg) was added tinder nitrogen atmosphere, and the sealed vial was stirred overnight at rt. The progress of the reaction was monitored by analytical HPLC traces.

Once completed, the product was precipitated and washed with anhydrous diethyl ether (10 mL). The suspension was centrifuged at 3000 g for 5 minutes. The solvent was decanted out and the pellet was dissolved in DMSO and filtered through 0.2 micron syringe filter for purification on C:18 Prep HPLC system. The pure product was dried on lyophilizer as yellowish powder and stored at −80° C. under nitrogen atmosphere.

The method is suitable for making the disclosed amides of C2'-epi-AmB, starting from C2' epi-AmB.

HPLC method:

Analytical Column: C18 Agilent column (Catalogue number: 993967-902)

| Time (min) | Acetonitrile | 10 mM $NH_4OAc$/0.1% Formic Acid buffer | Flow rate (mL/min) |
|---|---|---|---|
| 0 | 5 | 95 | 1.2 |
| 8 | 95 | 5 | 1.2 |

-continued

| Time (min) | Acetonitrile | 10 mM $NH_4OAc$/0.1% Formic Acid buffer | Flow rate (mL/min) |
|---|---|---|---|
| 8.5 | 95 | 5 | 1.2 |
| 9.5 | 5 | 95 | 1.2 |
| 10.5 | 5 | 95 | 1.2 |

Prep Column: C18 Agilent column (Catalogue number: 410910-502)

| Time (min) | Acetonitrile | 10 mM $NH_4OAc$ buffer | Flow rate (mL/min) |
|---|---|---|---|
| 0 | 5 | 95 | 30 |
| 1 | 5 | 95 | 50 |
| 15 | 95 | 5 | 50 |
| 16 | 95 | 5 | 50 |
| 17 | 5 | 95 | 50 |
| 18 | 5 | 95 | 30 |

Synthesis of Compound 1

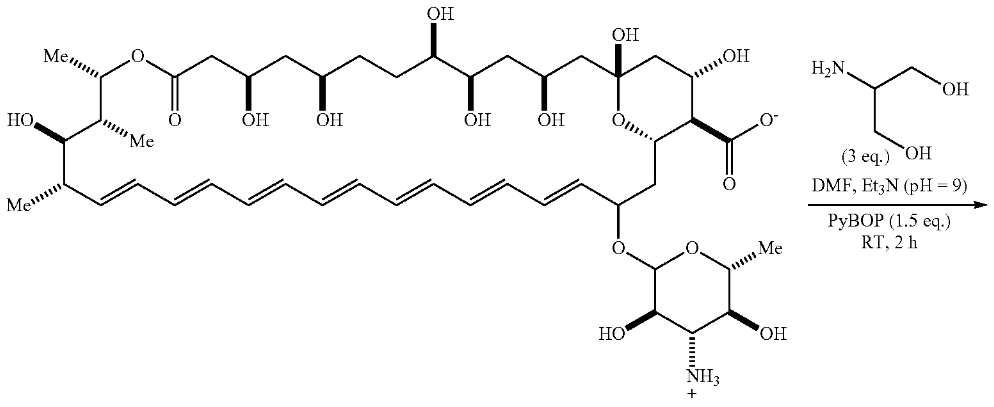

C2'epiAmB

-continued

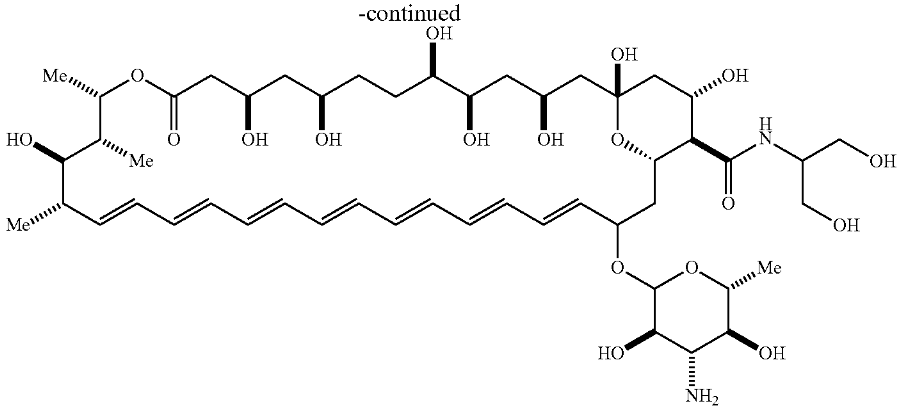

Fresh $Et_3N$ (directly from bottle) (12 μL) was added to a solution of C2'epiAmB (10 mg; 0.01 mmol) and 2-Amino-1,3-propanediol (3 eq; 3 mg) in DMF (400 μL). The reaction mixture was stirred for 15 minutes at room temperature. Solid PyBOP (1.5 eq; 8.4 mg) was added to the mixture, and the sealed vial was stirred for 2 h at rt. The progress of the reaction was monitored by analytical HPLC traces.

Once completed, the reaction was diluted with DMSO to form a clear solution and filtered through 0.2 micron syringe filter before purification on C18 Prep HPLC system. The pure product was dried on lyophilizer as yellowish powder and stored at −80° C. under inert atmosphere.

Yield 5.6 mg (52%)

Product Mol. Wt.: 997.1860

Synthesis of Compound 3 from Compound 1

In a clean oven dried 40 mL glass vial, containing 50 mg (X mg) of HPLC purified Compound 1, add 2.5 mL (0.05X mL) of milliQ water followed by 200 mL (4X mL) of 0.5 (M) acetic acid. After addition of acid the solution will start to clear up. Vortex the solution as necessary to dissolve the solute completely. Following the sonication of the solution for 1-2 mins at room temperature, add a clean stirring bead to the solution and stir it for 15 mins at 800 rpm. Check for any solid residue, adhered on the top part of the glass vial. After the stirring is complete visually check the solution for any sign of insoluble portion or suspension. Now remove the stirring bead from the solution, freeze it in liquid nitrogen and put it on the lyophilizer for overnight drying.

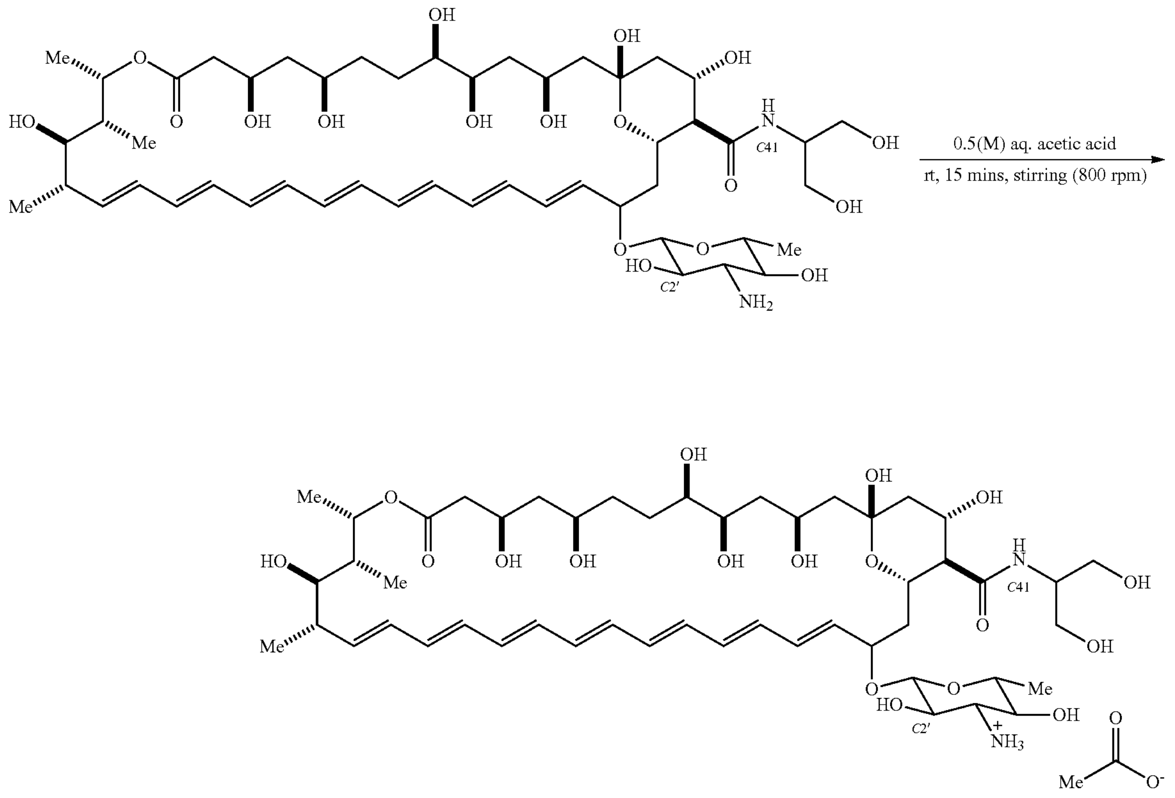

Synthesis of Compound 4

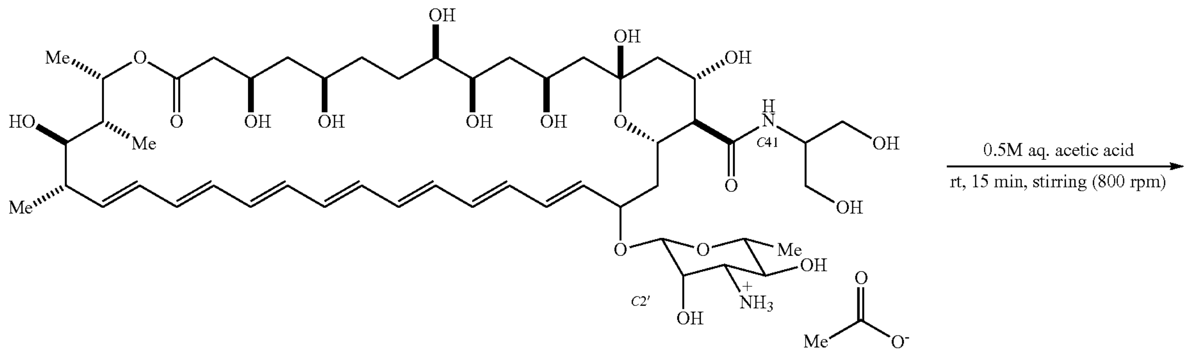

Compound A

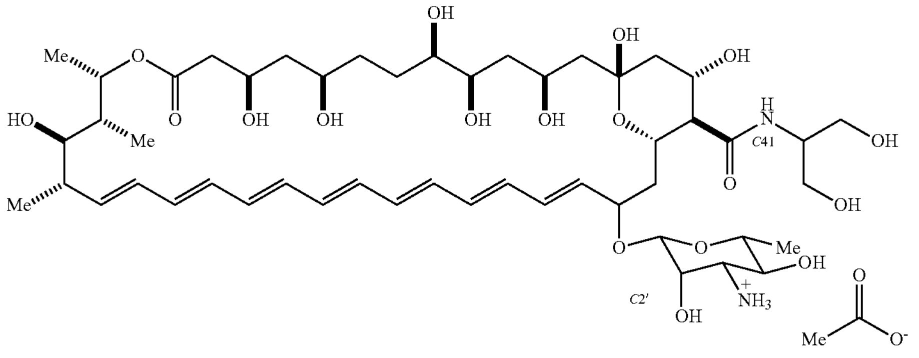

Compound 4

In a clean oven dried 40 mL glass vial, containing 50 mg (X mg) of HPLC purified Compound A, add 2.5 mL (0.05X mL) of milliQ water followed by 200 ml (4X mL) of 0.5 (M) acetic acid. After addition of acid the solution will start to clear up. Vortex the solution as necessary to dissolve the solute completely. Following the sonication of the solution for 1-2 mins at room temperature, add a clean stirring bead to the solution and stir it for 15 mins at 800 rpm. Check for any solid residue, adhered on the top part of the glass vial. After the stirring is complete visually check the solution for any sign of insoluble portion or suspension. Now remove the stirring bead from the solution, freeze it in liquid nitrogen and put it on the lyophilizer for overnight drying.

Example 2. Characterization Data for Disclosed Compounds

Compound 1

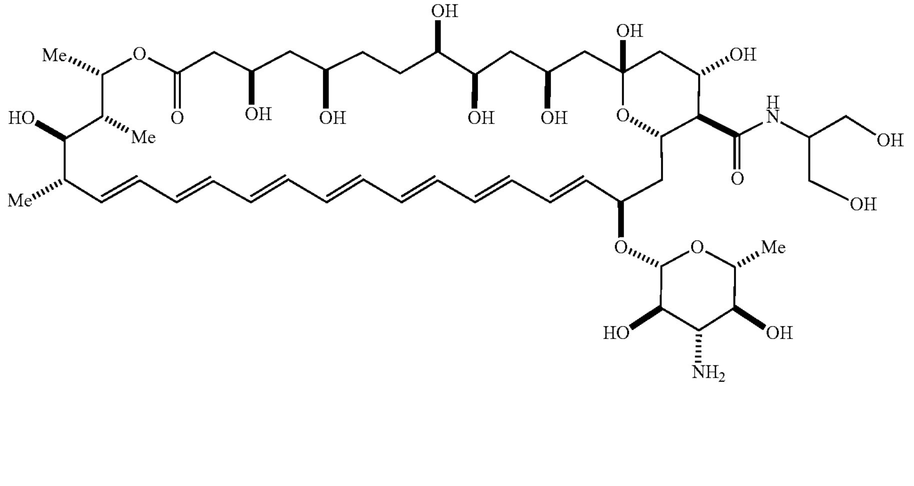

Figure 4A:
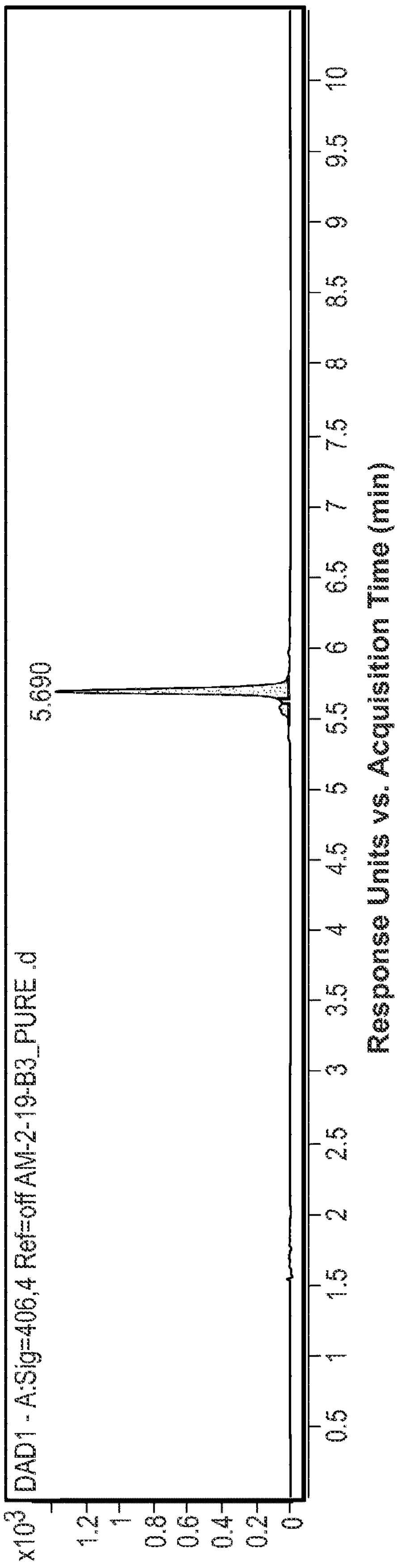
FIGS. 4A-4C depict characterization data for Compound 1; $^{1}H$ NMR parameters: 500 MHz, pyridine-$d_5$:$CD_3OD$ (1:1).
Figure 4B:
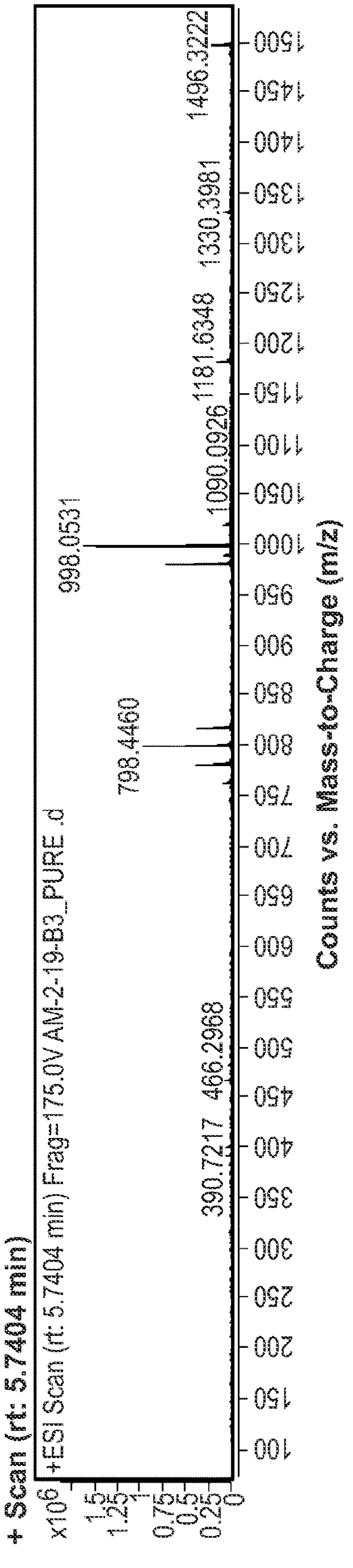
Figure 4C:
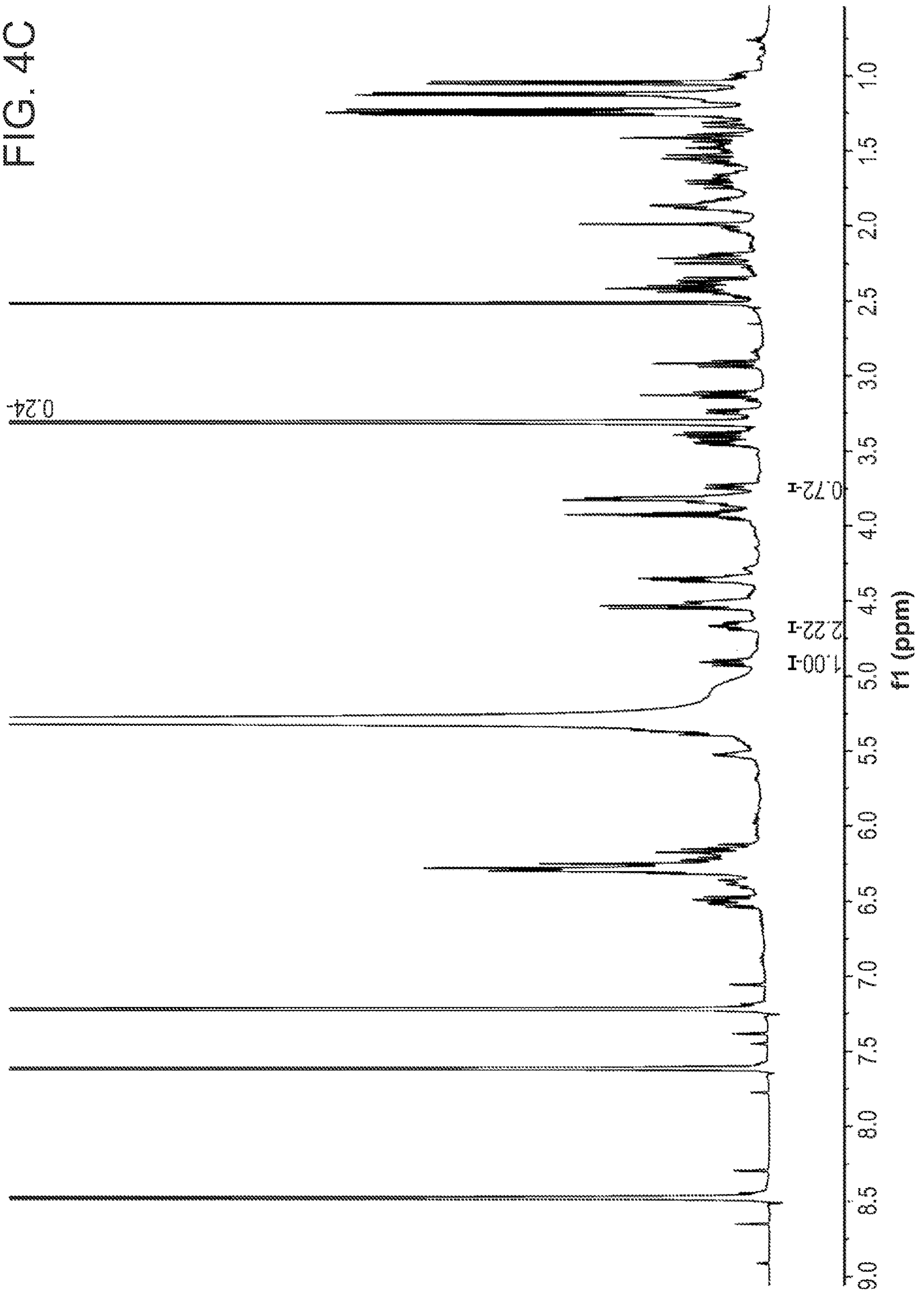

NMR spectrum of compound 1 is shown in FIG. 4C.

LCMS: $[M+H]^+$=998.1935. Chromatograph and mass spectrum for compound 1 are shown in FIG. 4A and FIG. 4B.

Synthesis of Compound 4

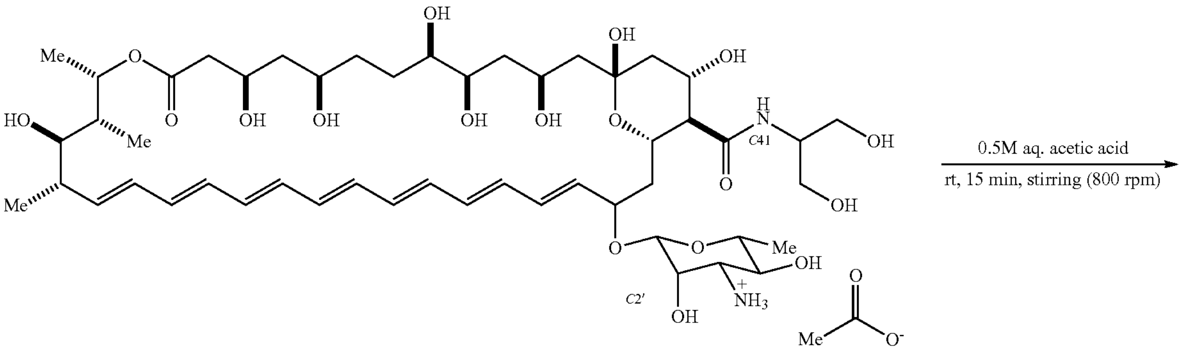

Compound A

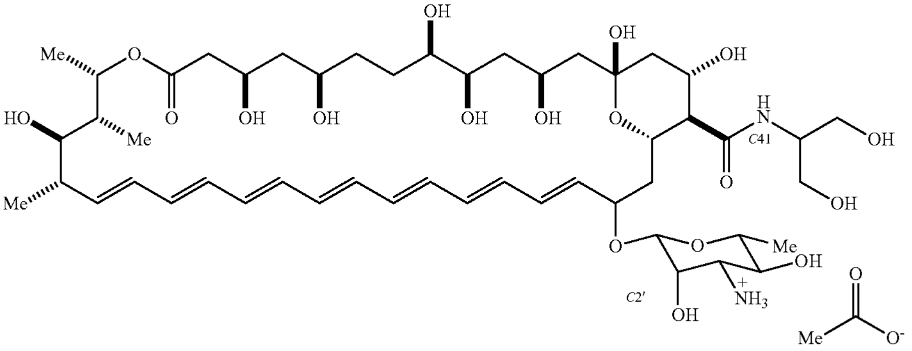

Compound 4

In a clean oven dried 40 mL glass vial, containing 50 mg (X mg) of HPLC purified Compound A, add 2.5 mL (0.05X mL) of milliQ water followed by 200 mL (4X mL) of 0.5 (M) acetic acid. After addition of acid the solution will start to clear up. Vortex the solution as necessary to dissolve the solute completely. Following the sonication of the solution for 1-2 mins at room temperature, add a clean stirring bead to the solution and stir it for 15 mins at 800 rpm. Check for any solid residue, adhered on the top part of the glass vial. After the stirring is complete visually check the solution for any sign of insoluble portion or suspension. Now remove the stirring bead from the solution, freeze it in liquid nitrogen and put it on the lyophilizer for overnight drying.

Figure 5A:
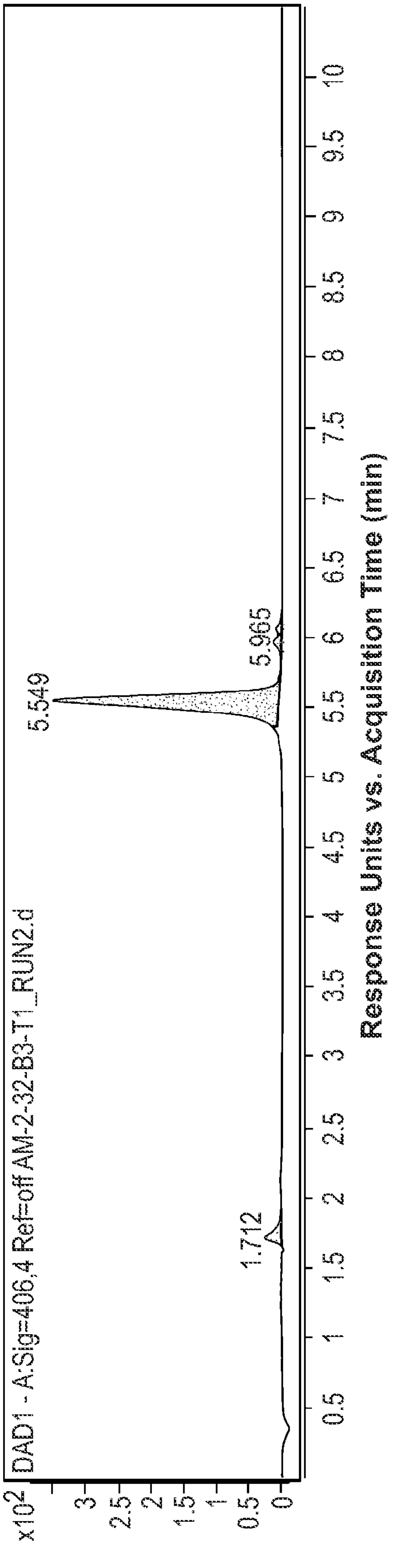
FIGS. 5A-5B depict characterization data for Compound 2.
Figure 5B:
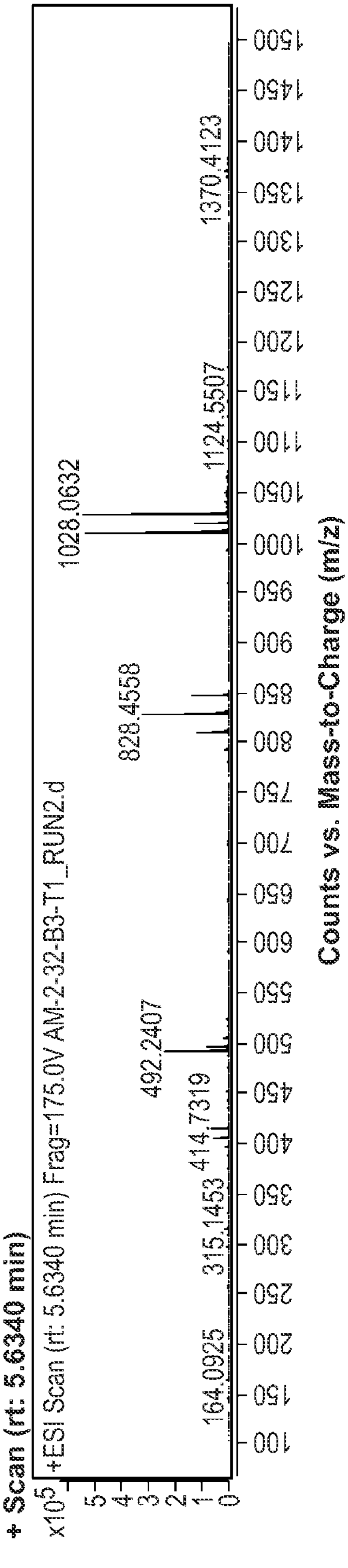

Example 2. Characterization Data for Disclosed Compounds
Compound 1
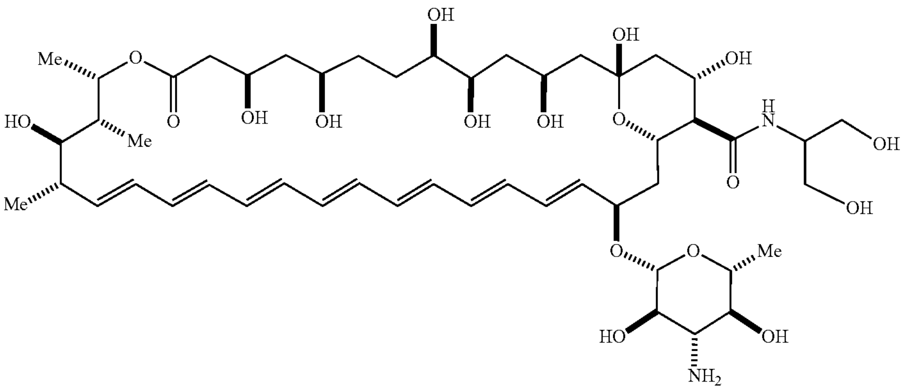
NMR spectrum of compound 1 is shown in FIG. 4C.
LCMS: $[M+H]^+$=998.1935. Chromatograph and mass spectrum for compound 1 are shown in FIG. 4A and FIG. 4B.
Compound 2
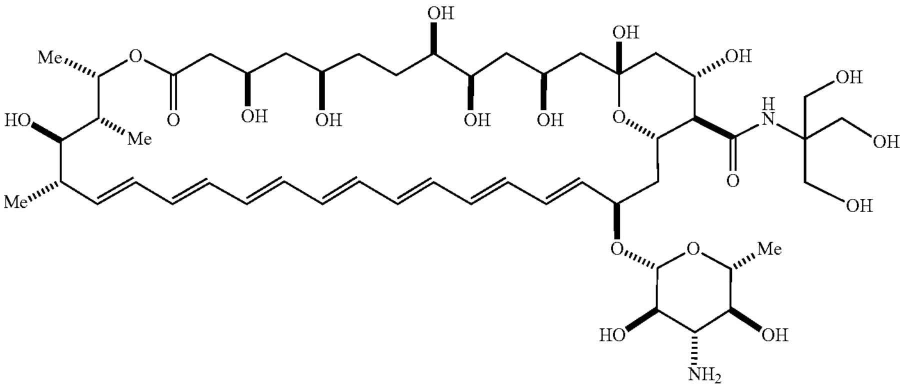
LCMS: $[M+H]^+$=1028.2195. Chromatograph and mass spectrum for compound 2 are shown in FIG. 5A and FIG. 5B
Compound 3
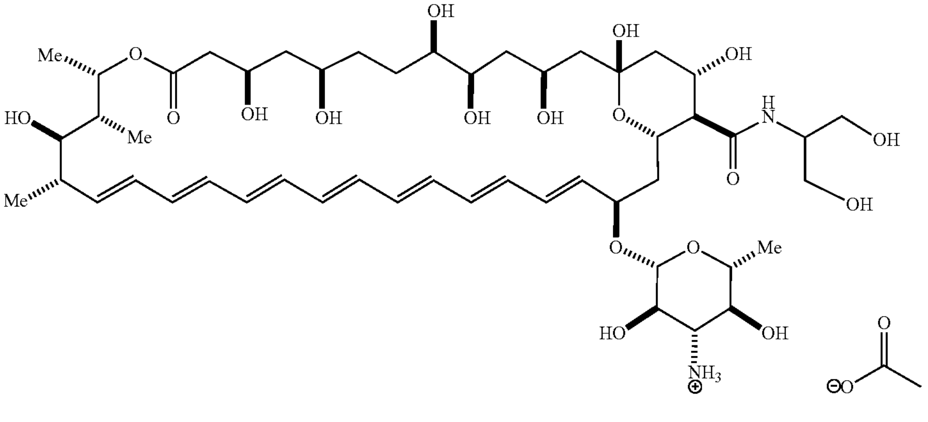

Figure 19A:
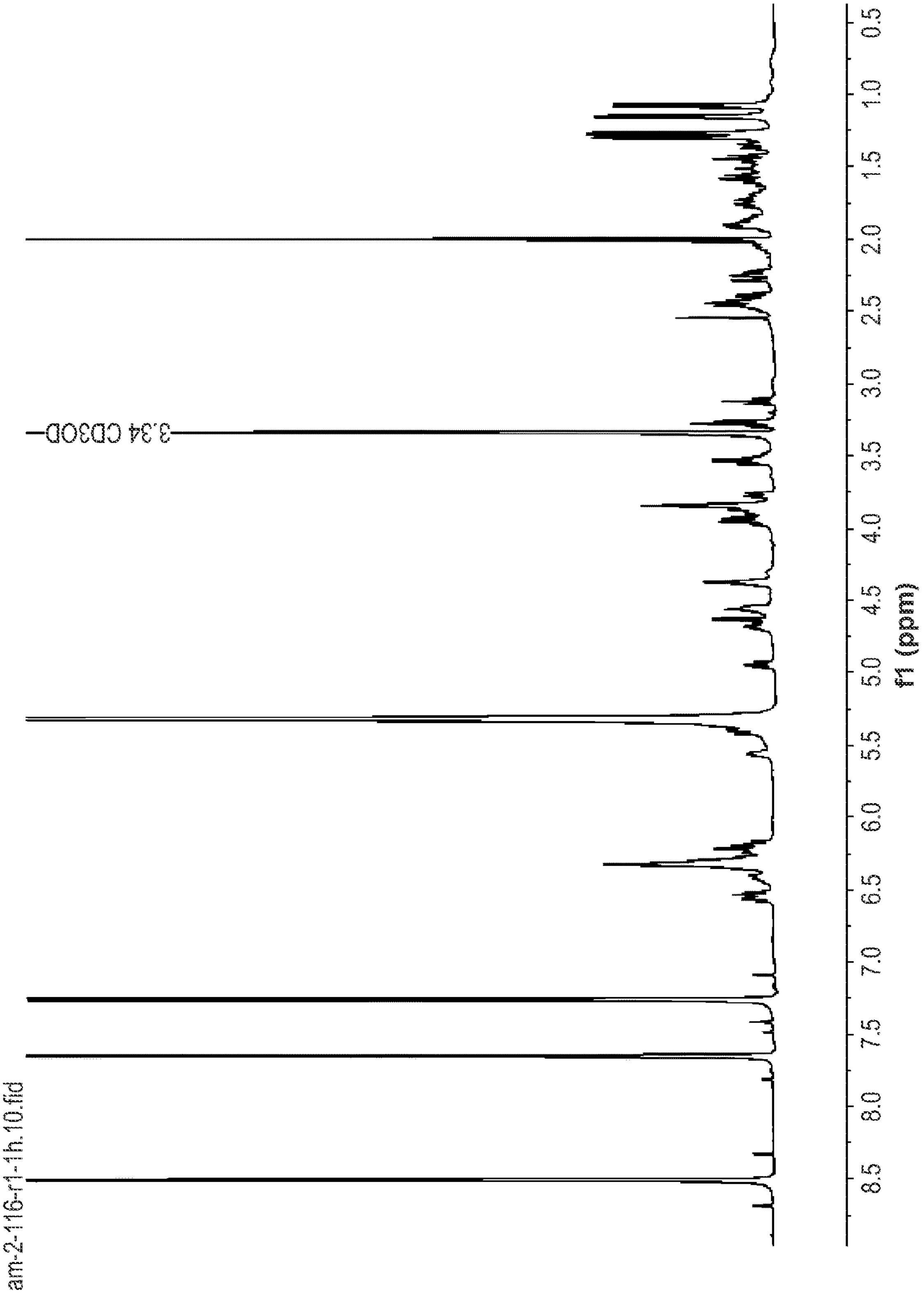
FIGS. 19A-19D depict characterization data for Compound 3; $^{1}H$ NMR parameters: 500 MHz, pyridine-$d_5$:$CD_3OD$ (1:1); $^{13}C$ NMR parameters: 126 MHz, pyridine-$d_5$:$CD_3OD$ (1:1).

$^1H$ NMR spectrum of compound 3 is shown in FIG. 19A.

Figure 19B:
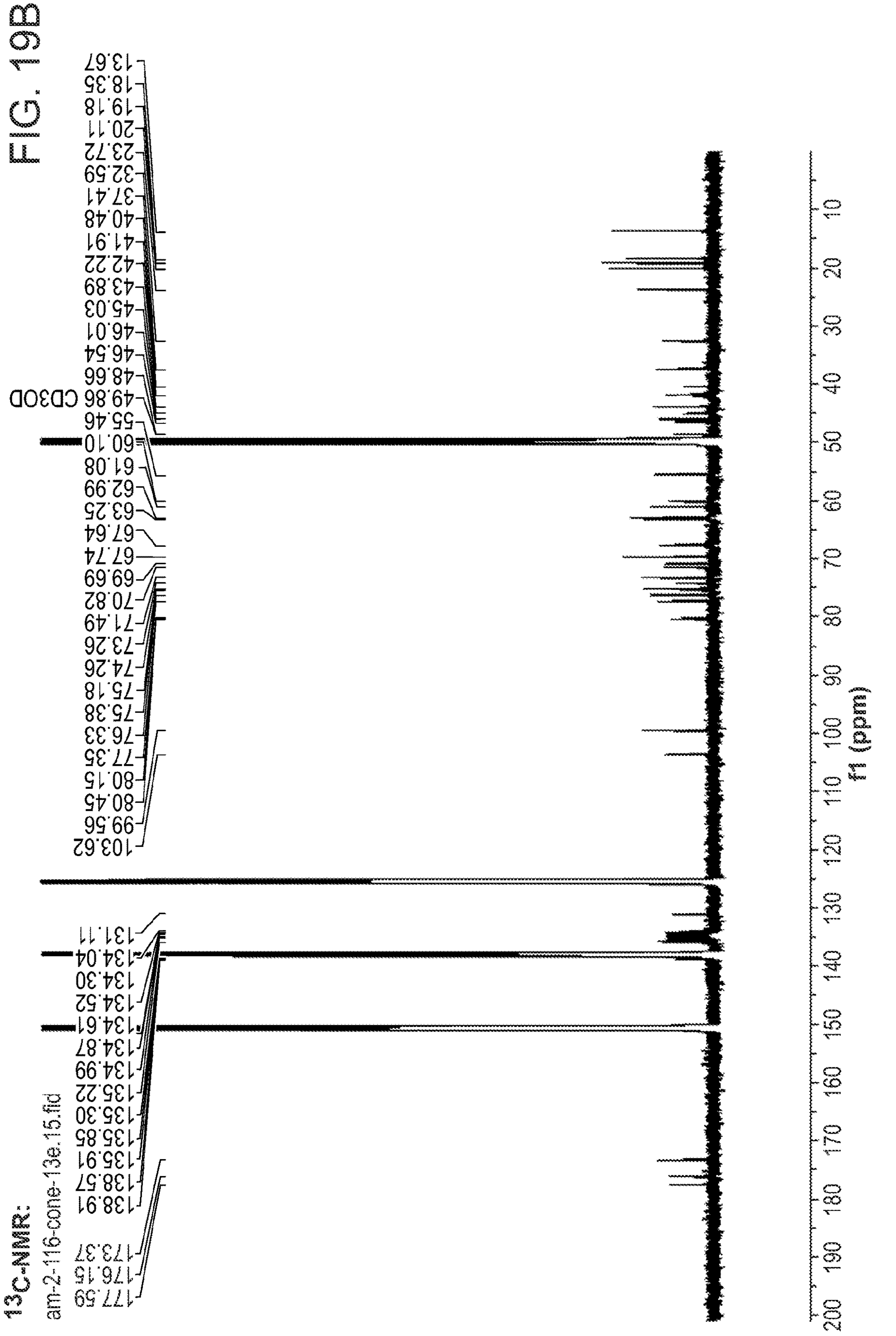

$^{13}C$ NMR spectrum of compound 3 is shown in FIG. 19B.

Figure 19C:
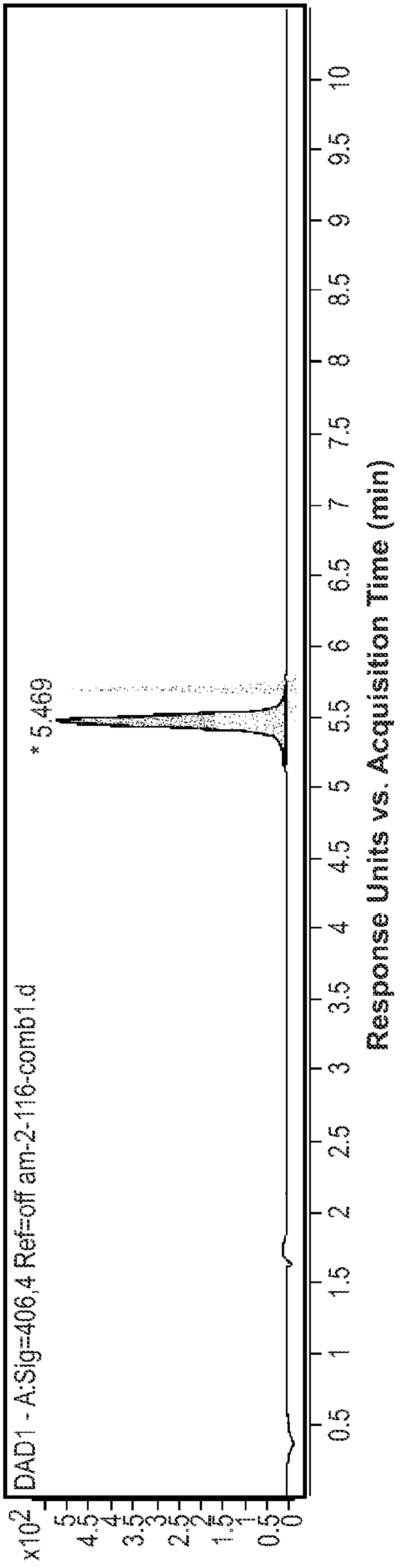
Figure 19D:
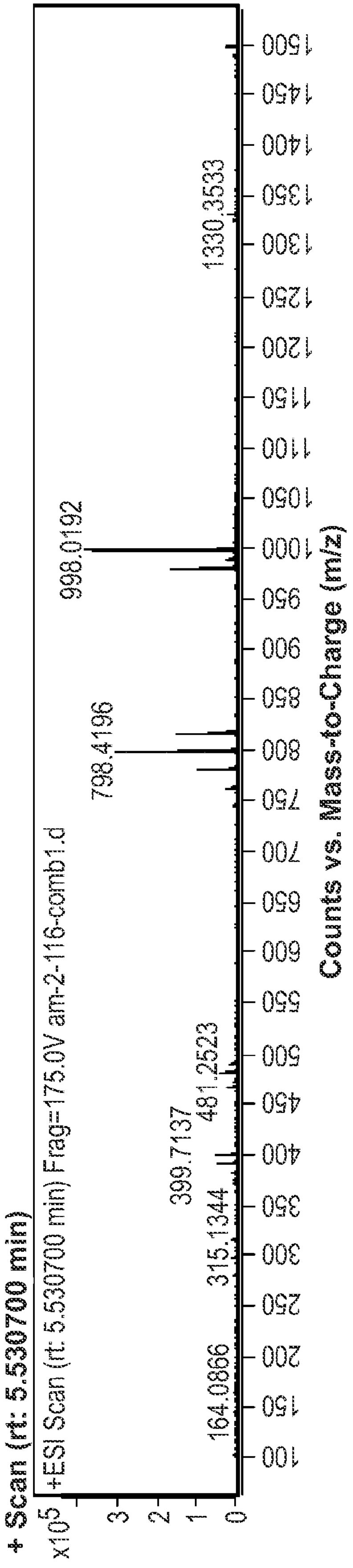

LCMS: $[M+H]^+$=998.0192. Chromatograph and mass spectrum for compound 3 are shown in FIG. 19C and FIG. 19D Compound 4

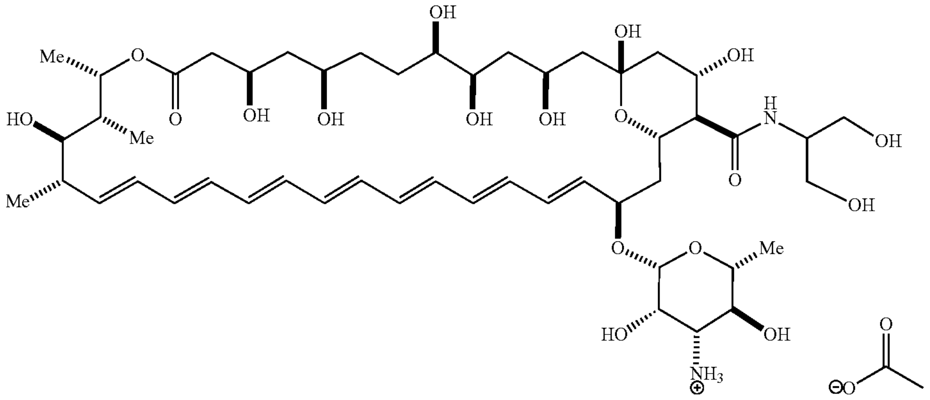

Figure 24A:
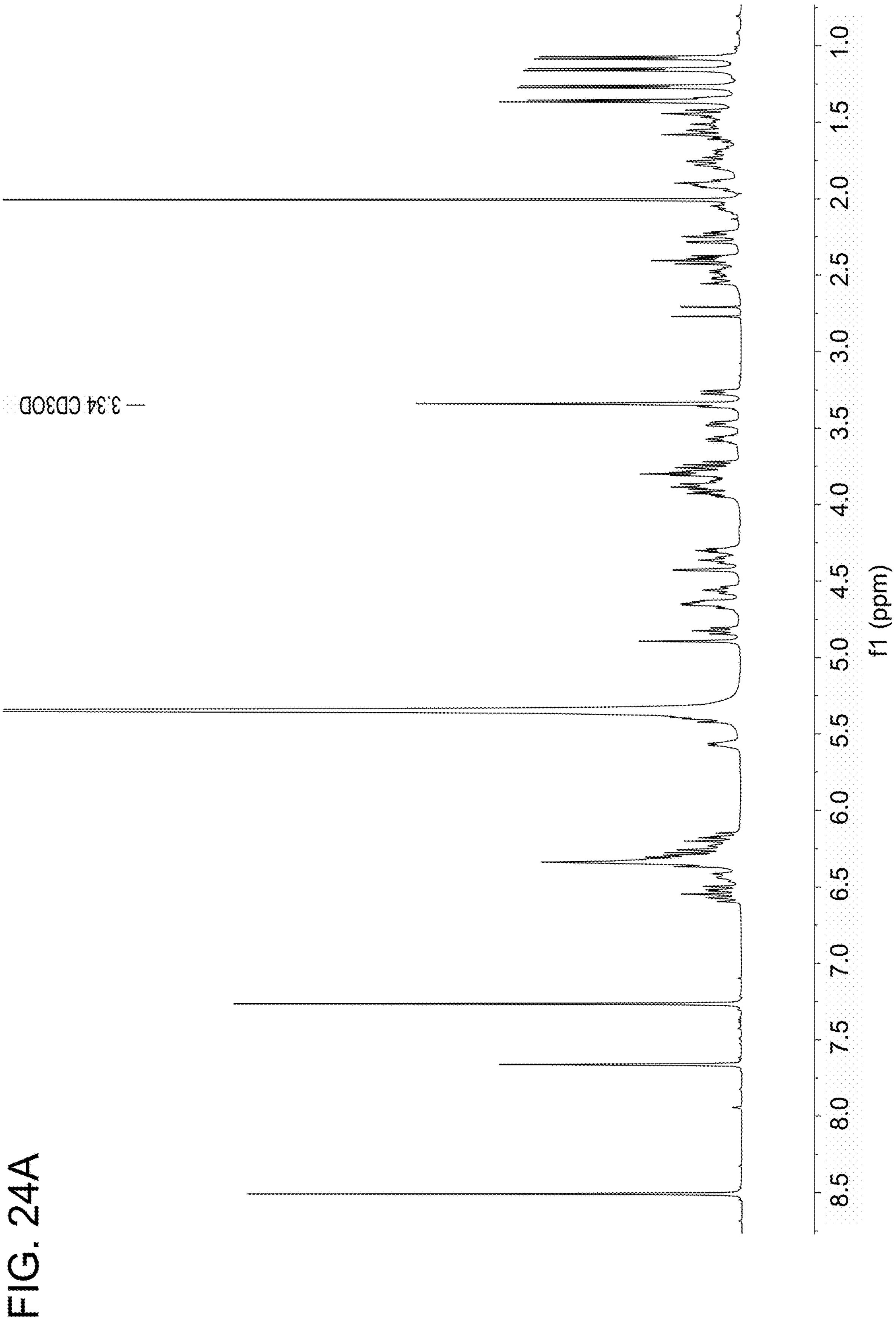
FIGS. 24A-24D depict characterization data for Compound 4; $^{1}H$ NMR parameters: 500 MHz, pyridine-$d_5$:CD-OD (1:1); $^{13}C$ NMR parameters: 126 MHz, pyridine-$d_5$: $CD_3OD$ (1:1).

$^1H$ NMR spectrum of compound 3 is shown in FIG. 24A.

Figure 24B:
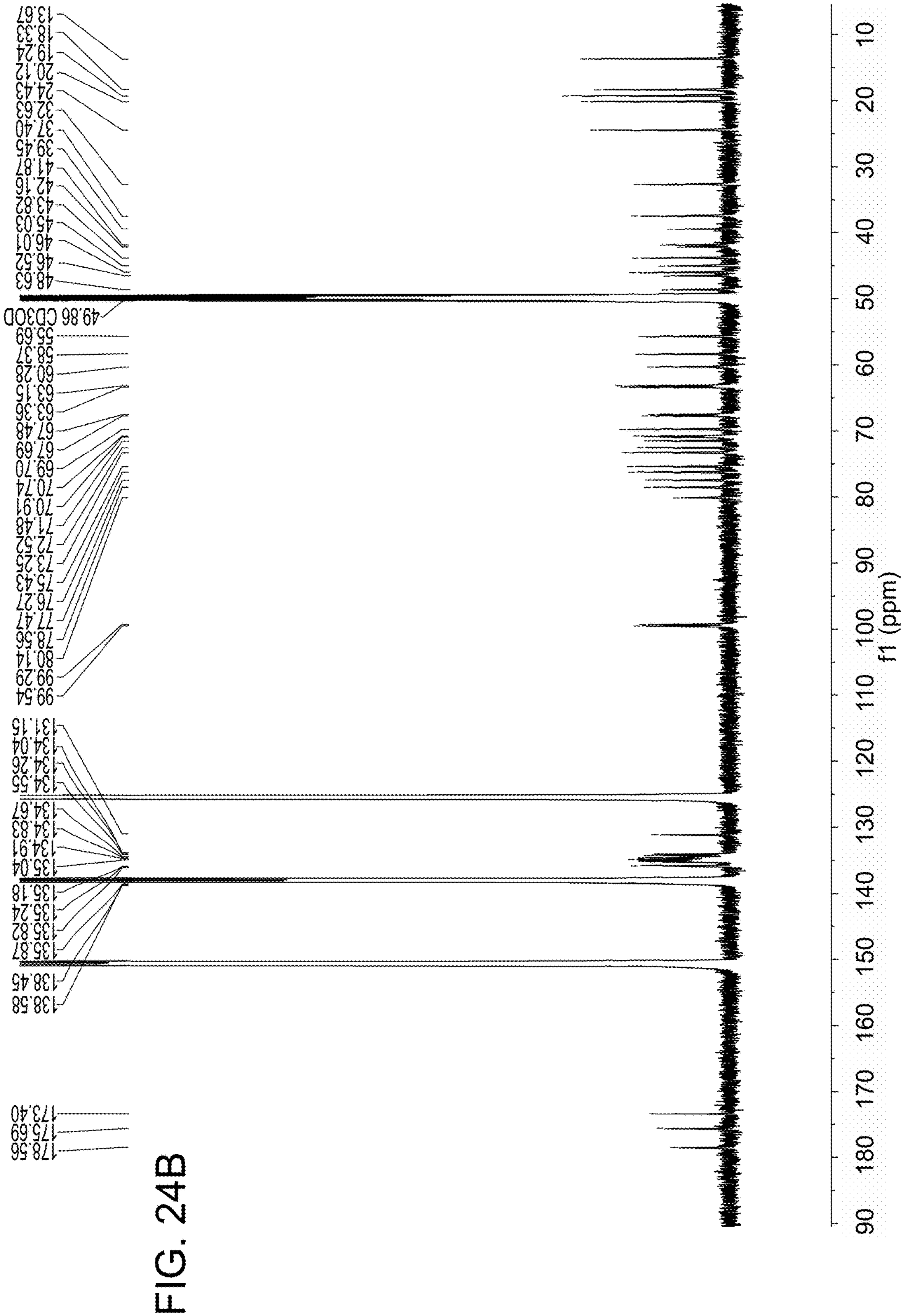

$^{13}C$ NMR spectrum of compound 3 is shown in FIG. 24B.

Figure 24C:
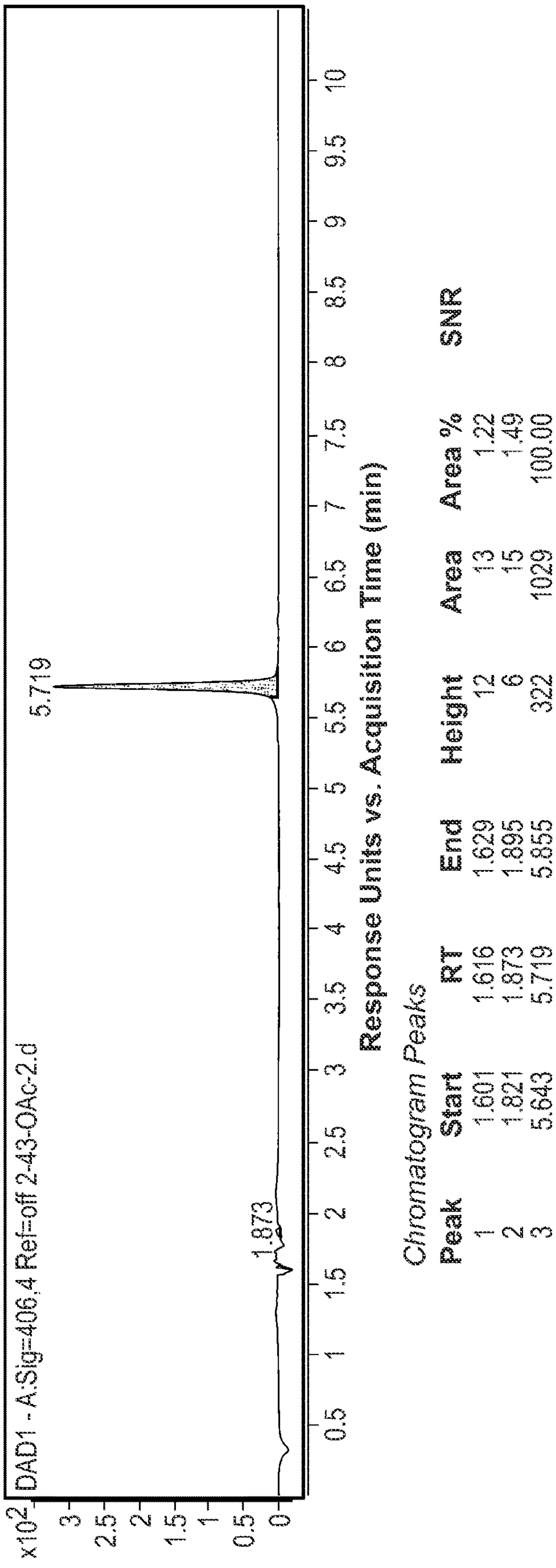
Figure 24D:
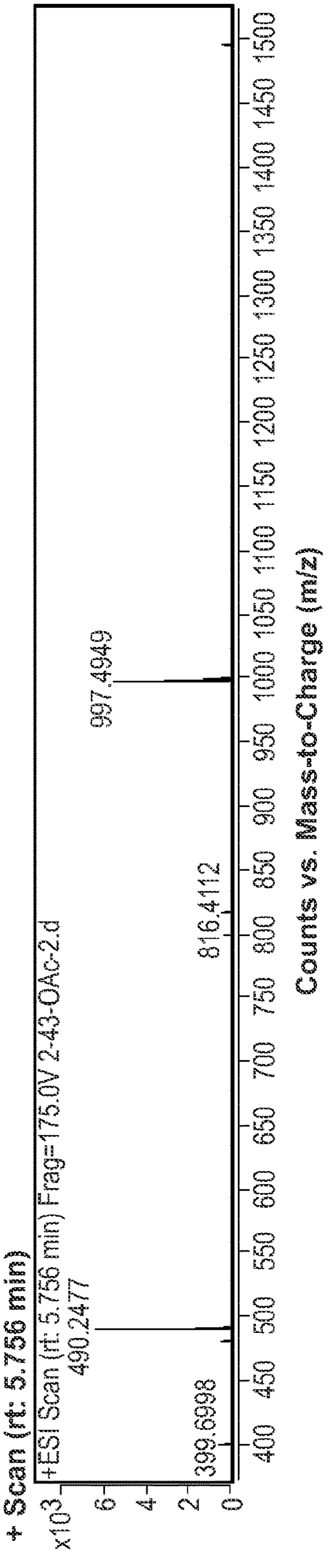

LCMS: $[M+H]^+$=997.4949. Chromatograph and mass spectrum for compound 4 are shown in FIG. 24C and FIG. 24D.

Example 3. Disclosed Compounds Show Comparable Efficacy and DMPK to AmB, but with Improved Safety

TABLE 1

Efficacy, Safety, and DMPK data for the disclosed compounds and AmB.

| | AmB | Compound 1 | Compound 2 |
|---|---|---|---|
| EFFICACY | | | |
| $MIC_{avg}$ yeast (5 strains) | 0.23 | 0.53 | 0.41 |
| $MIC_{avg}$ moulds (3 strains) | 0.92 | 1.6 | 1 |
| $MIC_{avg}$ yeast (46 strains) | 0.9 | 2.1 | 2.3 |
| $MIC_{avg}$ moulds (159 strains) | 0.9 | 1.4 | 2.6 |
| Mouse candidiasis model 5 mpk; Log (CFU/mL) | 5.2 | 4.8 | ND |
| SAFETY | | | |
| Binds Cholesterol | Yes | No | No |
| MHC | 8.4 | >100 | >60 |
| Mouse single IV injection: mortality (40 mpk) | 0/3 | 0/4 | ND |
| Renal toxicity biomarkers KIM1, LCN2, TIMP1, SPP1 | elevated | ND | ND |
| DMPK | | | |
| Liver microsome ($T_{1/2}$, min) Mouse, rat, dog, monkey, human | >145 All species | >145 All species | >145 All species |
| Blood Plasma Stability ($T_{1/2}$, min) Mouse; Human | >289; >289 | >289; >289 | 265.1; >289 |
| P450 Inhibition (%) 1A2; 2C9; 2C19; 2D6; 3A4 | 23.1; 4.1; 7.3, 2.3; 8.1 | 8.7; 26.9: 0.0; 0.0; 14.5 | 0.0; 0.0; 1.1; 0.0; 14.5 |
| In vivo PK: [1 mg/kg]; 5 mg/kg $T_{1/2}$, (h), Cl (mL/min/kg), $AUC_{0-inf}$ (ng*hr/mL) | ND | [8.37; 0.891; 18785] 9.6; 1.05; 79575 | ND |

Example 4. Anti-Fungal Potency for Disclosed Compounds and AmB

Colonies of fungus or mould from SDA plate was suspended in RPMI media and the innoculam density was maintained to $10^5$ CFU/mL. 990 μL aliquots of the dilute cell suspension were added to a sterile 1.7 mL eppendorf tubes followed by 10 uL of 400 uM solution of the compound (in DMSO). The concentration of DMSO in each eppendorf tube was 1% and a control sample to confirm viability using only 1% DMSO was also performed. At predetermined time points (0, 0.5, 1, 2, 3, 4, 5, 6, 8, 10, and 24 h), a 10 μL sample was removed from each tube and serially diluted 10 fold with RPMI, and a 10 μL aliquot was plated onto a SDA plate for colony count determination. When colony counts were expected to be less than 1,000 CFU/mL, a 50 μL aliquot was taken directly from the test solution and plated onto a SDA plate without dilution, Plates were incubated at 37° C. for 24 prior to examination. All experiments were conducted in duplicate.

TABLE 2

Minimum Inhibition Concentrations Against Different Moulds for AmB (AmBisome) and the Disclosed Compounds.

| MIC (μM) | # of Isolates | AmB | Compound 1 | Compound 2 |
|---|---|---|---|---|
| *A. fumigatus* | 5 | 0.71 | 1.33 | 2.33 |
| *A. flavus* | 6 | 1.16 | 1.67 | 1.67 |
| *A. niger* | 6 | 0.21 | 0.5 | 0.75 |
| *A. terreus* | 6 | 3 | 2 | 2.3 |
| *A. calldoustus* | 6 | 1.5 | 2.17 | 2.33 |
| *A. lentulus* | 6 | 3.75 | 2.33 | 4.33 |
| *A. thermomutatus* | 6 | 0.6 | 1.45 | 2.1 |
| *A. tubingensis* | 6 | 0.125 | 0.83 | 0.92 |
| *Mucor circinelloides* | 6 | 0.125 | 0.58 | 0.92 |
| *Mucor janssenii* | 6 | 0.06 | 0.5 | 0.92 |
| *Mucor velutinosus* | 6 | 0.08 | 0.67 | 1.17 |
| *Histoplasma capsulatum* | 6 | 0.06 | 0.06 | 0.08 |
| *Coccidioides immitis* | 6 | 0.125 | 0.27 | 0.27 |
| *Coccidioides posadasii* | 6 | 0.06 | 0.25 | 0.5 |
| *Fusarium oxysporum* | 6 | 1.5 | 6 | 13.3 |
| *Fusarium solani* | 6 | 1.33 | 5.67 | 14 |
| *P. variotii* MYA-3630 (QC) | 5 | 1 | 2 | 2.67 |
| *Cunninghamella* sp. | 6 | 2 | 4 | 5.33 |
| *Licht. Corymbifera* | 6 | 0.23 | 0.5 | 1 |
| *Licht. Ramosa* | 6 | 0.15 | 0.58 | 0.75 |
| *Syncephalastrum* sp. | 6 | 0.06 | 0.5 | 1 |
| *Claophialophora bantiana* | 6 | 0.375 | 1.17 | 1.83 |
| *Blastomyces dermatitidis* | 5 | <0.03 | 0.25 | 0.6 |
| *Fonsecaeu* sp. | 6 | <0.03 | <0.03 | <0.03 |
| *Talaromyces marneffei* | 6 | 0.09 | 0.12 | 0.21 |
| *Apophysomyces* sp. | 3 | 0.75 | 6.8 | 8.3 |
| *Saksenaea* sp. | 4 | 0.06 | 0.23 | 0.36 |
| Average MIC | 157 | 0.9 | 1.4 | 2.6 |

TABLE 2A

Minimum Inhibition Concentrations Against Different Moulds for AmB (AmBisome) and the Disclosed Compounds.

| MIC (μM) | # of Isolates | AmB | Compound 3 |
|---|---|---|---|
| *A. fumigatus* | 16 | 2.1 | 3.3 |
| *A. terreus* | 5 | 7 | 3.2 |
| *A. flavus* | 3 | 4 | 3.3 |

TABLE 3

Minimum Inhibition Concentrations Against Different Yeasts for AmB (AmBisome) and the Disclosed Compounds.

| MIC (μM) | # of Isolates | AmB | Compound 1 | Compound 2 |
|---|---|---|---|---|
| *Candida auris* | 10 | 1.2 | 2.6 | 2.6 |
| *Candida krusei* | 2 | 1 | 2 | 3 |
| *Candida parapsilosis* | 8 | 1.1 | 1.8 | 1.6 |
| *Cryptococcus neoformans* | 10 | 0.55 | 2 | 2 |
| *Cryptococcus gattii* | 10 | 0.75 | 1.6 | 2 |
| *Rhodotorula* sp. | 6 | 1 | 2.8 | 3.7 |
| Average MIC | 46 | 0.9 | 2.1 | 2.3 |

TABLE 3A

Minimum Inhibition Concentrations Against Different Yeasts for AmB (AmBisome) and the Disclosed Compounds.

| MIC (μM) | # of Isolates | AmB | Compound 3 |
|---|---|---|---|
| *Candida albicans* | 15 | 0.61 | 2.1 |
| *Candida tropicalis* | 10 | 0.8 | 1.6 |
| *Candida parapsilosis* | 6 | 0.5 | 1.8 |
| *Candida glabrata* | 5 | 1.4 | 1.8 |
| *Candida auris* | 15 | 2.9 | 2.3 |
| *Candida krasei* | 4 | 2.5 | 4 |
| *Cryptococcus neoformans* | 3 | 1.17 | 2.33 |
| *Cryptococcus gatti* | 1 | 1 | 2 |
| *Trichophyton rubrum* | 3 | 1.1 | 2.6 |
| *Trichophyton mentagropytes* | 3 | 4 | 3.3 |
| *Malassezia furfur* | 3 | >16 | >16 |
| *Fusarium solani* | 2 | 3 | 6 |
| *Microsporum canis* | 2 | 0.56 | 0.75 |
| *Scedosporium apiospermum* | 2 | >16 | >16 |
| *Scedosporium prolificans* | 2 | >16 | >16 |
| *Epidermophyton floccosum* | 2 | 0.38 | 1.5 |

TABLE 4

Minimum Inhibition Concentrations Against Different Rare Moulds Resistant to AmB for AmB (AmBisome) and the Disclosed Compounds.

| MIC (μM) | # of Isolates | AmB | Compound 1 | Compound 2 |
|---|---|---|---|---|
| *Sporothrix schenckii* | 6 | 4 | 6 | >5.2 |
| *Purpureocillium lilacinum* | 6 | >16 | >16 | >16 |
| *Scedosporium aurantiacum* | 4 | >16 | >16 | >16 |
| *Scedosporium boydii* | 6 | >16 | >16 | >16 |
| *Lomentospora prolificans* | 6 | >16 | >16 | >16 |
| Average MIC | 28 | | | |

Example 5. In Vitro and In Vivo Safety of the Disclosed Compounds

UV-Vis is Binding Assay (FIG. 1A): The protocol for the sterol binding assay (UV-Vis) was developed in our lab. Compounds were dissolved in DMSO at a final concentration of 1 mM. Sterol were first dissolved in CHCl3 (>200 mM) and then diluted to 1 mM concentration with DMSO To synthesize the complex 1 ul of compound solution was taken in a clean eppendorf tube (2 ml) and sterol solution (volume depends on the stoichiometry) was added to it and the volume was made up to 20 ul with DMSO. 0.98 ml of PBS buffer was added to the Eppendorf tube and mixed properly. The absorbance of the solution was measured after 30 mins of incubation.

Figure 1B:
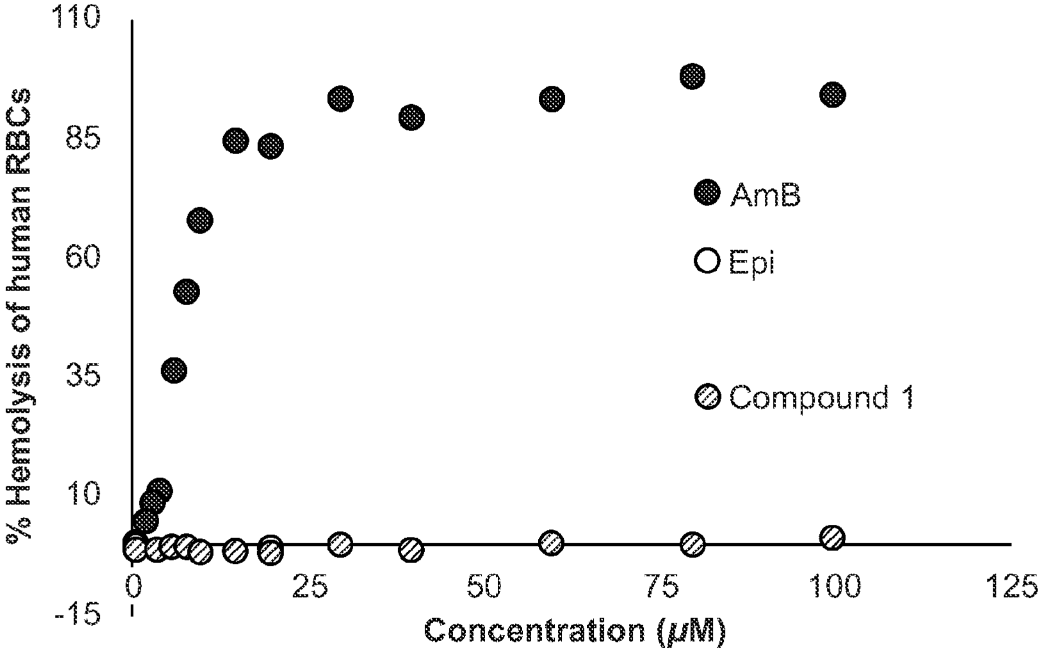

MHC (FIG. 1B and FIG. 10): The protocol for the hemolysis assay was adapted from the report of Paquet and coworkers (Chem. Eur. J. 2008, 14, 2465-2481). Whole human blood (sodium heparin) was purchased from Biorec-lamation LLC (Westbury, NY) and stored at 4° C. and used within two days of receipt. To a 2.0 mL appendorf tube, 1 mL of whole human blood was added and centrifuged at 10,000 g for 2 minutes. The supernatant was removed and the erythrocyte pellet was washed with 1 mL of sterile saline and centrifuged at 10,000 g for 2 minutes. The saline wash was repeated for a total of three washes. The erythrocyte pellet was suspended in 1 mL of RBC buffer (10 mM NaH2PO4, 150 mM NaCl, 1 mM MgCl2, pH 7.4) to form the erythrocyte stock suspension.

Compounds were prepared as >15 mM stock solutions in DMSO and serially diluted to the following concentrations with DMSO: 7689, 5126, 2563, 2050, 1538, 1025, 769, 513, 384, 256, 205, 154, 103, 77, 51, 26 μM. To a 0.2 mL PCR tube, 24 μL of RBC buffer and 1 μL of compound stock solution were added, which gave final concentrations of 500, 300, 200, 100, 80, 60, 40, 30, 20, 15, 10, 8, 6, 4, 3, 2, 1 μM. Positive and negative controls were prepared by adding 1 μL of DMSO to MilliQ water or RBC buffer, respectively to 0.2 mL PCR tube. To each PCR tube, 0.63 μL. of the erythrocyte stock suspension was added and mixed by inversion. The samples were incubated at 37° C. for 2 hours. The samples were mixed by inversion and centrifuged at 10,000 g for 2 minutes. 15 μL of the supernatant from each sample was added to a 384-well place. Absorbances were read at 540 nm using a Biotek H1 Synergy Hybrid Reader (Winooski, VT), Experiments were performed in triplicate and the reported MHC represents an average of three experiments.

Example 6. In Vivo Mouse Pharmacokinetic Experiments for Disclosed Compounds

Figure 2:
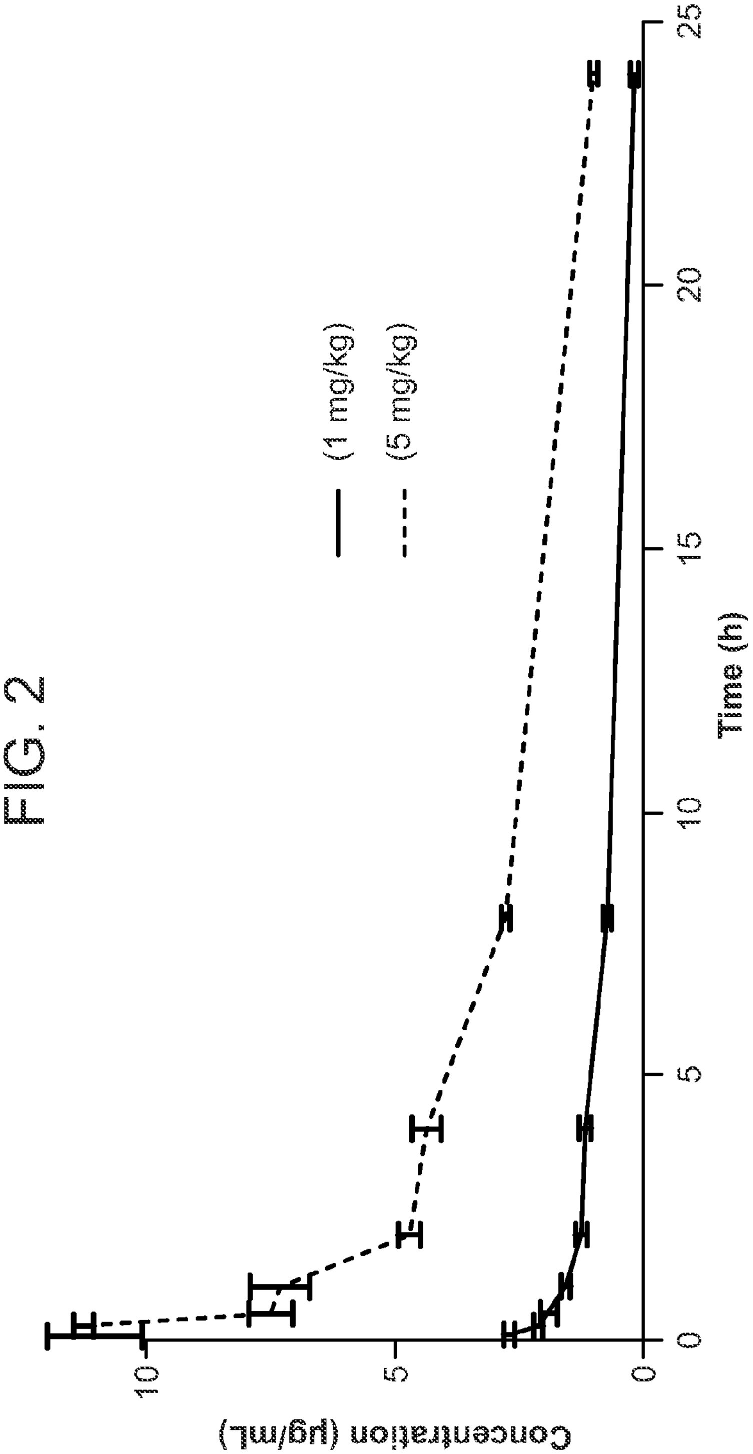
FIG. 2 depicts in vivo mouse pharmacokinetic data for Compound 1.

Mouse PK (FIG. 2): The experiment was performed using the compounds synthesized in lab and purified by preparative HPLC (>91%). All the compounds were dissolved in D5W (5% dextrose in water) at for IV injection. Female CD-1 mice were (3 per group; body weight approx. 30 g each) injected with the compounds (as per planned dosage) and the blood samples were collected at different time points and the compound content was analysed using the following procedure.

Instrument: Triple Quad 6500+
Matrix Male CD-1 mouse plasma (EDTA-K2)
Analyte(s): Compound 1
Internal standard(s): 100 ng/mL Labetalol & 100 ng/mL Tolbutamide in ACN
MS conditions ESI: positive
SRM detection
Compound 1: [M+H]+m/z 979.8>798.4
Labelatol (IS): [M+H]+m/z 329.2>162.1
UPLC conditions
Mobile Phase A: 0.1% FA in Water
Mobile Phase B: 0.1% FA in ACN

| Time (min) | Mobile Phase B (%) |
|---|---|
| 1.10 | 98 |
| 1.50 | 98 |
| 1.51 | 15 |
| 2.10 | Stop |

Column: Waters ACQUITY UPLC HSS T3 1.8 μm 2.1×50 mm
Flow rate: 0.6000 mL/min
Retention time: Labelatol (IS): 0.998 min
Sample preparation:
An aliquot of 24 μL sample was protein precipitated with 120 μL IS solution (100 ng/mL Labetalol & 100 ng/mL Tolbutamide in ACN), the mixture was vortex-mixed well and centrifuged at 3900 rpm for 10 min, 4° C. An aliquot of 90 μL supernatant was transferred to sample plate and mixed with 60 μL water, then the plate was shaken at 800 rpm for 10 min, 15.0 μL supernatant was injected for LC-MS/MS analysis.
Calibration curve:
1.00-3000 ng/ml, for Compound 1 in female CD-1 mouse plasma (EDTA-K2)

Figure 3:
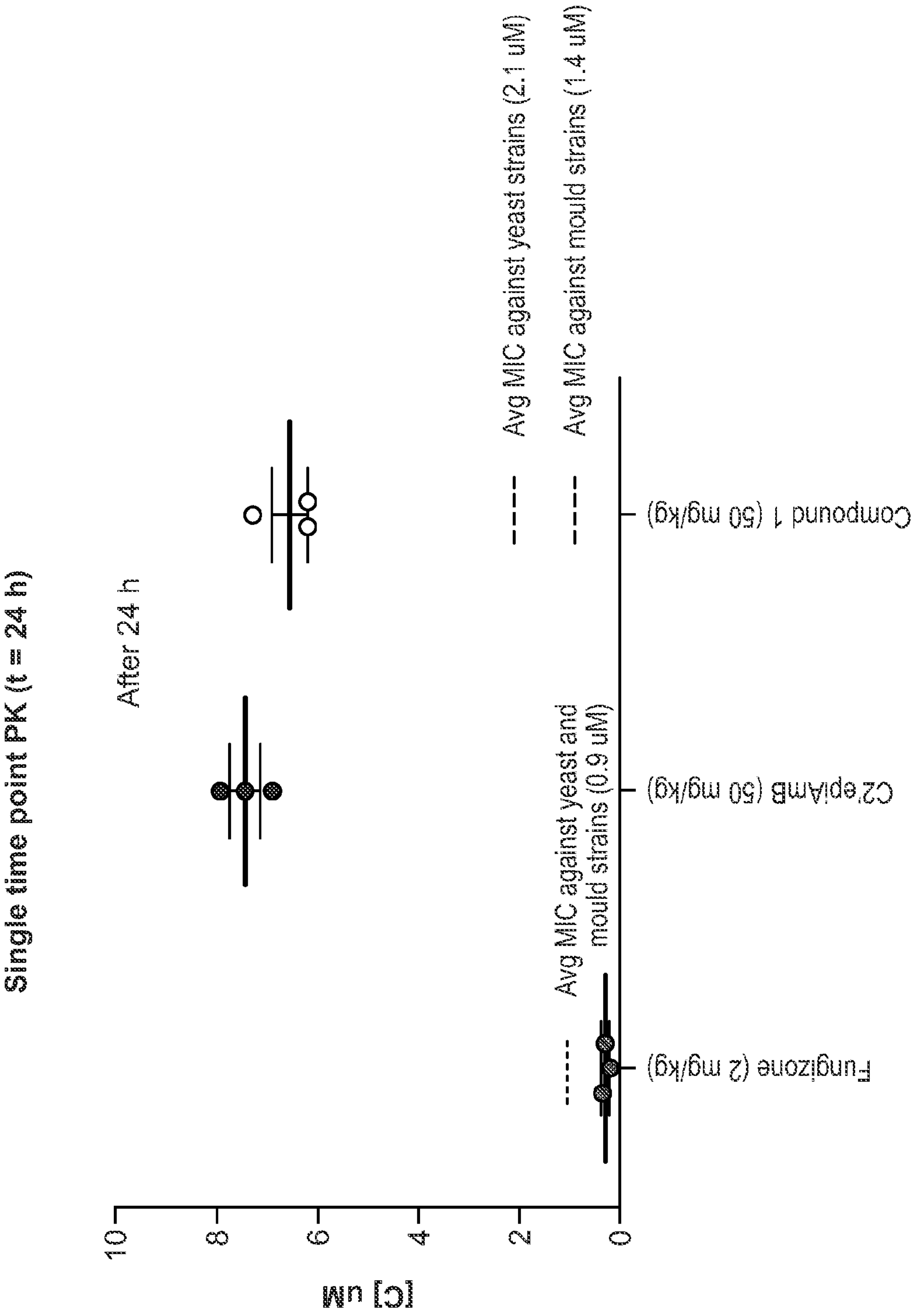
FIG. 3 depicts serum concentrations of Compound 1 following high-dose administration.

Additional Mouse PK Experiments (FIG. 3): The blood samples were collected from the mice treated with the compound for Invivo Toxicity experiment (vide supra) after 24 h. To 50 μL of mice serum, 300 μL, of HPLC-grade methanol was added. The mixture was well mixed by vortex 30 s. To allow full extraction of AmB (or derivative) and precipitation of proteins, the mixture was allowed to sit at room temperature for 0.5 h. The mixture was then centrifuged at 16000 g for 10 min and the unfiltered supernatant was used for HPLC analysis. (Note—AmB binds to pre-filters). The concentration of AmB (or derivatives) was calculated through pre-established standard curve.

Standard Curve was Made by the Following Steps:
1: making series of different concentration (10, 20, 40, 80 100, 200, 400, 1000 μM, determined by UV-vis, extinction co-efficient at 406 nm: 164 $mM^{-1}$) of AmB (or derivative) solution in methanol,
2: inject 10 μL of the standard solution into HPLC, the area under the curve and its corresponding concentration was used to establish the standard curve.

HPLC Method:
C18 SiO2 column: Sunfire column, 5 μM, 15 cm;
aqueous buffer (A): filtered 0.1% Formic Acid in MQ water
organic solvent (B): filtered HPLC grade Acetonitrile
Flow rate: 1 mL/min, DAD: 406.4 nm, ionization method: AJS ESI, positive mode
gradient change: 95:5 (0.1% Formic acid in water: MeCN) to 5:95 (01% Formic acid in water: MeCN) in 8 mins, gradient change time table as below
0 min 95% A, 5% B
0.5 min 95% A, 5% B
8.5 min 5% A, 95% B
9.5 min 5% A, 95% B
10.5 ruin 95% A, 5%, B

Example 7. Solubility of Disclosed Compounds

Test Article 1: Synthesized in lab (purity>95%)
D5W:Braun USA (Product No:L5101)
Instrument Details:
Sonicator: Branson Ulrasonics 2800; Vortex-Genie 2 lab mixer
UV-Vis: Thermo Fisher Nanodrop oneC
Steps*:
Take 6 mg of sample (measured by UV-Vis) in a clean oven-dried 7 mL vial
Add 1.65 mL sterile D5W (at room temperature)
Vortex it for 2 min.
Water bath sonication: 2 min×2
Repeat step 3 and 4 until the solution is clear
Transferred in a 2 mL Eppendorf tube and centrifuged (3000 g×2 min) to ensure compound is dissolved completely and there is no insoluble part. (optional step)
Concentration measured by UV (abs at 406 nm) (optional step)
Amounts are Based on the Solution Prepared for 50 mg/kg Dosage Invivo Toxicity Experiment

TABLE 5

Solubility of Disclosed Compounds and AmB in D5W

| | AmB | Compound 1 | Compound 2 |
|---|---|---|---|
| Solubility (mM) | 0.023 | >7.22 | 0.366 |
| Fold of Increase w.r.t. AmB | — | >314 | 15.9 |

Figure 6:
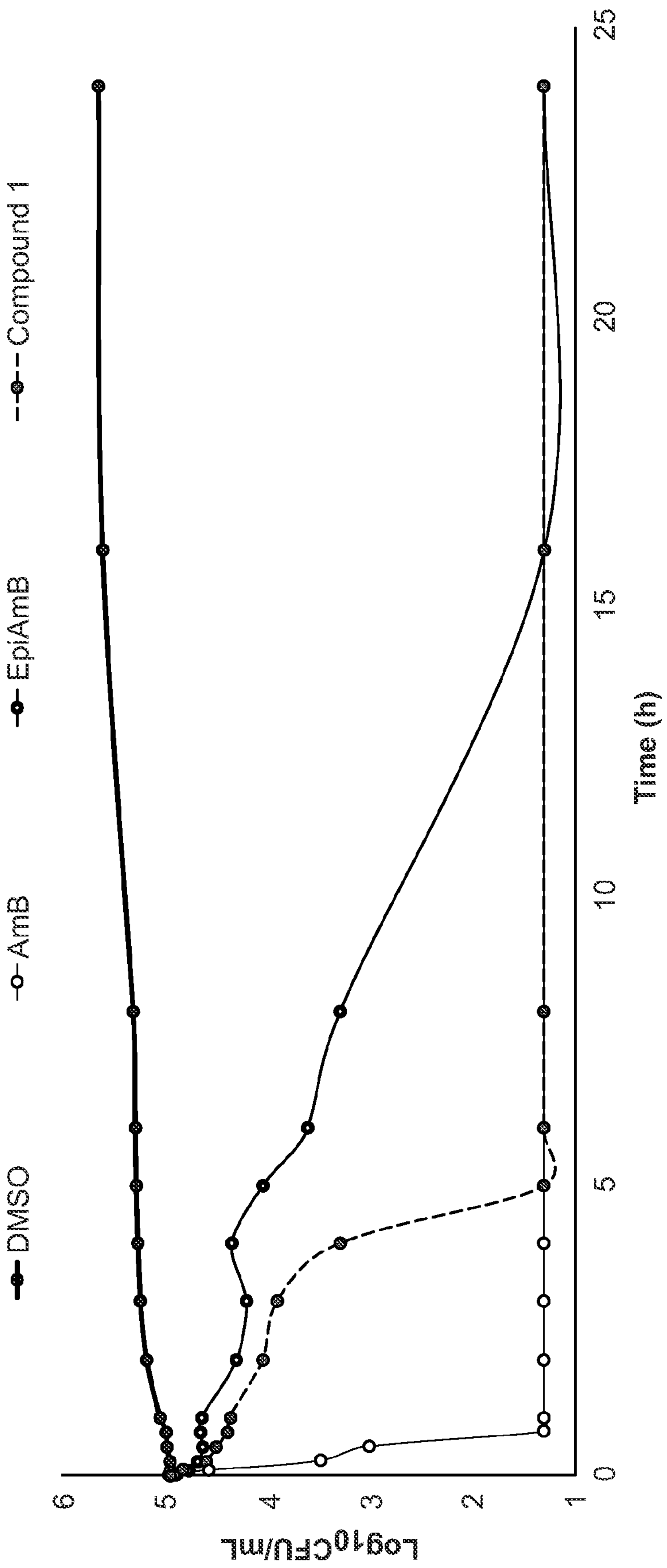
FIG. 6 depicts results of a killing kinetics assay with *Candida albicans* using DMSO, AmB, EpiAmB (C2'epiAmB), and Compound 1.

Example 8. Killing Kinetics Assay with *Candida albicans*: (FIG. 6)

The protocol for the killing kinetics assay was adapted from CLSI protocol for MIC measurement. From back stock, fungal colonies were suspended in 0.9% sterile saline solution and diluted to ≈103 inoculum density. A 10 ul aliquot was and plated on Sabouraud Dextrose Agar (SDA) plates using L-spreader and incubated for 24-48 h at 35° C.: and the colony growth was monitored. During the experiment, 2-3 single colonies were suspended in 10 mL RPMI 1640 media (prepared following CLSI protocol) and the cell density was measured using hemacytometer. The inoculum density was then adjusted to ≈105 cfu/mL. In a sterile Eppendorf tube (1.7 mL-2 mL), 990 μL of inoculum aliquot was mixed with 10 μL of 100X solution of the compound (solution prepared in DMSO and DMSO content in each test solution is 1%). A control sample was prepared to confirm the viability using only 1% DMSO in RPMI 1640 media. At predetermined time points (0, 0.25, 0.5, 0.75, 1, 2, 3, 4, 5, 6, 8, 10, 16 and 24 h), a 10 μL sample was removed from each tube and serially diluted 10-fold with RPMI 1640 media, and a 10 μL aliquot was plated onto a SDA plate for colony count determination. When colony counts were expected to be less than 1,000 CFU/mL, a 50 μL aliquot was taken and half diluted in RPMI 1640 media, and a 50 μL was plated onto a SDA plate. Plates were incubated at 35° C. for 24 to 48 hours prior to examination. All experiments were conducted in triplicate.

Example 9, In Vivo Efficacy in Murine Candidiasis Model (*C. albicans* SN250): (FIGS. 7 and 8)

Figure 7:
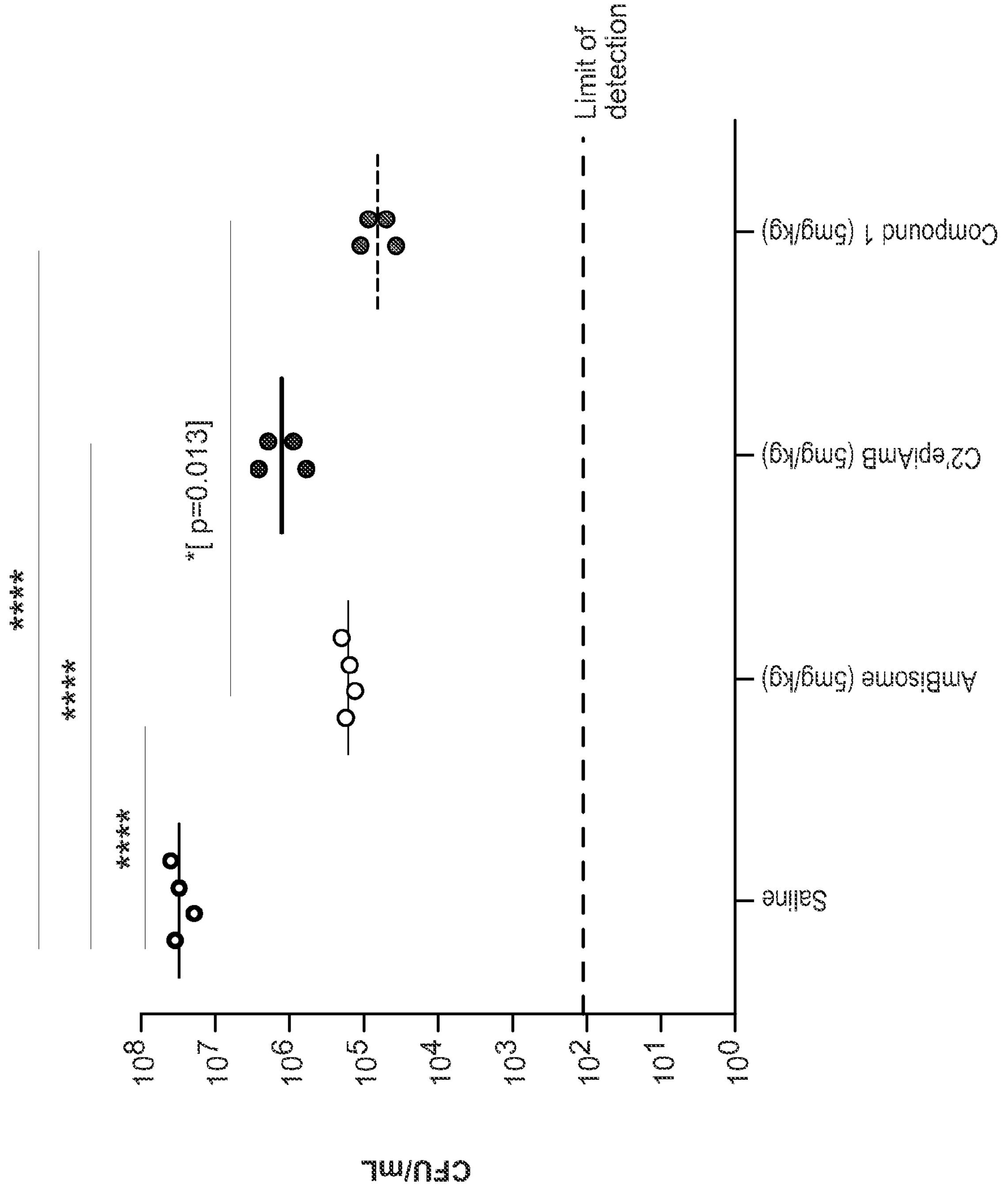
FIG. 7 depicts differences in CFU for *C. albicans* for mice treated with different dosages of Compound 1 compared to saline and AmB; *=p<0.05; ****=p<0.001.

FIG. 7: Based on the number of different test candidates and different doses, female CD-1 mice (avg. body weight=27 g) were divided into groups where each group was consisting of 4 mice.

Before treatment all the groups were inoculated with *C. albicans* SN250 via tail vain (≈105 CFU/mL). After 2 hours of inoculation, groups were treated with single dose IV formulation of the test article (in saline). After 24 h of incubation, animals were euthanized and the kidneys were harvested and homogenized immediately. In order to measure the fungal burden 24 h post treatment serum was plated and the density of colonies (CFU/mL) was calculated. In this experiment AmBisome and C2'epiAmB were used as controls and the teat article Compound 1 was administered at 5 mg/kg dose, similar to the control.

Figure 8:
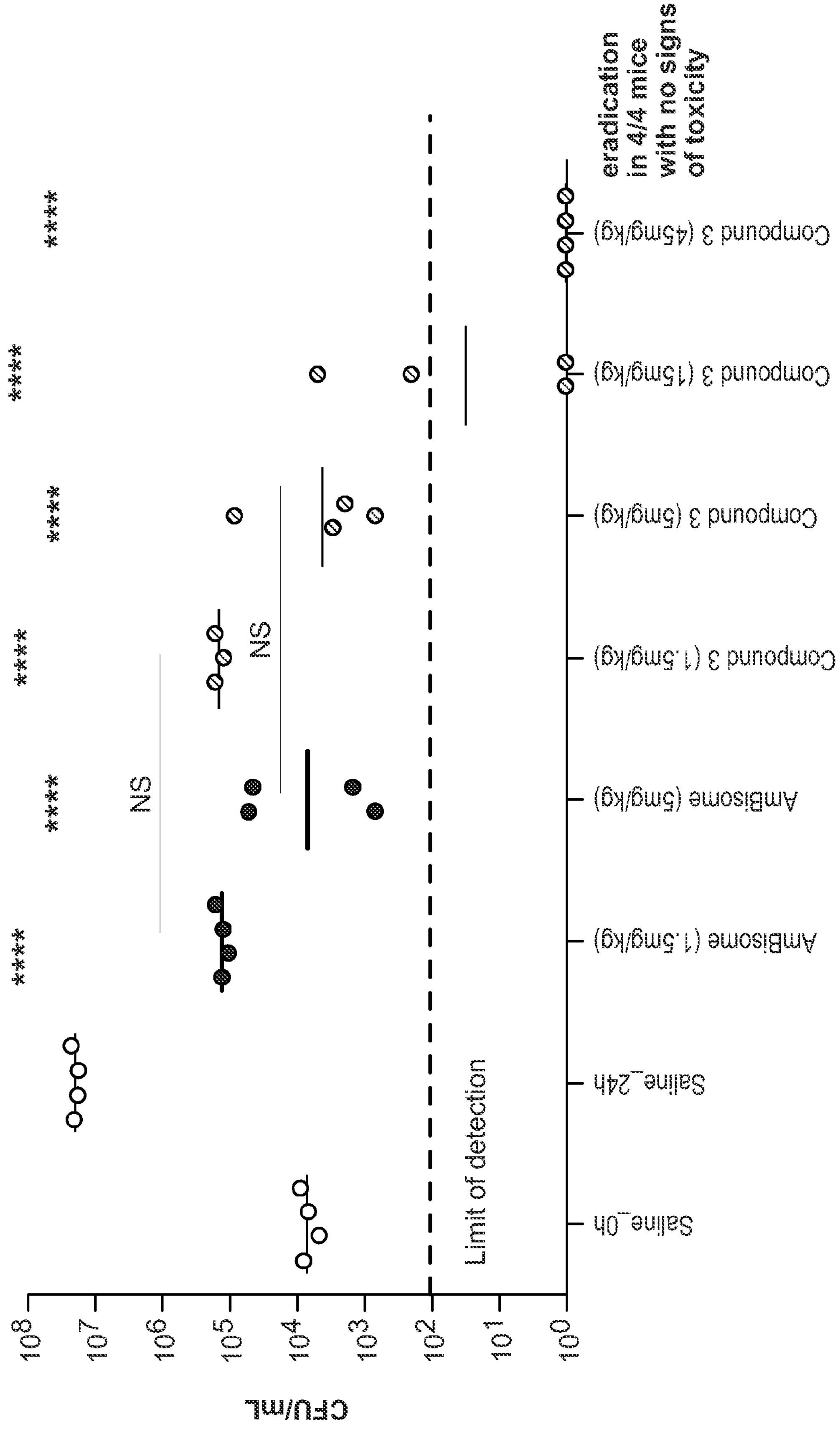
FIG. 8 depicts differences in CFU for *C. albicans* for mice treated with different dosages of Compound 3 compared to saline and AmB; NS=not significant (p>0.05); ****=p<0.001.

FIG. 8: In order to test the efficacy of the higher dose of Compound 1, we developed the acetate salt version of the drug, which was found to highly soluble in aqueous solutions, especially in D5W and saline vehicles. Hence, we went ahead and repeated the aforementioned in vivo studies and tested the efficacy of the drug candidate Compound 3 at four different single doses 1.5 mg/kg; 5 mg/kg; 15 mg/kg and 45 mg/kg. Post experiment the fungal burdens were measured using the procedure mentioned above, in this study were able to show that high dose eradication of fungal infection is possible using non-toxic Compound 3.

Figure 9:
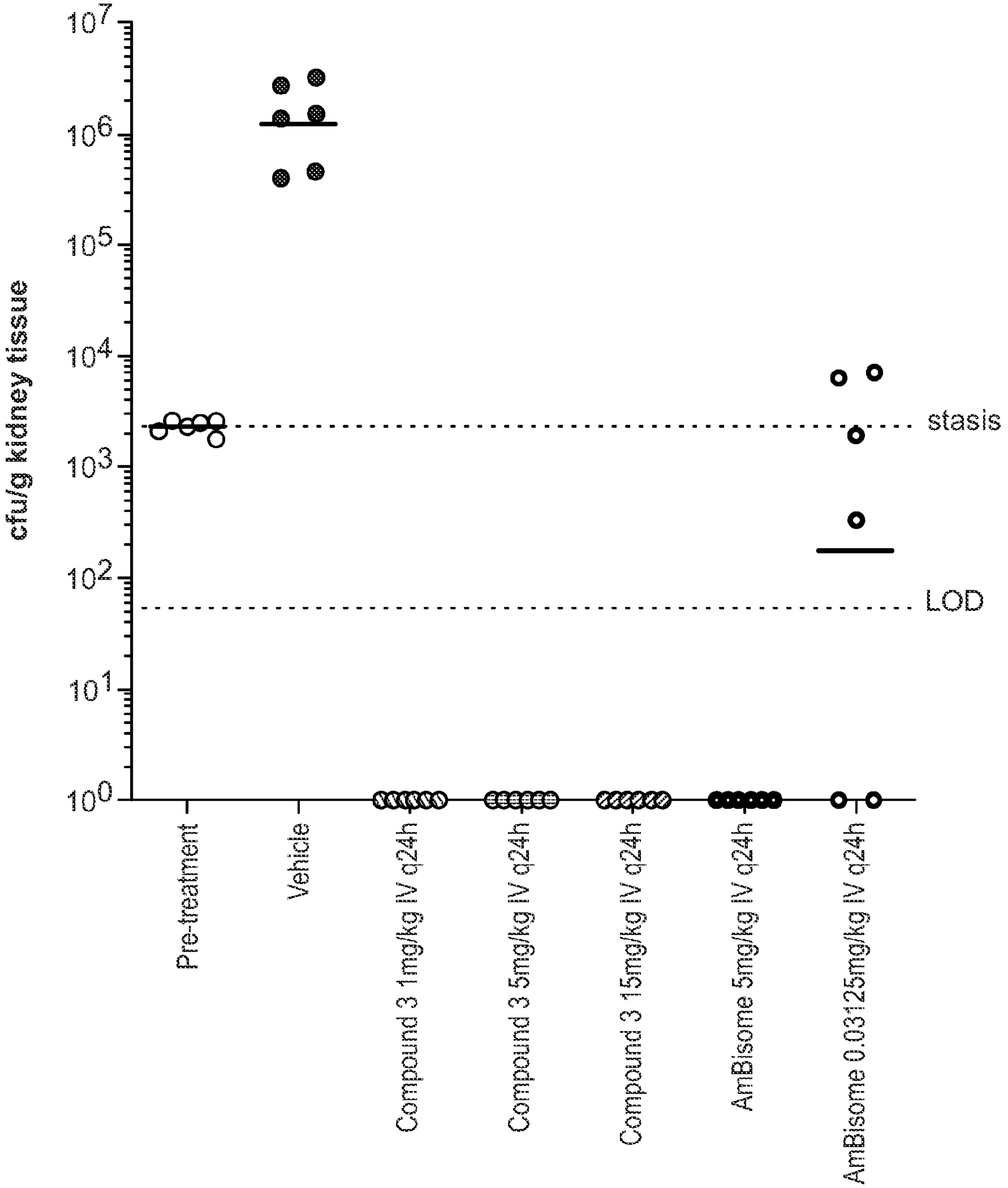
FIG. 9 depicts differences in CFU for invasive candidiasis for mice treated with different dosages of Compound 3 compared to saline and AmB; Direct-Kruskal-Wallis test w.r.t vehicle_24 h unless otherwise indicated: NS=Not Significant (p>0.05); p<0.01*p<0.005, ****p<0.001

Example 10. In Vivo Efficacy in Murine Candidiasis Model (*C. albicans* SC5314): (FIG. 9)

In this study, efficacy and tolerance of Compound 3 in a multiple dose regimen were investigated against *C. albicans* SC5314 in male ICR mice. Three different doses of Compound 3 were tested 1 mg/kg; 5 mg/kg and 15 mg/kg over 7 days as daily single dose. The body weights were also recorded on daily basis. Two different doses of Ambisome were used as controls. Each group were consisting of 6 mice. Before treatment all the groups were inoculated with *C. albicans* SC5314 via tail vain (≈1.9×105 CFU/mL). After 5 hours of inoculation, groups were given the first IV dose (in D5W). After completion of 7 days treatment all mice were sacrificed and the fungal burden in kidney was measured using plating technique. Boy weights are shown in FIGS. 22A and 22B.

Figure 10:
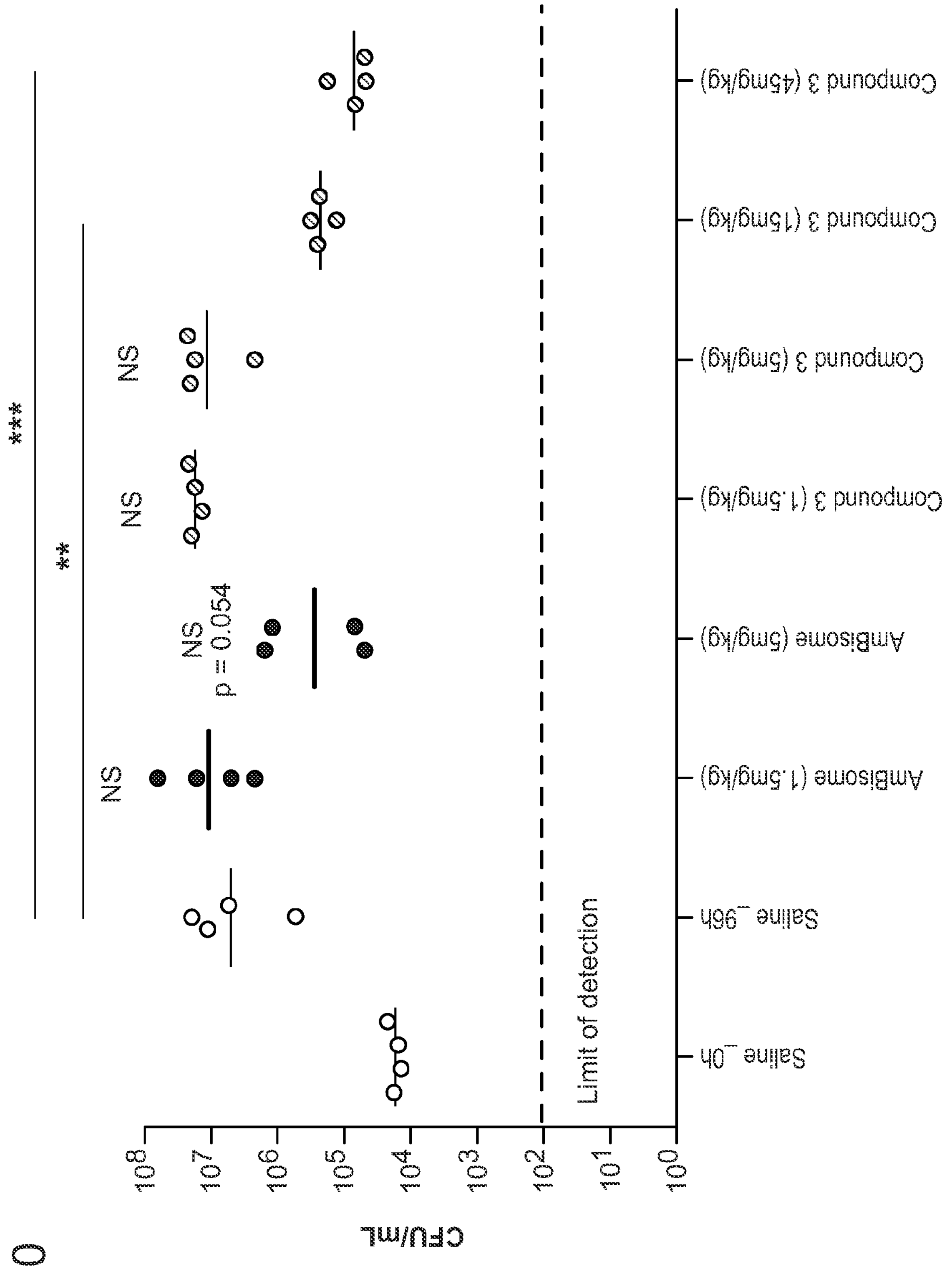
FIG. 10 depicts differences in CFU for *C. auris* for mice treated with different dosages of Compound 3 compared to saline and AmB; NS=not significant (p>0.05); =p<0.01; *=p<0.005.

Example 11. In Vivo Efficacy in Murine Candidiasis Model (*C. auris*): (FIG. 10)

Based on the number of different test candidates and different doses, female CD-1 mice (avg. body weight=27 g) were divided into groups where each group was consisting of 4 mice. Before treatment all the groups were inoculated with *C. auris* via tail vain (≈105 CFU/mL). After 2 hours of inoculation, groups were given first IP dose of Compound 3 (in saline). Over next four days multiple doses were given at 24 h, 48 h and 72 h post inoculation. After 4 days of treatments, all animals were euthanized and the kidneys were harvested and homogenized immediately. In order to measure the fungal burden 24 h post treatment serum was plated the and density of colonies (CFU/mL) was calculated. In this experiment two different doses of AmBisome and were used as controls and the test article Compound 3 was administered at 1.5, 5, 15 and 45 mg/kg dose.

Figure 11:
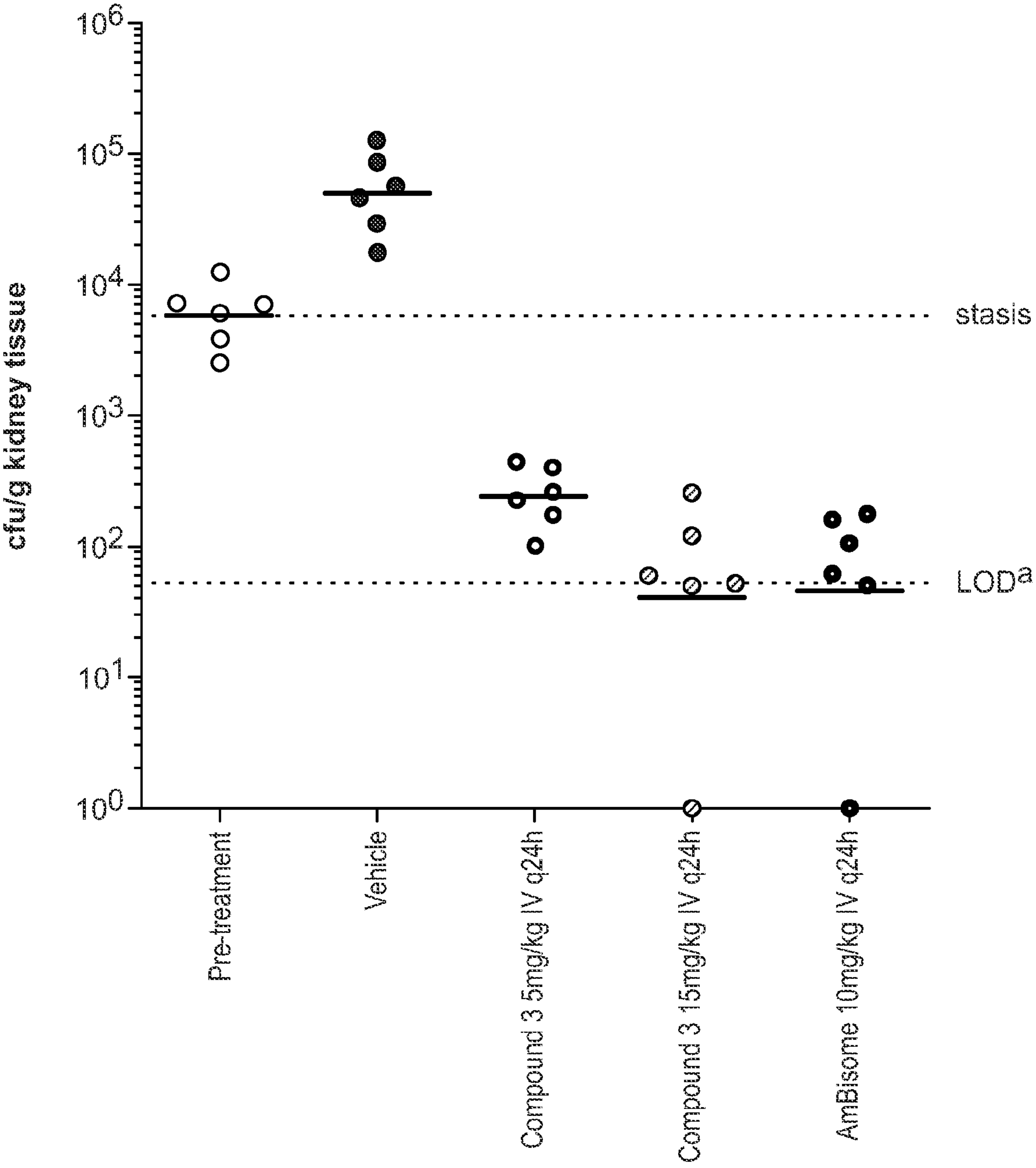
FIG. 11 depicts differences in CFU for *Aspergillus fumigatus* for mice treated with different dosages of Compound 3 compared to saline and AmB; Direct-Kruskal-Wallis test w.r.t vehicle_24 h unless otherwise indicated: NS=Not Significant (p>0.05); p<0.01*p<0.005, ****p<0.001
Figure 12A:
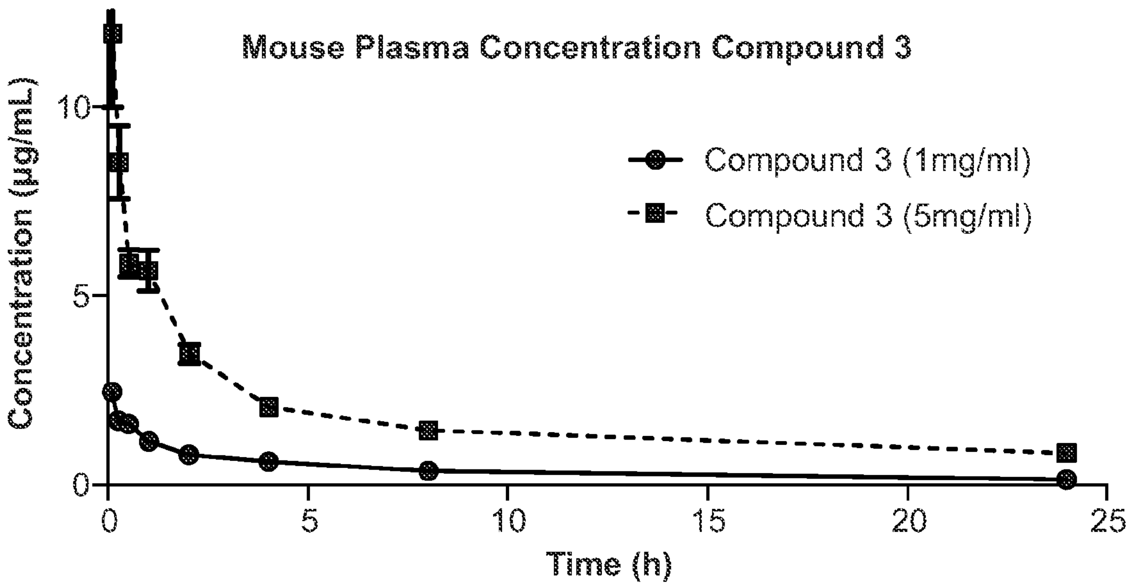
FIG. 12A depicts blood plasma concentrations of Compound 3 in mice.
Figure 12B:
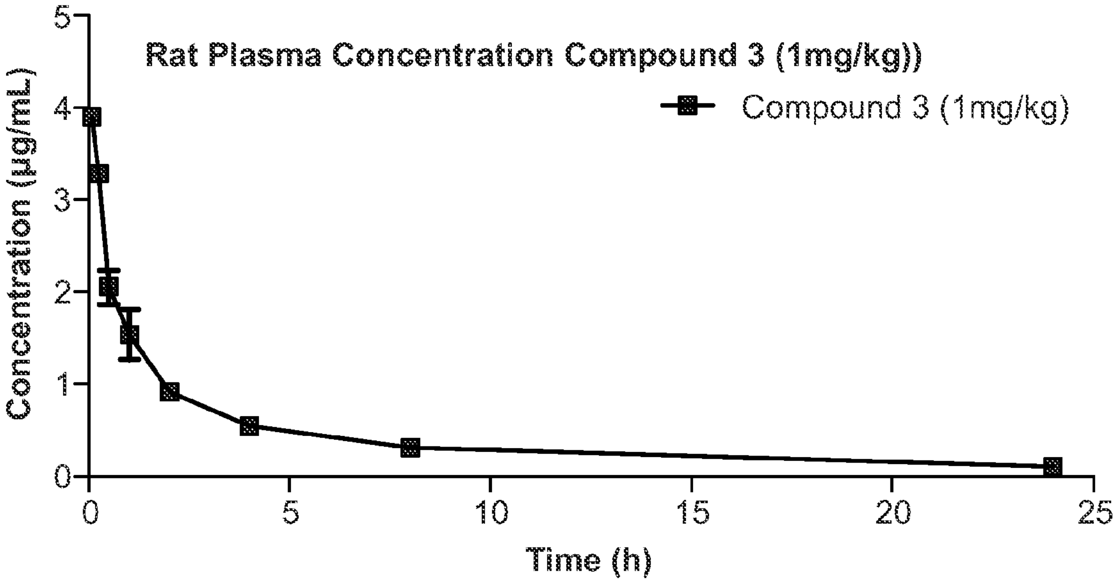
FIG. 12B depicts blood plasma concentrations of Compound 3 in rats.
Figure 12C:
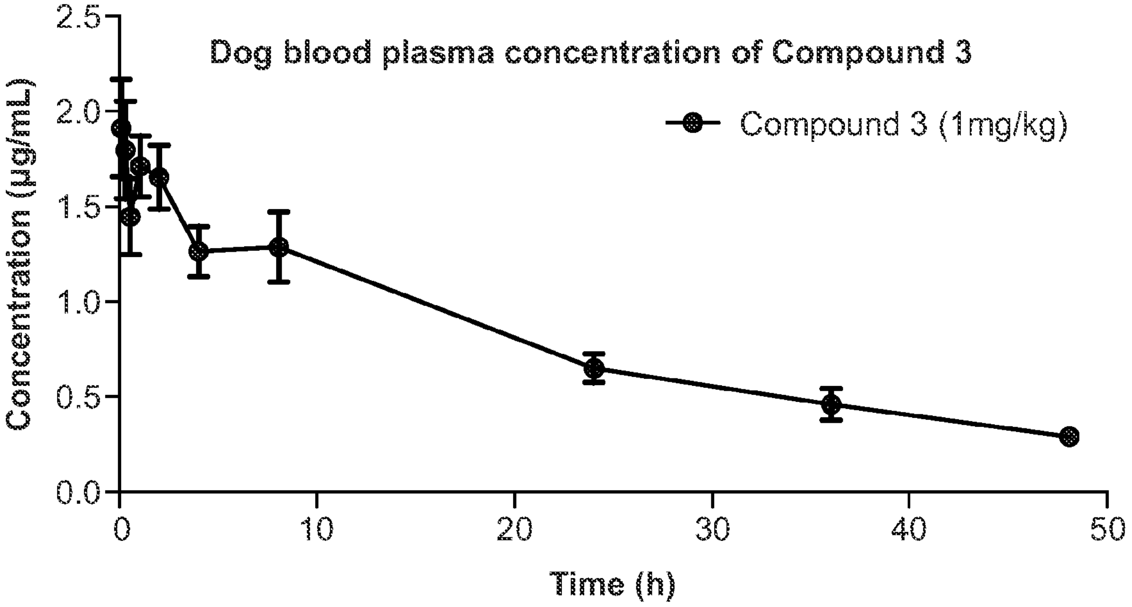
FIG. 12C depicts blood plasma concentrations of Compound 3 in dogs.
Figure 12D:
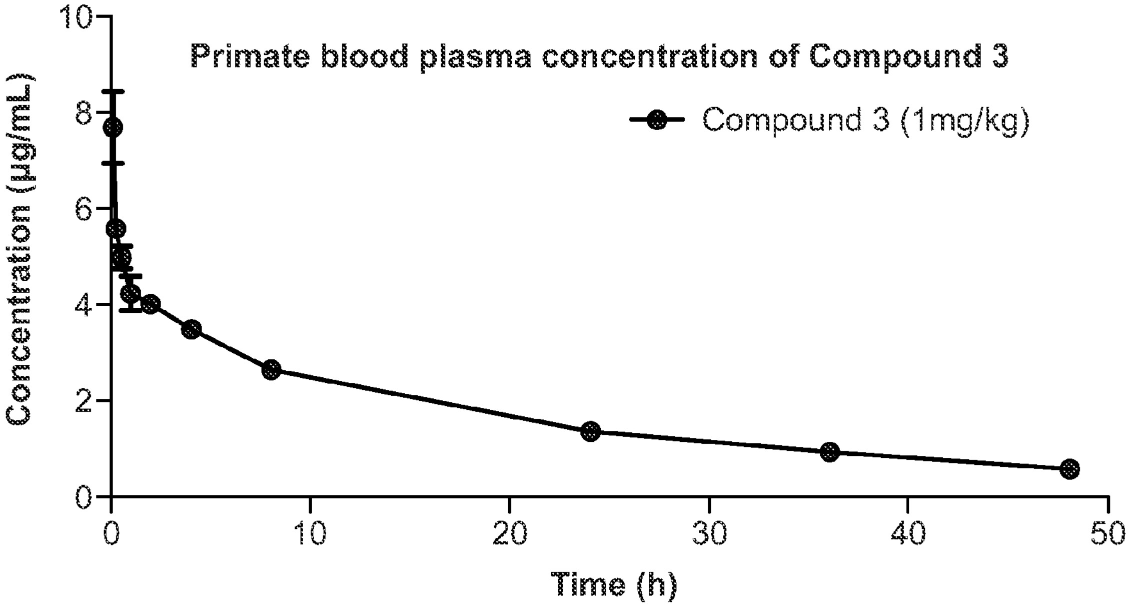
FIG. 12D depicts blood plasma concentrations of Compound 3 in primates.

Example 12. In Vivo Efficacy in Murine Aspergillosis Model: (FIG. 11)

In this study, efficacy and tolerance of Compound 3 in a multiple dose regimen were investigated against *Aspergillus fumigatus* 1163 in male ICR mice. Two different doses of Compound 3 were tested 5 mg/kg and 15 mg/kg over 4 days as daily single dose. The body weights were also recorded on daily basis. Ambisome (10 mg/kg) were used as control in this experiment. Each group were consisting of 6 mice. Three days before the study, all mice were treated with cyclophosphamide (200 mg/kg) as immunosuppressant. On the day of the study all the groups were inoculated with *Aspergillus fumigatus* 1163 via tail vain (≈2.9×105 CFU/mL). After 5 hours of inoculation, groups were given the first IV dose (in D5W). After completion of 4 days treatment all mice were sacrificed and the fungal burden in kidney was measured using plating technique. Body weights are available on Slide 17.

Figure 13:
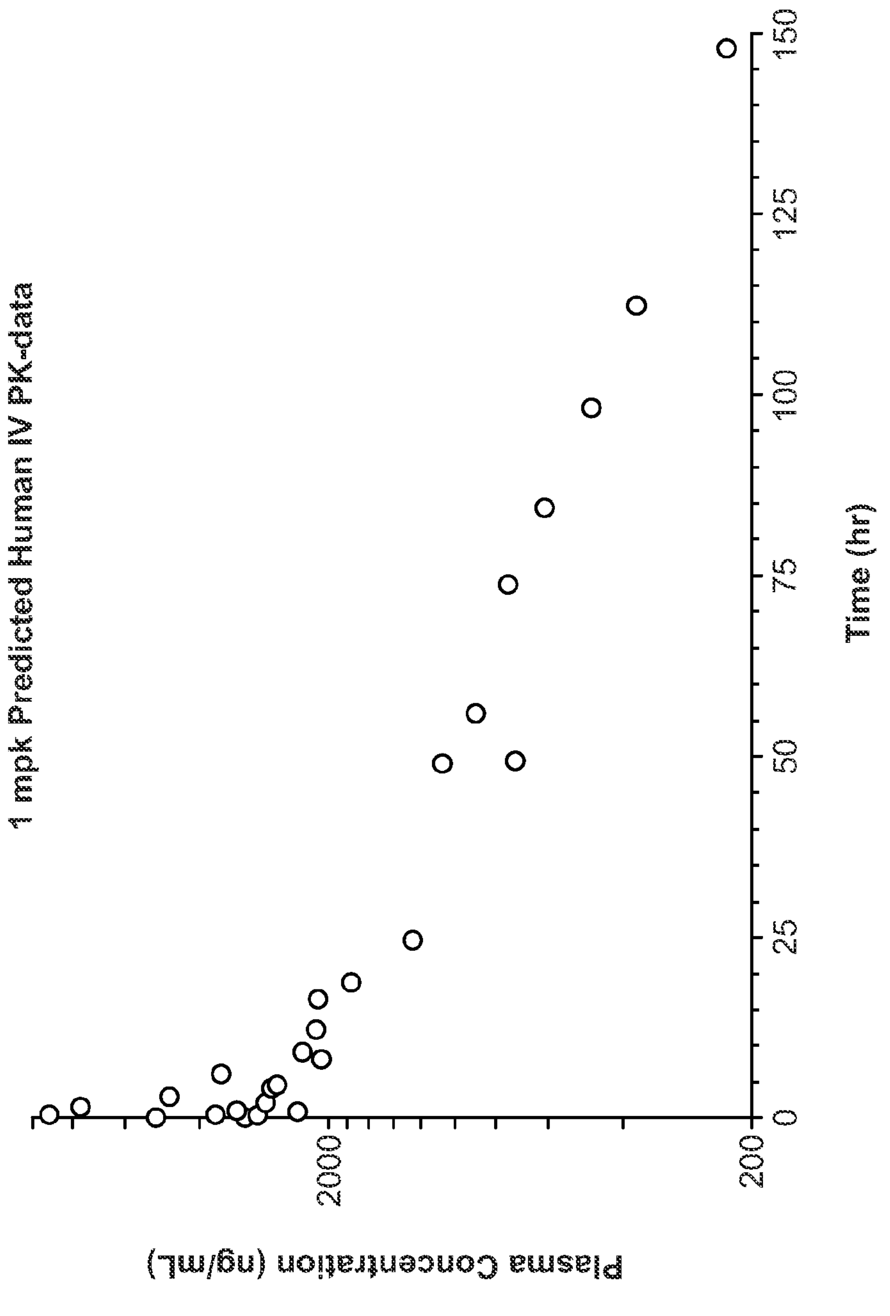
FIG. 13 depicts Wajima superposition to predict human concentration-time profile for Compound 3.
Figure 14:
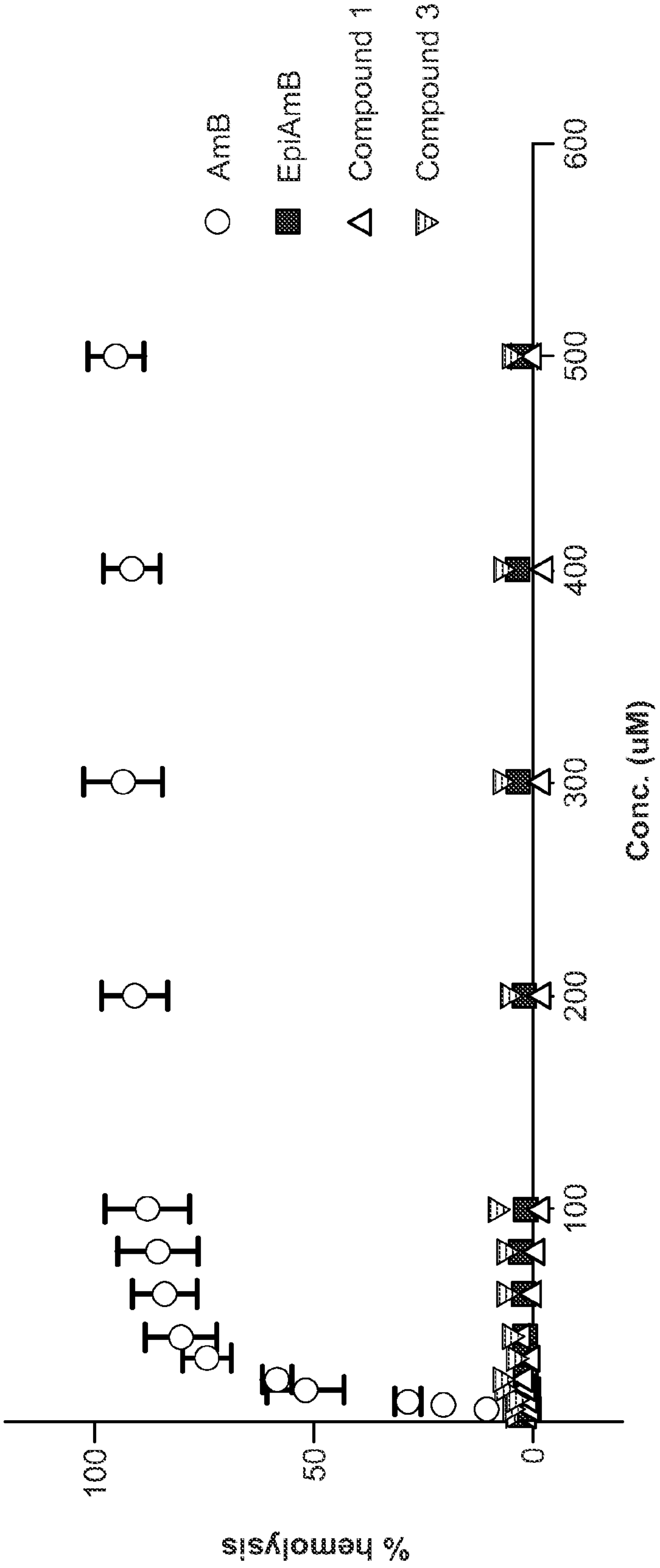
FIG. 14 depicts the percent hemolysis for Compound 1 and Compound 3.

Example 13. Wajima Superposition: (FIGS. 12 and 13)

The prediction of human DMPK using Wajima superposition was done using standard protocol.

| PK Parameter | Rat | Dog | Monkey | Human |
|---|---|---|---|---|
| $CL_p$ (mL/min/kg) | 1.56 | 0.365 | 0.169 | NA |
| $V_{ss}$ (L/kg) | 0.873 | 0.615 | 0.249 | NA |
| Plasma protein binding ($f_{u,p}$) | 0.0406 | 0.0364 | 0.0273 | 0.0445 |
| Blood:plasma | 0.757 | 0.753 | 0.751 | 0.597 |

| NCA Parameter | Value |
|---|---|
| $CL_p$ (mL/min/kg) | 0.11 |
| $V_{ss}$ (L/kg) | 0.39 |
| $t_{1/2}$ (α) (hrs) | 3.8 |
| $t_{1/2}$ (β) (hrs) | 44 |
| $AUC_{0-t}$ (μg br/mL) | 139.3 |
| $AUC_{0-24}$ (μg hr/ml) | 60.8 |
| $C_0$ (μg/mL) | 3.85 |

Human PK:

| | PK Parameter (plasma) | | | |
|---|---|---|---|---|
| | Observed Parameters Am Bisome, 2 mg/kg* | | Predicted Parameters AM-2-19, 2 mg/kg** | |
| | Cmax or C0 (μg/mL) | | | |
| | Cmax = 22.9 (2-hr infusion) | | C0 = 7.70 (bolus) | |
| | AUC0-24 (μg hr/mL) | | | |
| | 171 ± 126 | | 122 | |
| PK Parameter | Am Bisome | | Compound 3 | |
| Dose (mg/kg) | 1 | 5 | 1 | 5 |
| $CL_p$ (mL/min/kg) | 1.6 | 0.71 | 1.4 | 1.4 |
| $V_{ss}$ (L/kg) | 0.78 | 0.37 | 1.1 | 1.5 |
| $t_{1/2}$ (hrs) | 5.7 | 5.7 | 9.3 | 13.7 |
| $C_0$ (μg/mL) | 5.6 | 14.7 | 3.0 | 14.2 |
| $AUC_{0-24}$ (μg hr/mL) | 20.5 | 114 | 9.7 | 42.2 |

*From Antimicrobial Agents Chemother. 2002, 46(3): 828-833
**Assuming dose proportionality Mouse PK, IV bolus (female CD-1):

| PK Parameter | Am Bisome | | Compound 3 | |
|---|---|---|---|---|
| Dose (mg/kg) | 1 | 5 | 1 | 5 |
| $CL_p$ (mL/min/kg) | 1.6 | 0.71 | 1.4 | 1.4 |
| $V_{ss}$ (L/kg) | 0.78 | 0.37 | 1.1 | 1.5 |
| $t_{1/2}$ (hrs) | 5.7 | 5.7 | 9.3 | 13.7 |
| $C_0$ (μg/mL) | 5.6 | 14.7 | 3.0 | 14.2 |
| $AUC_{0-24}$ (μg hr/mL) | 20.5 | 114 | 9.7 | 42.2 |

Figure 15A:
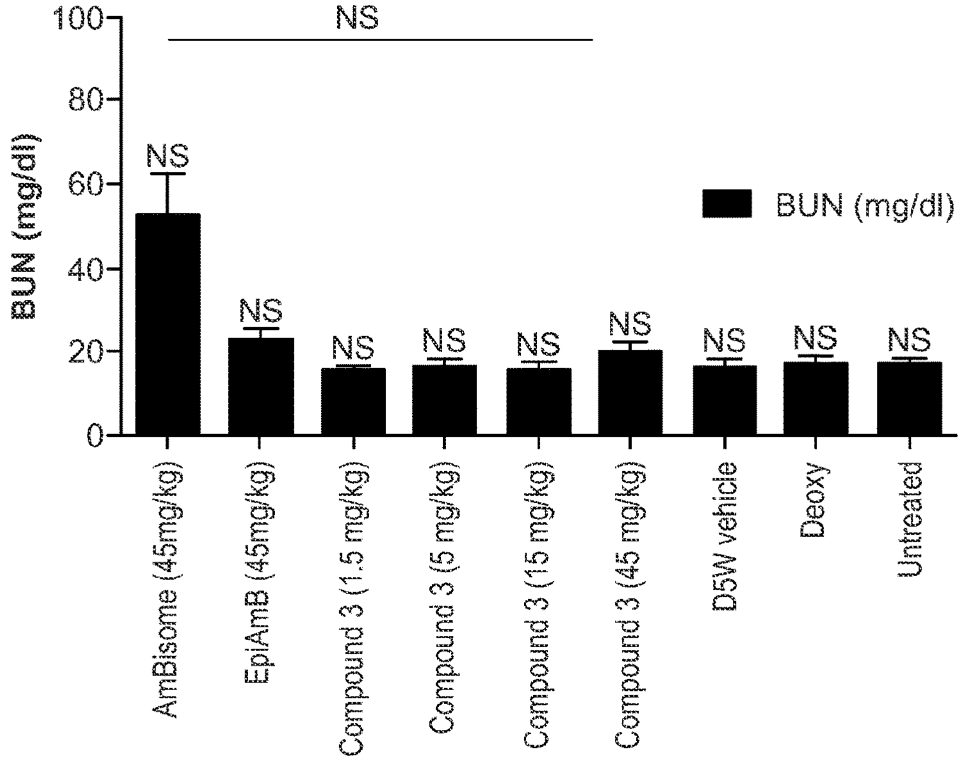
FIG. 15A depicts BUN levels following administration of Compound 3.
Figure 15B:
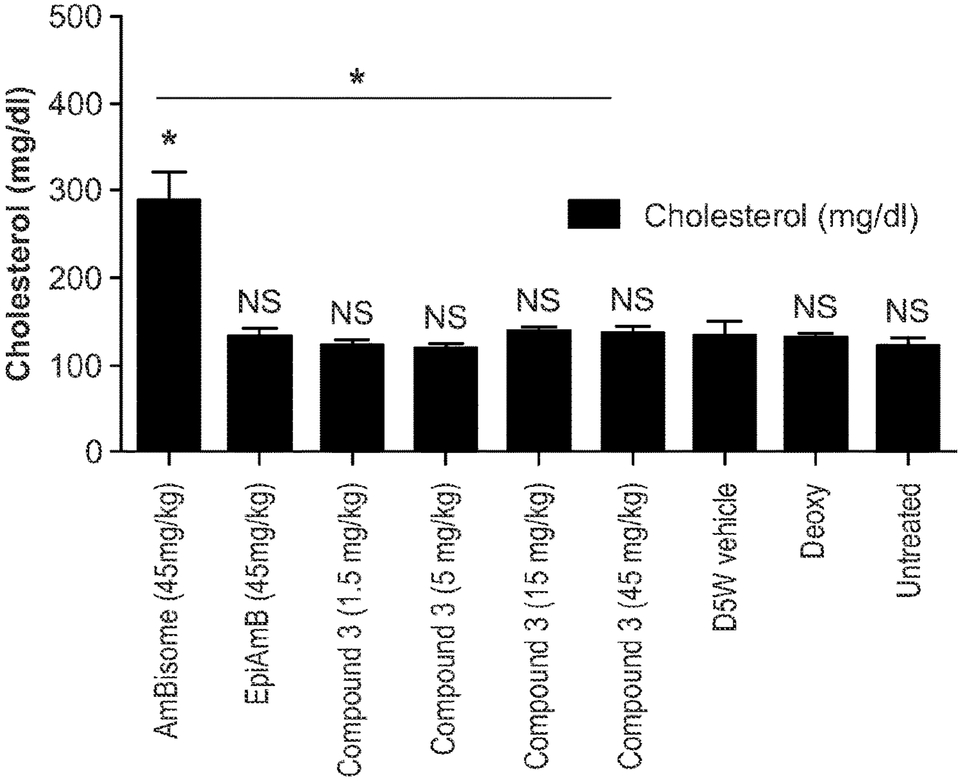
FIG. 15B depicts cholesterol levels following administration of Compound 3.
Figure 15C:
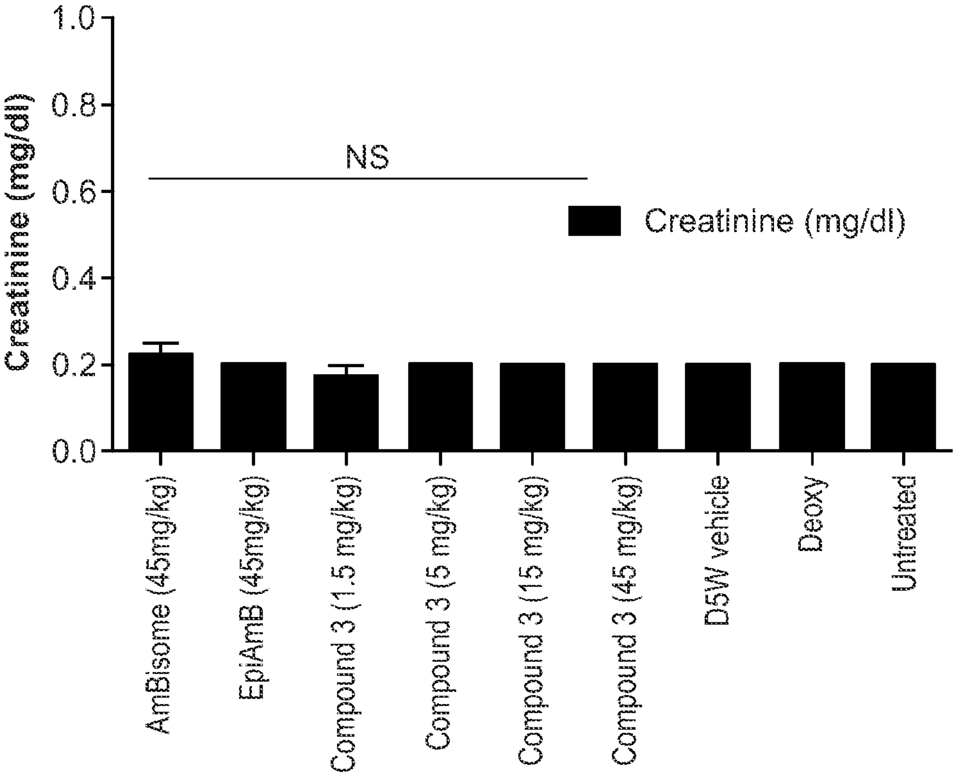
FIG. 15C depicts creatinine levels following administration of Compound 3.
Figure 16:
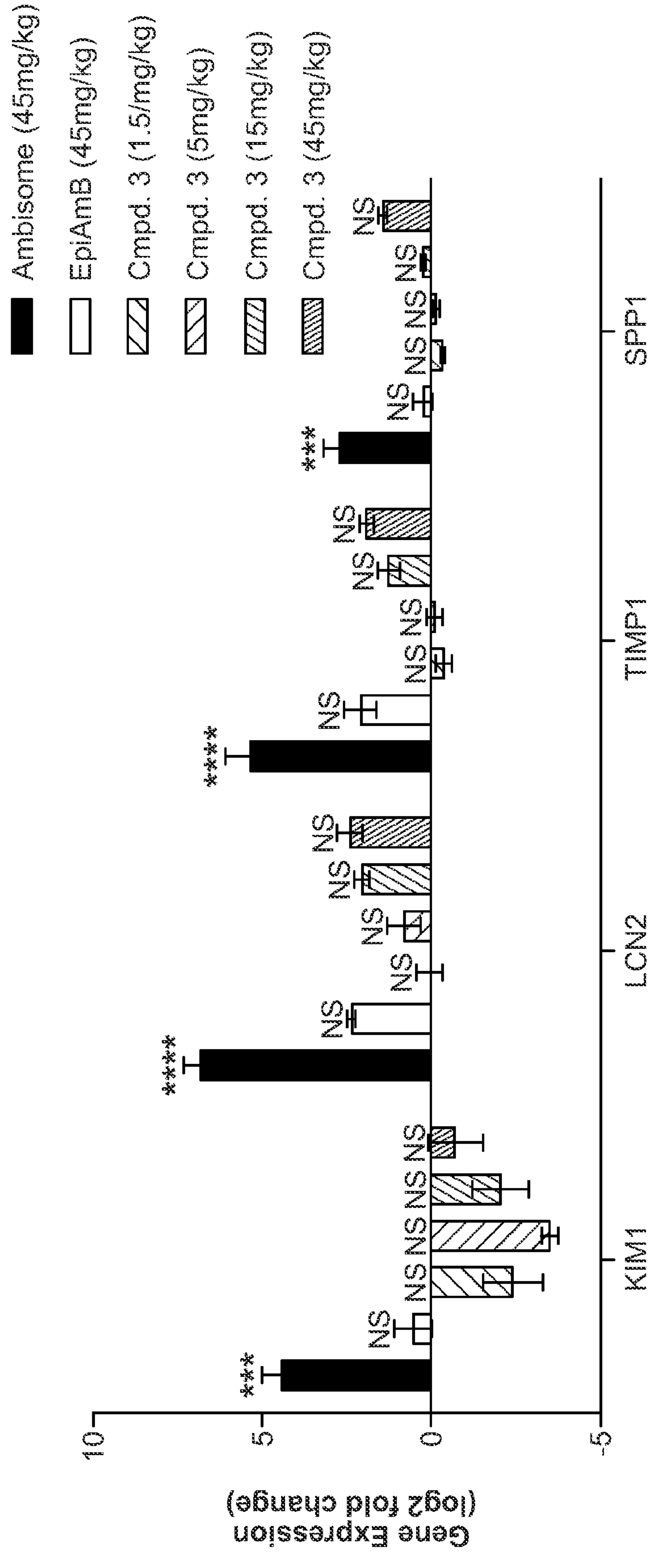
FIG. 16 depicts gene expression changes following administration of Compound 3.
Figure 17A:
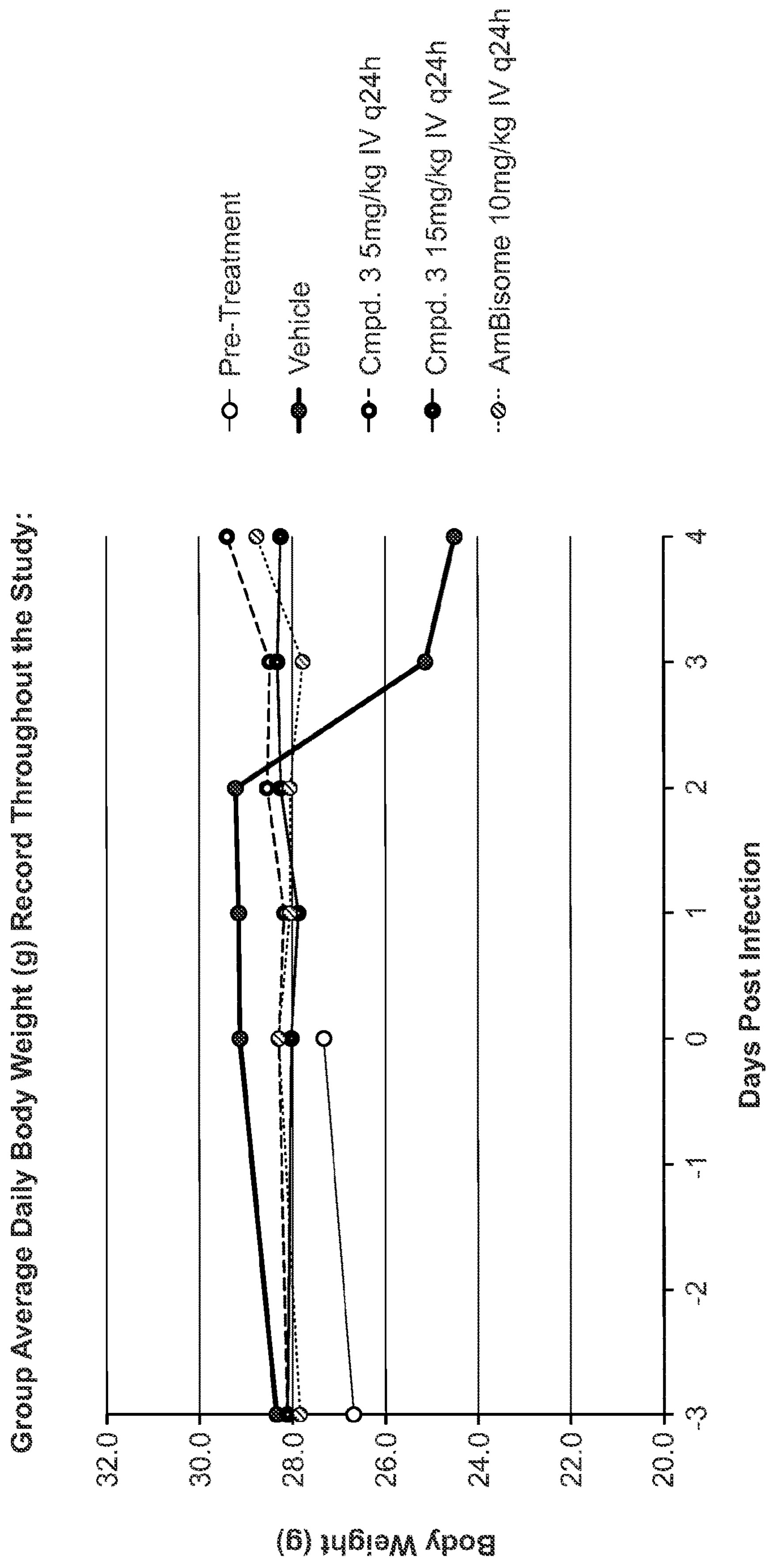
FIG. 17A depicts group average daily body weight for mice inoculated with *Aspergillus fumigatus* and treated with saline, compound 3, or AmB.
Figure 17B:
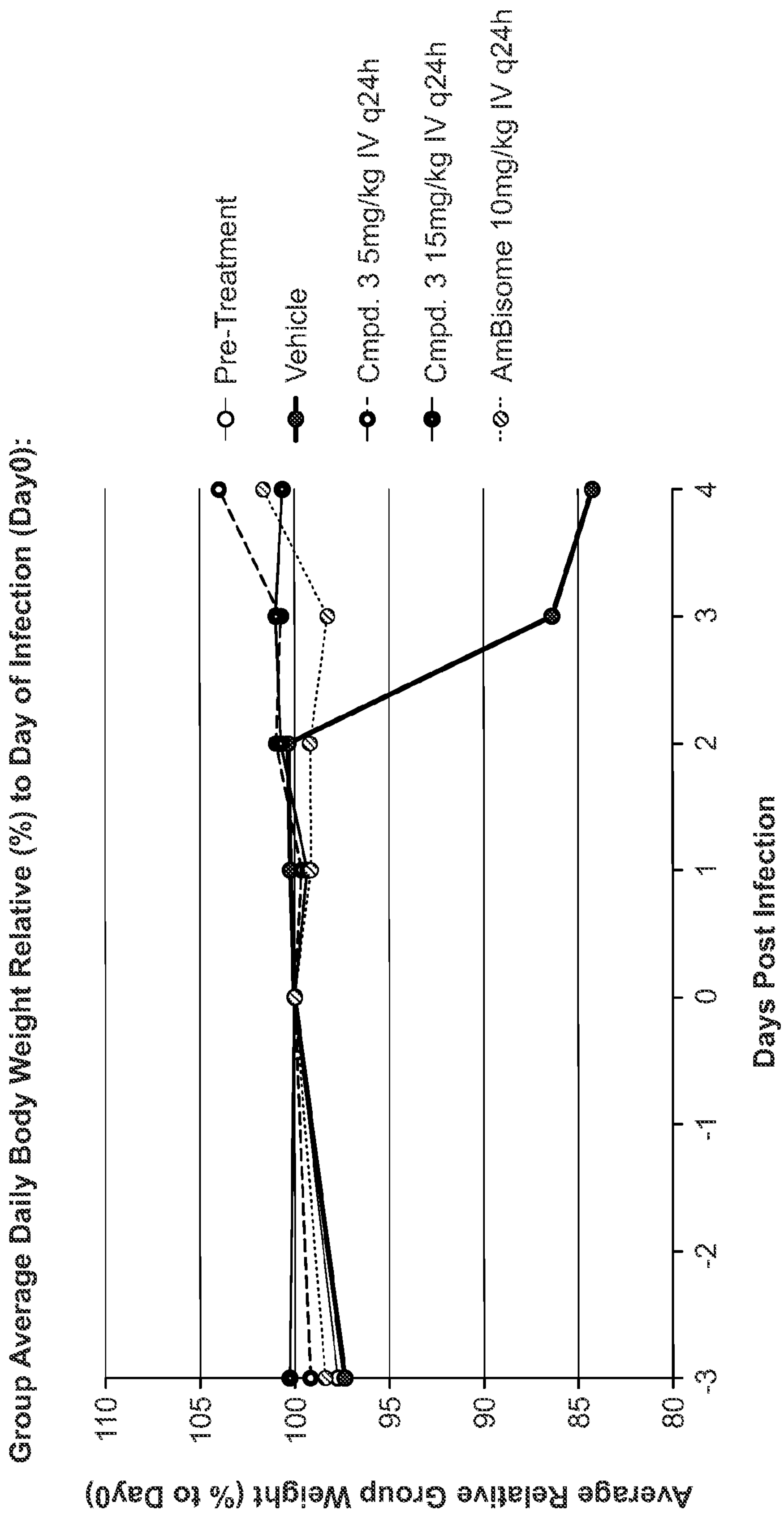
FIG. 17B depicts group average daily body weight relative to day of infection for mice inoculated with *Aspergillus fumigatus* and treated with saline, compound 3, or AmB.
Figure 18A:
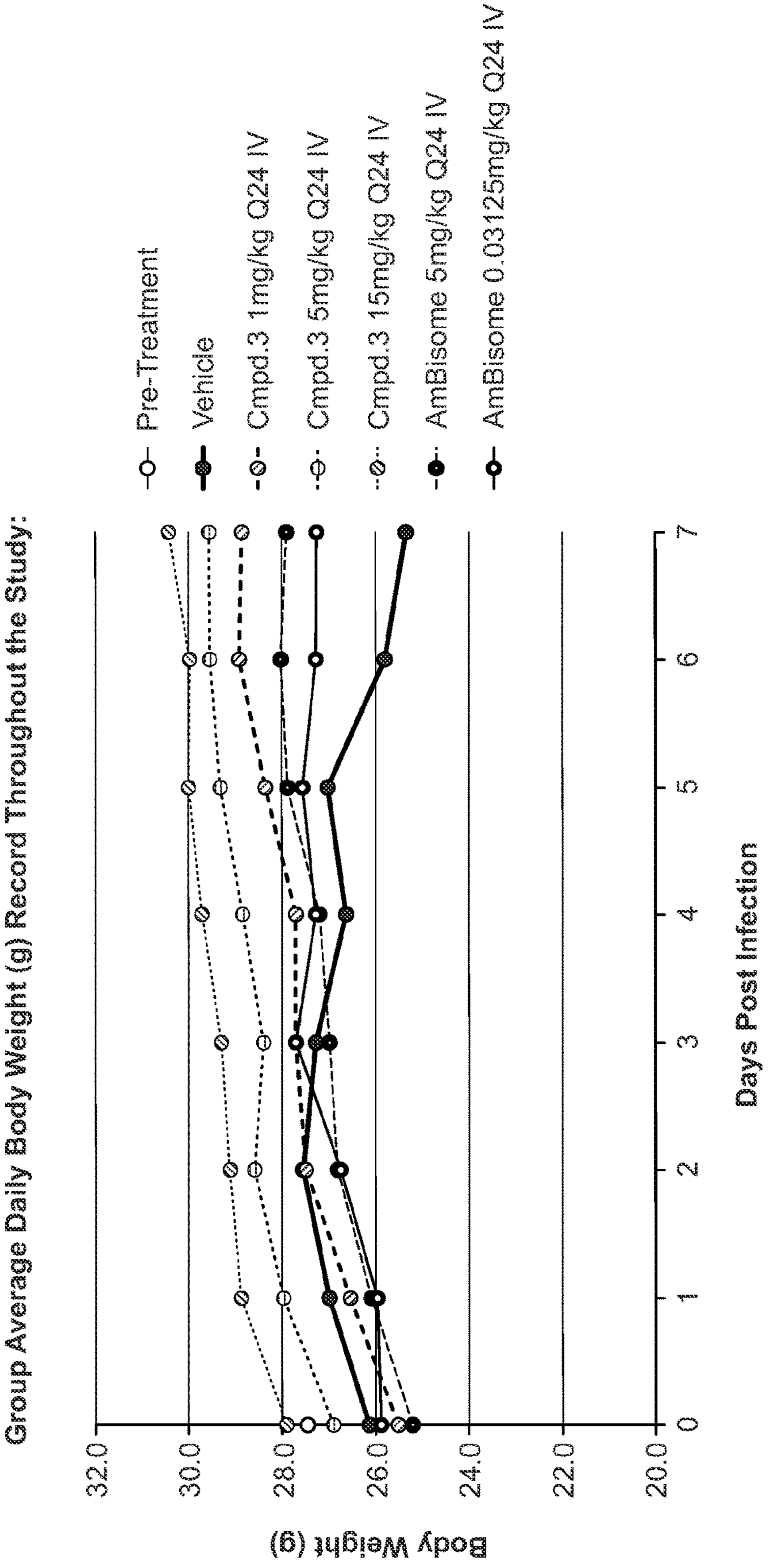
FIG. 18A depicts group average daily body weight for mice inoculated with *C. albicans* and treated with saline, compound 3, or AmB.
Figure 18B:
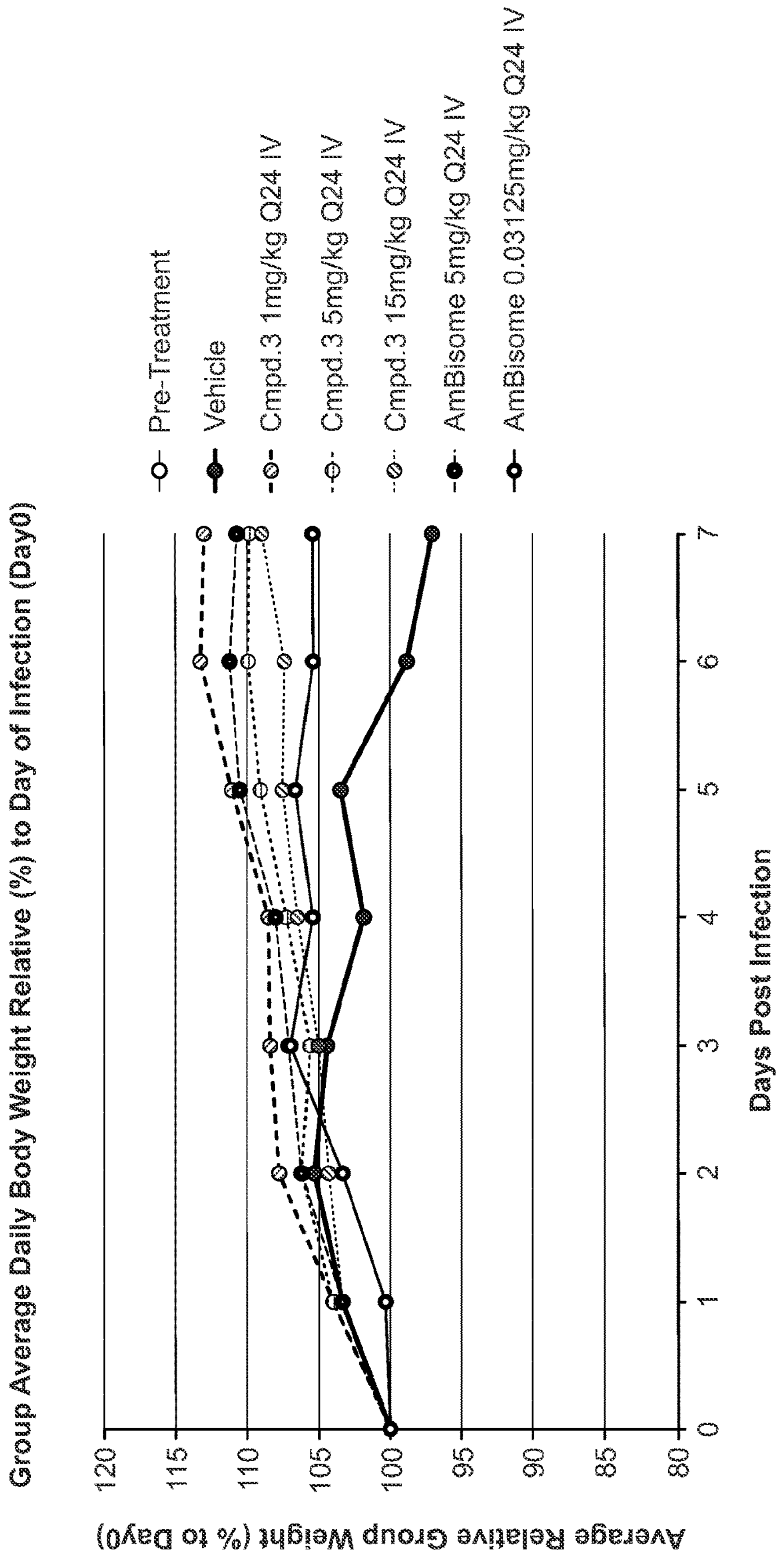
FIG. 18B depicts group average daily body weight relative to day of infection for mice inoculated with *C. albicans* and treated with saline, compound 3, or AmB.

Example 14. In Vivo Toxicity in Murine Model: (FIGS. 15 and 16)

In this study, in vivo toxicity of Compound 3 were studied using the expression of renal toxicity biomarker genes. Based on the number of different test candidates and different doses, female CD-1 mice (avg. body weight=27 g) were divided into groups where each group was consisting of 4 mice. On the day of the experiment different doses of Compound 3 were administered by IV. Groups treated with Ambisome and C2'epi AmB were used as references. After 24 h. all mice were sacrificed and the fungal burden in kidney were harvested and stored in RNA later at −80° C. Later the kidneys were homogenized and RNA was extracted. The expression of KIM1, LCN2, TIMP1 and SPP1 genes were measured in reference to GAPDH using RT-PCR technique.

| | Compound 3 | | | | AmBisome | C2'epiAmB |
|---|---|---|---|---|---|---|
| | 1.5 mg/kg | 5 mg/kg | 15 mg/kg | 45 mg/kg | 45 mg/kg | 45 mg/kg |
| # of mice alive | 4/4 | 4/4 | 4/4 | 4/4 | 4/4 | 4/4 |
| # of mice distress-free | 4/4 | 4/4 | 4/4 | 4/4 | 2/4 | 4/4 |

Example 15. Tolerance of Compound 3 and Changes in Renal Biomarkers and Gene Expression Following Administration of Compound 1 or 3 (FIGS. 11A-11C and 12)

hERG inhibition, plasma compatibility and Ames assays were performed using industrial standard protocol.

hERG inhibition study: No inhibition of hERG potassium current up to 100 uM, highest concentration tested.

Plasma compatibility: There was ppt observed at all 3 concentrations at a 1:1 dilution; only observed at 5 mg/mL at a 1:0.1 dilution. Formulation optimization ongoing.

Ames study: No genotoxicity response observed at any dose levels tested

Example 16. In Vitro Tolerance of Compound 3 (FIGS. 20A-20D)

Procedure:

Four different cell lines were obtained from ATCC and the tolerance of compound 3 was tested alongside AmB, C2'epiAmB and Compound 4 following the recommendations of ATCC.

Figure 20A:
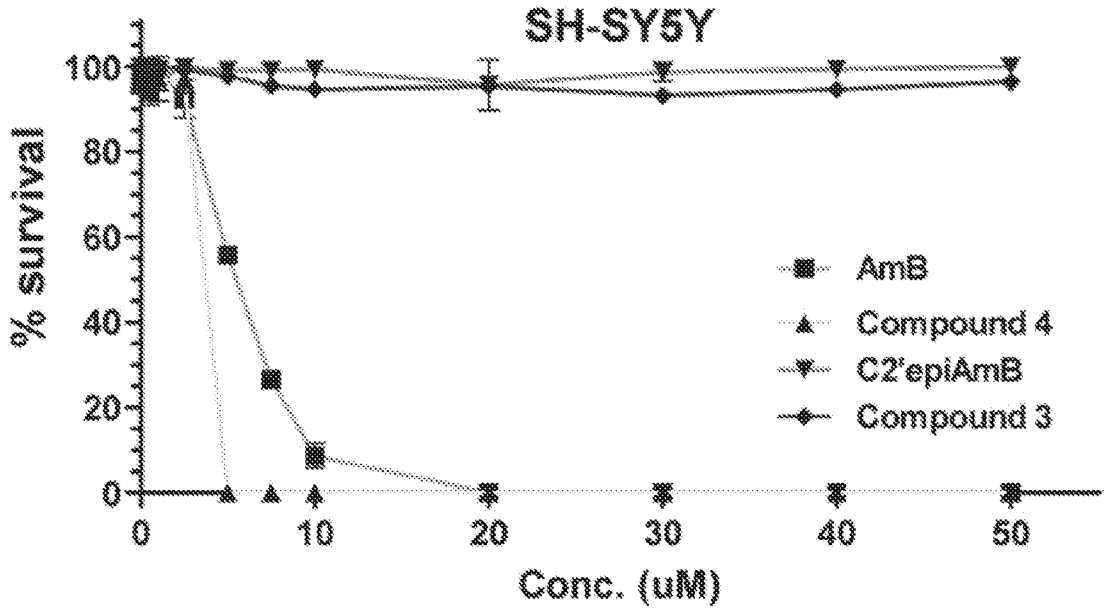
FIGS. 20A-20D depict the results of in vitro tolerance studies using Compound 3.

Neurotoxicity:

SH-SY5Y (CRL-2266; human neural blastoma; FIG. 20A). Cells were grown in complete MEM media and tolerance was tested in 96 well plates in triplicate. DMSO and puromycin (100 μM) were used as the positive and negative controls. During the experiment inoculum density was maintained to $10^4$ cells/well ($5\times10^5$ CFU/mL). All test compound stock solutions were prepared in DMSO and the DMSO concentration in the final culture was maintained to 1%. After addition of the compounds to the culture it was incubated at 35° C. under 5% $CO_2$ atmosphere for 24 h and the cell viability was measured using Alamar blue fluorescence dye (excitation 555 nm and fluorescence 585 nm.

Figure 20B:
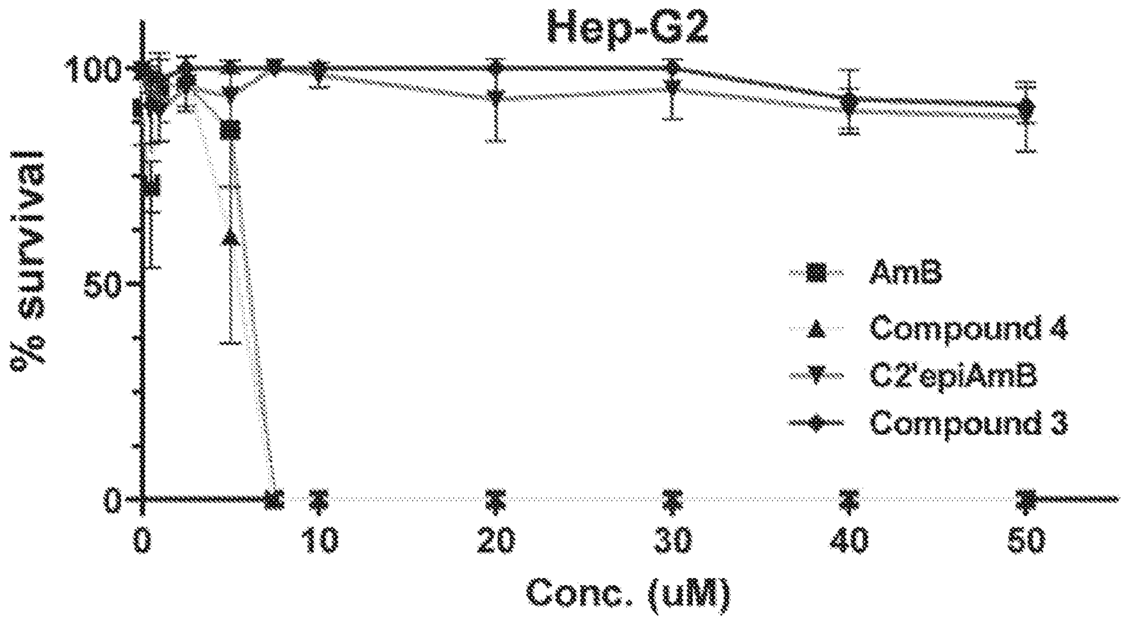

Hepatotoxicity:

Hep-G2 (HB-8065; human liver cell; FIG. 20B). Cells were grown in complete MEM media and tolerance was tested in 96 well plates in triplicate. DMSO and puromycin (100 μM) were used as the positive and negative controls. During the experiment inoculum density was maintained to $10^4$ cells/well ($5\times10^5$ CFU/mL). All test compound stock solutions were prepared in DMSO and the DMSO concentration in the final culture was maintained to 1%. After addition of the compounds to the culture, it was incubated at 35° C. under 5% $CO_2$ atmosphere for 24 h and the cell viability was measured using Alamar blue fluorescence dye (excitation 555 nm and fluorescence 585 nm).

Figure 20C:
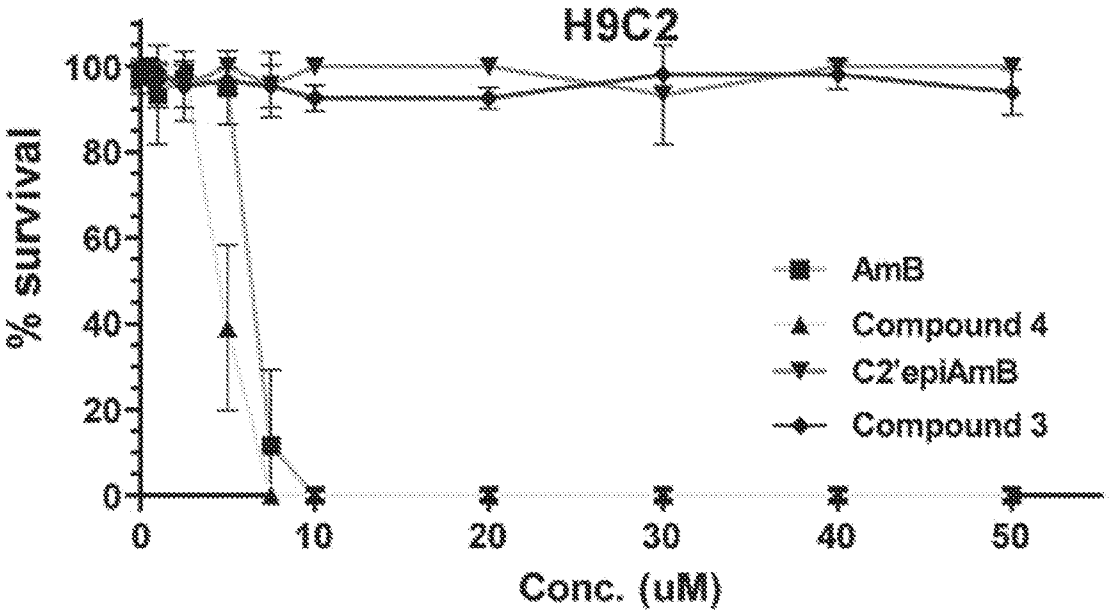

Cardiotoxicity:

H9C2 (CRL-1446; rat cardio myocyte; FIG. 20C). Cells were grown in complete DMEM media and tolerance was tested in 96 well plates in triplicate. DMSO and puromycin (100 μM) were used as the positive and negative controls. During the experiment inoculum density was maintained to $10^4$ cells/well ($5\times10^5$ CFU/mL). All test compound stock solutions were prepared in DMSO and the DMSO concentration in the final culture was maintained to 1%, After addition of the compounds to the culture it was incubated at 35° C. under 5% $CO_2$ atmosphere for 24 h and the cell viability was measured using Alamar blue fluorescence dye (excitation 555 nm and fluorescence 585 nm).

Figure 20D:
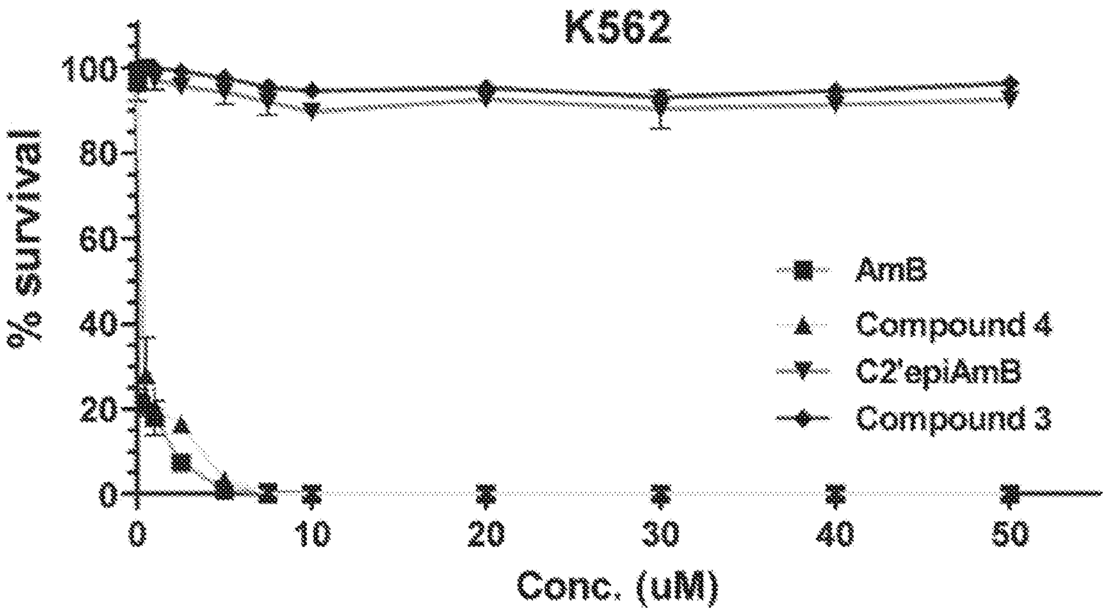
Figure 21A:
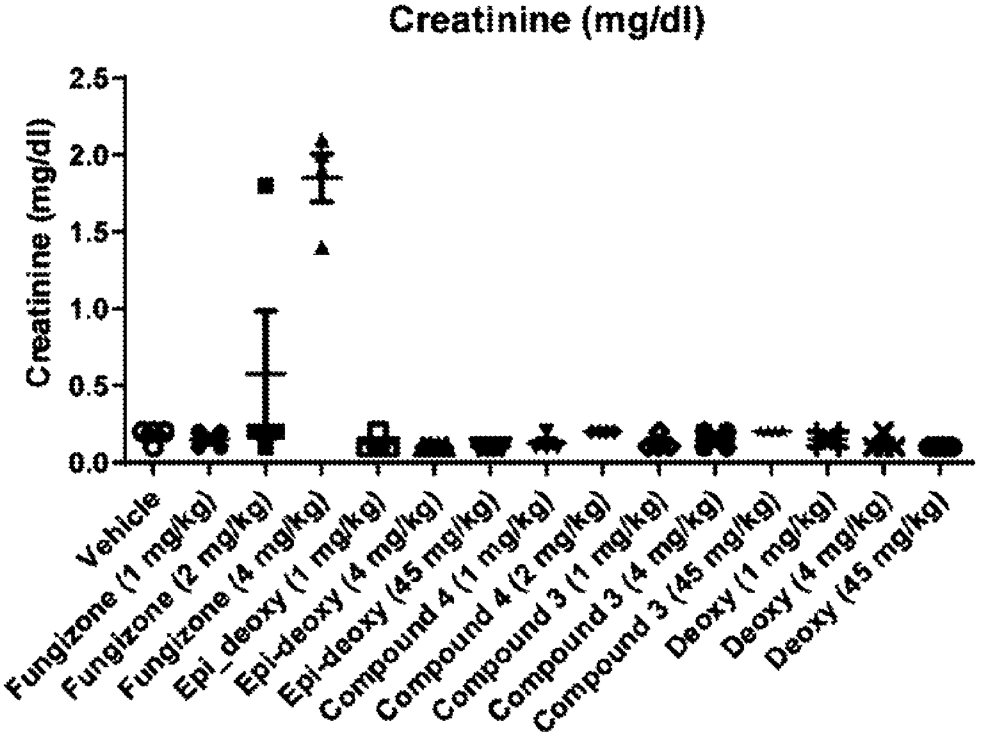
FIGS. 21A-21G depict in vivo tolerance studies of Compound 3 in mice.
Figure 21B:
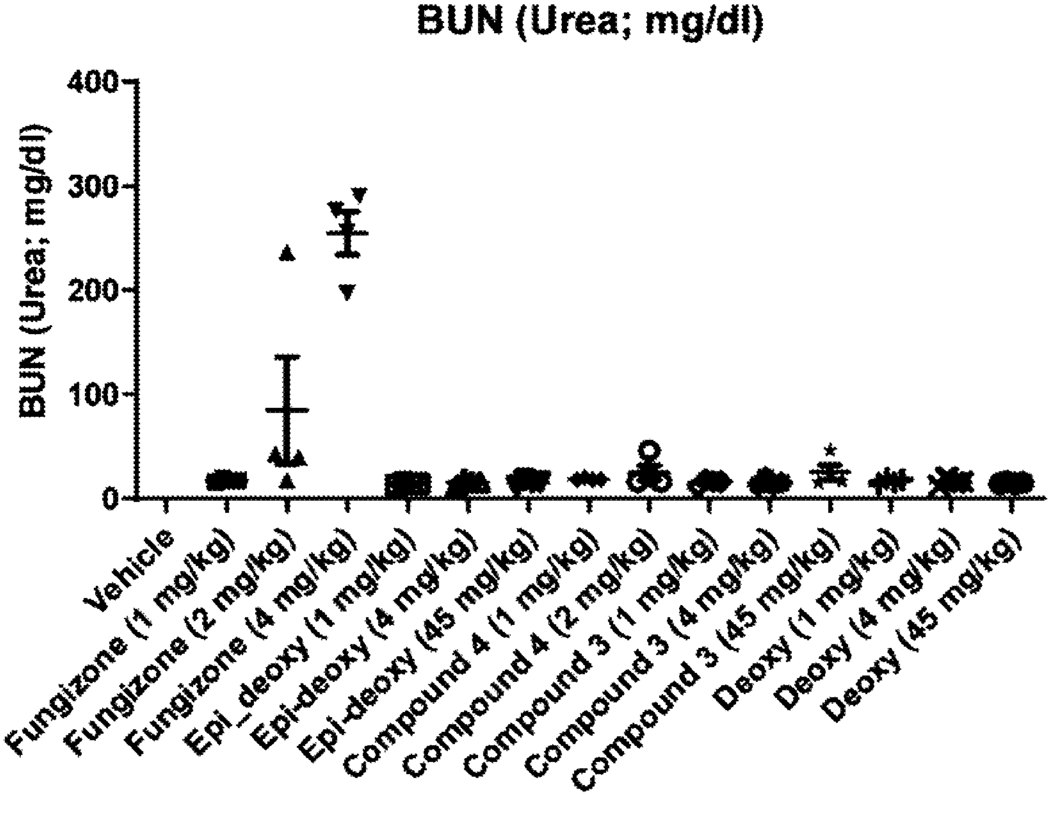
Figure 21C:
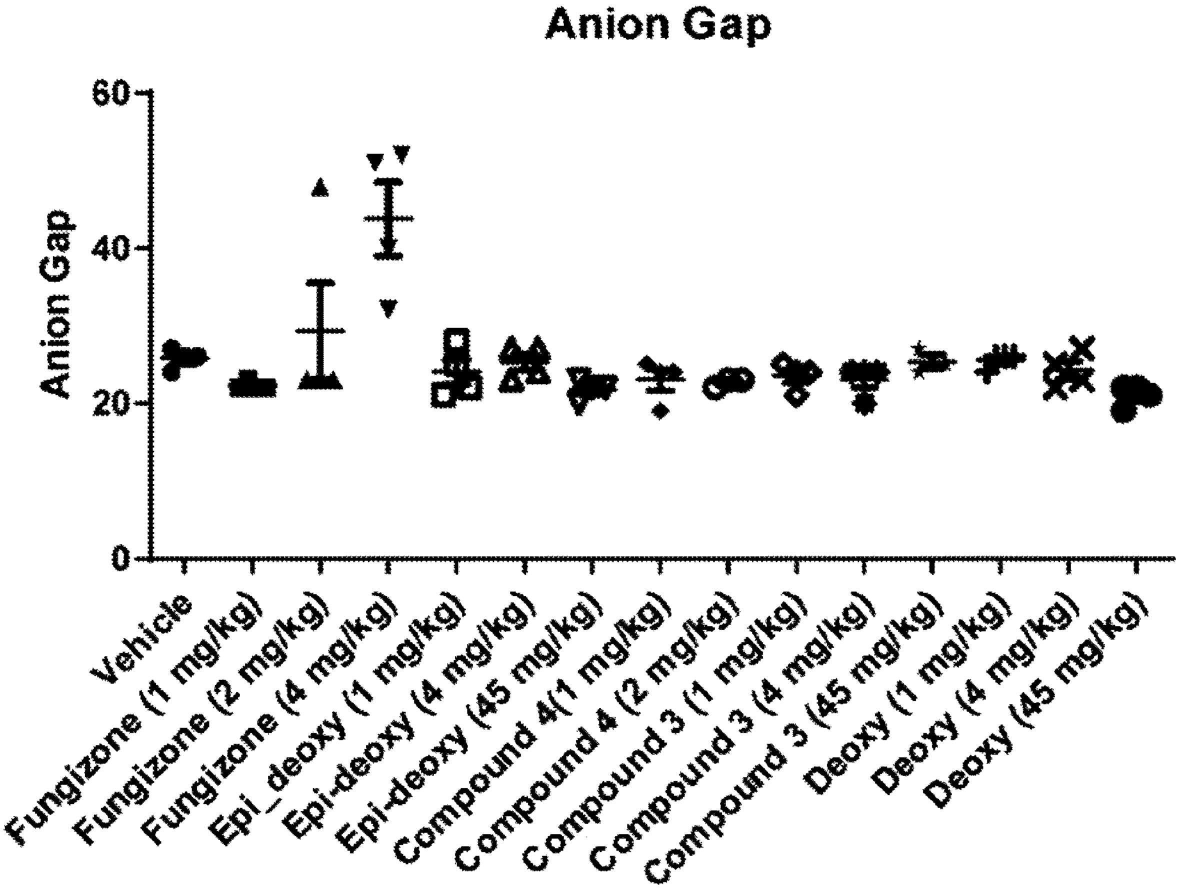
Figure 21D:
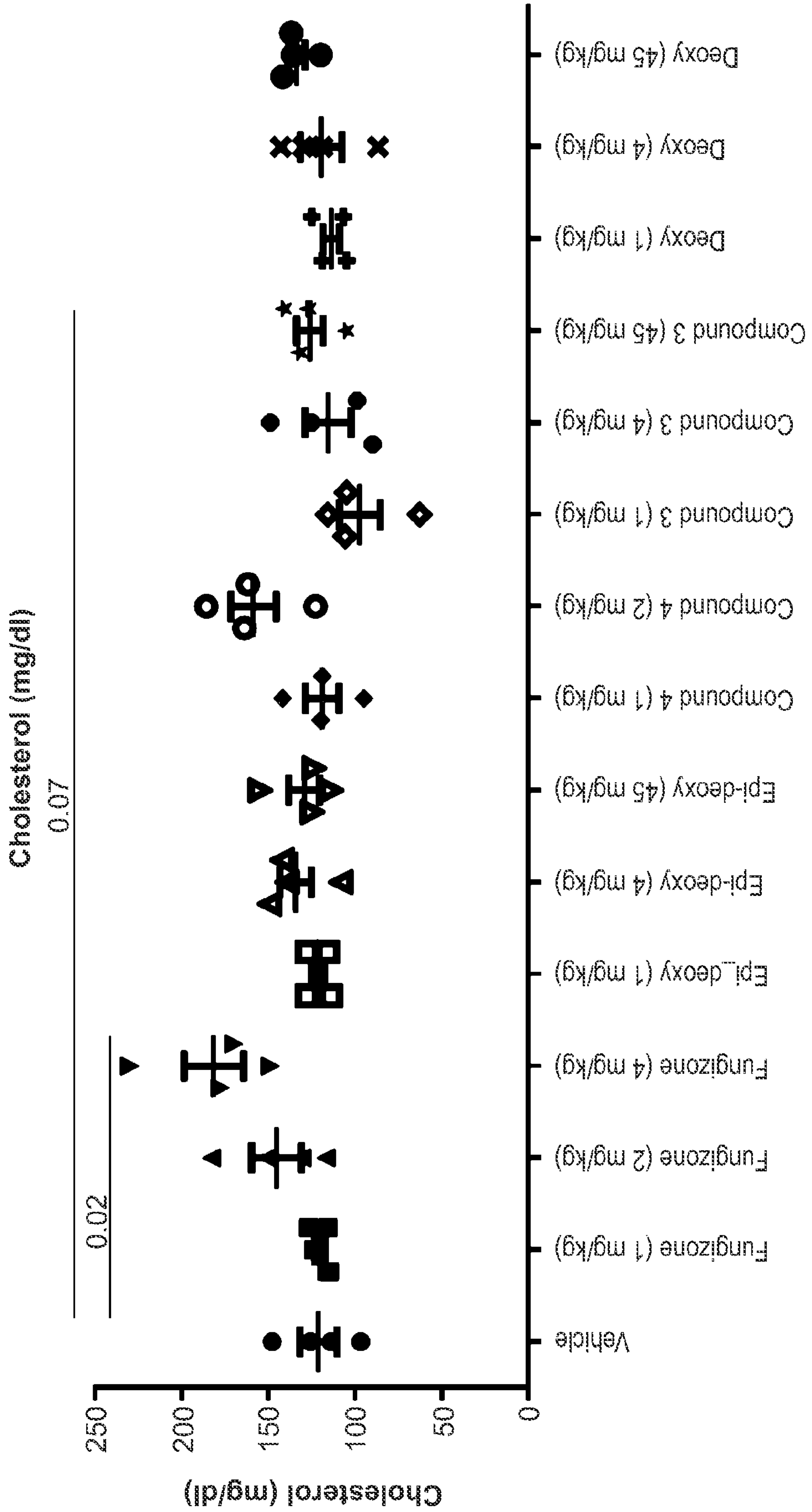
Figure 21E:
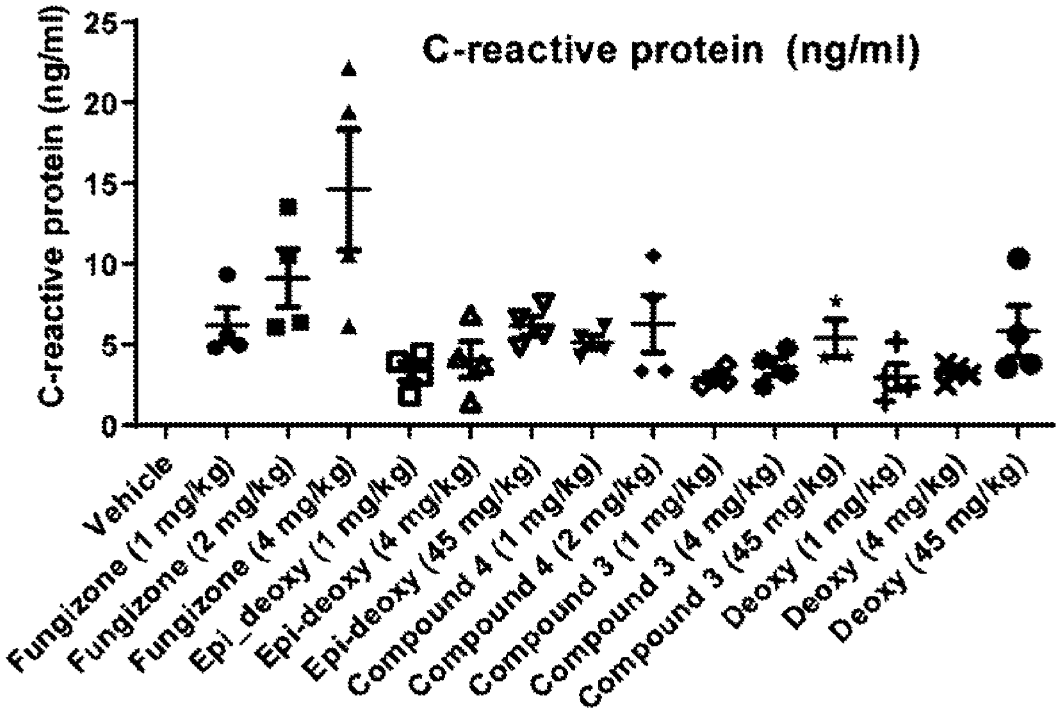
Figure 21F:
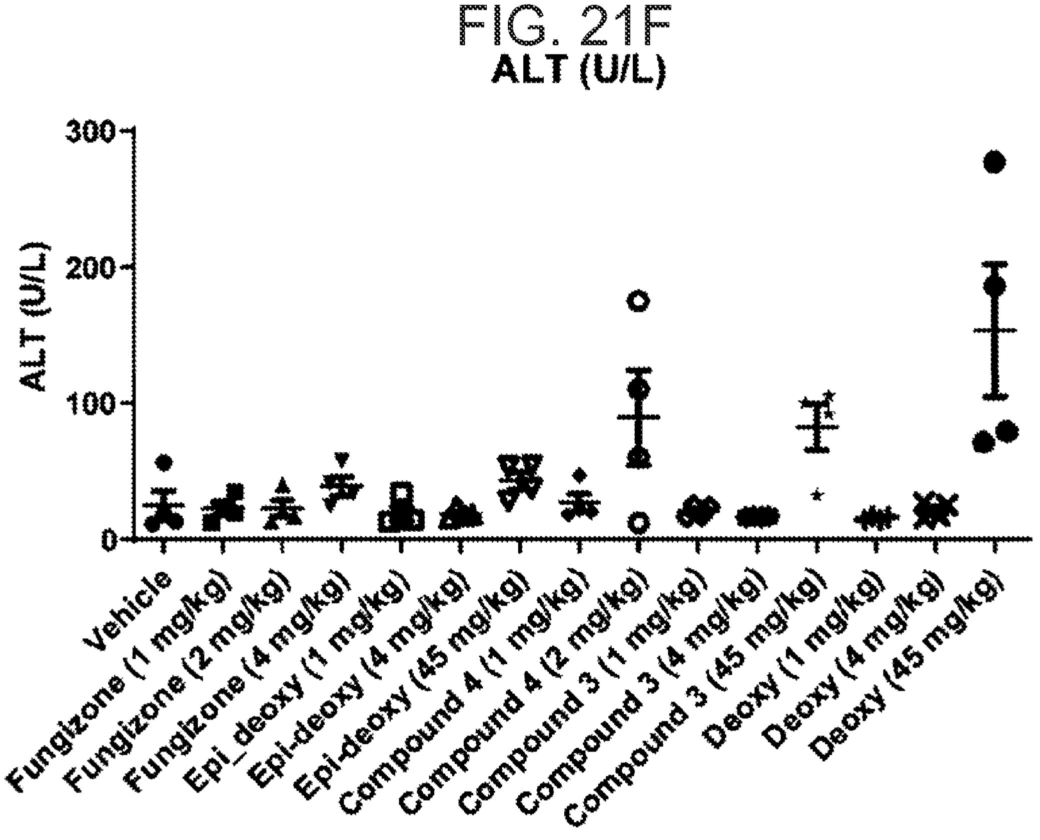
Figure 21G:
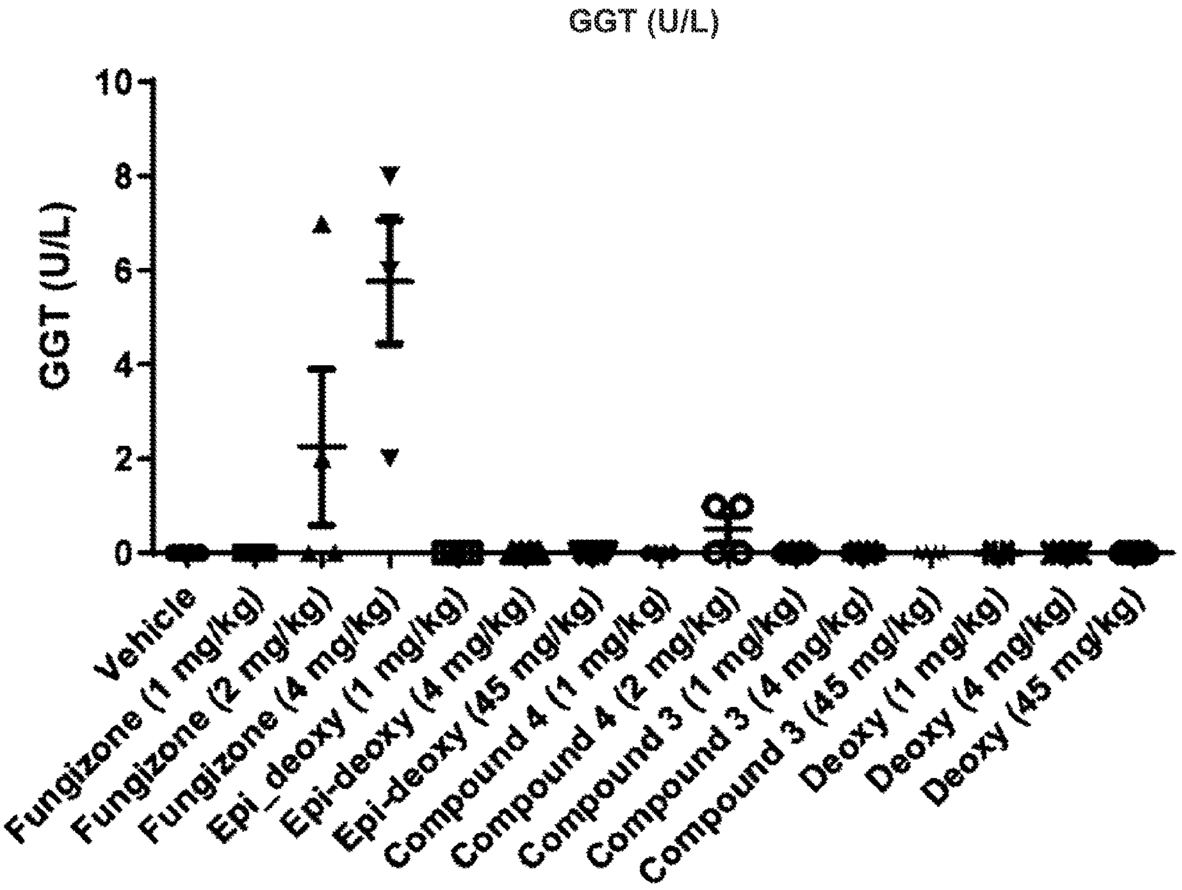

Hemotoxicity:

K562 (CCL-243; human lymphoblast; FIG. 20D). Cells were grown in complete IMDM media and tolerance was tested in 96 well plates in triplicate. DMSO and puromycin (100 μM) were used as the positive and negative controls. During the experiment inoculum density was maintained to $10^5$ cells/well ($5 \times 10^6$CFU/mL). All test compound stock solutions were prepared in DMSO and the DMSO concentration in the final culture was maintained to 1%, After addition of the compounds to the culture it was incubated at 35° C. under 5% $CO_2$ atmosphere for 24 h and the cell viability was measured using Alamar blue fluorescence dye (excitation 555 nm and fluorescence 585 nm).

Example 17. In Vivo Tolerance of Compound 3 in Mice (FIGS. 21A-21G)

Healthy female CD-1 mice were divided as 4 mice/group. The test compounds were dissolved in sterile clinically approved D5W (5% dextrose) and infused through tail vain during the study. Concentration of the compound was adjusted accordingly to get the target dosage with 0.3 mL injection. After 24 h of incubation, animals were euthanized, blood samples were collected for quantitative analysis of clinical analytes and organs were harvested for histopathological analysis.

| Compound | Dose (mg/kg) | Survival (alive/total) | Distressed |
|---|---|---|---|
| AmB-deoxycholate (1:2) (Fungizone)* | 1 | 4/4 | 0/4 |
| | 2 | 4/4 | 0/4 |
| | 4* | 4/4 | 4/4 |
| 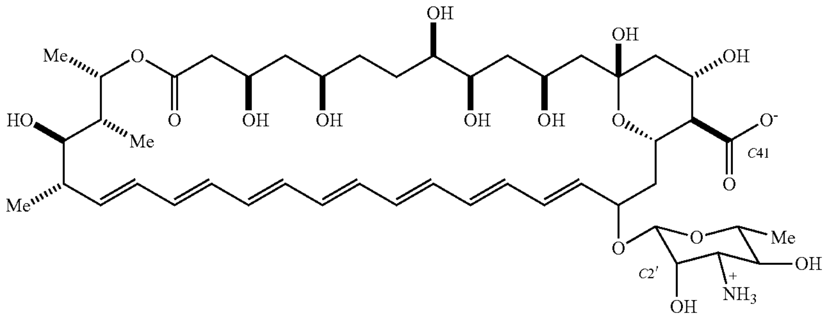 AmB | | | |
| C2'epiAmB-deoxycholate (1:2) | 1 | 4/4 | 0/4 |
| | 4 | 4/4 | 0/4 |
| | 45 | 4/4 | 0/4 |
| 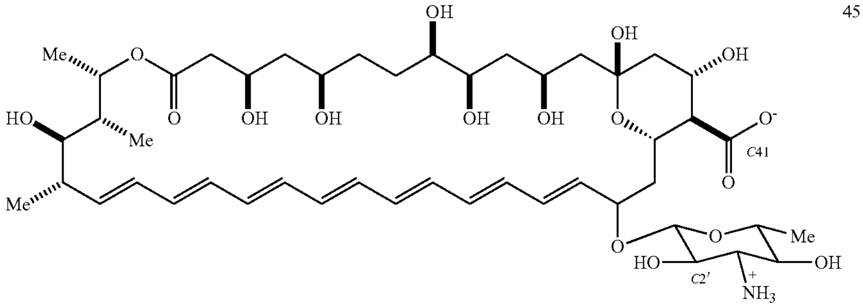 C2'epi-AmB | | | |
| Compound 4 | 1 | 4/4 | 0/4 |
| | 2 | 4/7 | 2/4 |
| | 4 | 0/6 | — |
| 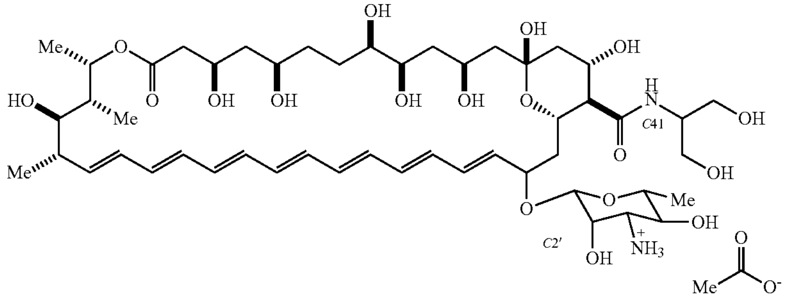 Compound 4 | | | |
| Compound 3 | 1 | 4/4 | 0/4 |
| | 4 | 4/4 | 0/4 |

-continued

| Compound | Dose (mg/kg) | Survival (alive/total) | Distressed |
|---|---|---|---|
| 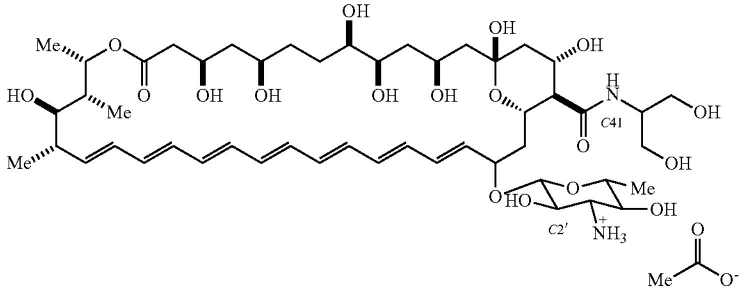 Compound 3 | 45 | 4/4 | 0/4 |
| Deoxycholate** | 1 | 4/4 | 0/4 |
| | 4 | 4/4 | 0/4 |
| | 45 | 4/4 | 0/4 |

*Historically not tolerated at 4 mg/kg

**Based on the amount present in Epi-Deoxy dose regimen

| | | Fungizone (AmB:deoxycholate 1:2) | | | | | | | | | | | |
|---|---|---|---|---|---|---|---|---|---|---|---|---|---|
| | | 1 mg/kg | | | | 2 mg/kg | | | | 4 mg/kg | | | |
| Foreign material | Lung | 0 | 0 | 0 | 0 | 0 | 0 | 0 | 0 | 0 | 0 | 0 | 0 |
| Hemorrhage, alveolar | | 0 | 3F | 0 | 2F | 0 | 0 | 0 | 0 | 0 | 0 | 0 | 0 |
| Infiltrate, alveolar macrophages | | 0 | 2F | 0 | 1F | 0 | 0 | 0 | 0 | 0 | 0 | 0 | 0 |
| Infiltrate, mixed-cell | | 0 | 0 | 0 | 1F | 0 | 0 | 0 | 0 | 0 | 0 | 0 | 0 |
| Edema, interstitial | Heart | 0 | 0 | 0 | 0 | 0 | 0 | 0 | 0 | 0 | 0 | 0 | 0 |
| Infiltrate, mixed-cell | | 0 | 0 | 0 | 0 | 0 | 0 | 0 | 0 | 0 | 0 | 0 | 0 |
| Myodegeneration | | 0 | 0 | 0 | 0 | 0 | 0 | 0 | M | 0 | 0 | 0 | 0 |
| Infiltrate, mixed-cell | Liver | 1M | 1M | 1M | 0 | 0 | 2M | 0 | M | 1F | 0 | 1M | 1M |
| Necrosis | | 0 | 0 | 0 | 0 | 0 | 0 | 0 | 0 | 0 | 0 | 0 | 0 |
| Neutrophil infiltration | | 0 | 0 | 0 | 0 | 0 | 0 | 0 | 0 | 0 | 0 | 0 | 0 |
| Contraction | Spleen | 0 | 0 | 0 | 0 | 0 | P | 0 | 0 | 0 | 0 | 0 | 0 |
| Increased neutrophils, red pulp | | 0 | 0 | 0 | 0 | 0 | 1M | 1M | 2M | 2M | 2M | 2M | 2M |
| Lymphocytolysis | | 0 | 0 | 0 | 0 | 0 | 0 | 0 | 0 | 2M | 2M | 0 | 0 |
| Increased interstitial histiocytes | Kidney | 0 | 0 | 0 | 0 | 0 | 0 | 0 | 0 | 0 | 0 | 0 | 2M |
| Interstital edema, cortex | | 0 | 0 | 0 | 0 | 0 | 1M | 0 | 0 | 1M | 1M | 0 | 1M |
| Interstitial mixed-cell infiltrate | | 0 | 0 | 0 | 0 | 0 | 0 | 0 | 0 | 0 | 0 | 0 | 0 |
| Neutrophil infiltration, renal pelvis | | 0 | 0 | 0 | 0 | 0 | 0 | 0 | 0 | 2M | 0 | 0 | 0 |
| Tubular basophilia, cortex | | 0 | 0 | 1F | 0 | 0 | 0 | 0 | 0 | 0 | 0 | 0 | 2M |
| Tubular cellular casts, cortex | | 0 | 0 | 0 | 0 | 2M | 2M | 0 | 0 | 2M | 2M | 2M | 1M |
| Tubular cellular casts, medulla | | 0 | 0 | 0 | 0 | 4M | 4M | 3M | 3M | 4M | 4M | 4M | 3M |
| Tubular cyst, cortex | | 0 | 0 | 0 | 0 | 0 | 0 | 0 | 0 | 0 | 0 | 0 | 0 |
| Tubular degeneration and necrosis, cortex | | 0 | 0 | 0 | 0 | 2M | 2M | 0 | 0 | 2M | 2M | 2M | 2M |
| Tubular degeneration and necrosis, medulla | | 0 | 0 | 0 | 0 | 4M | 4M | 3M | 3M | 5M | 4M | 4M | 4M |
| Tubular dilatation, cortex | | 0 | 0 | 0 | 0 | 3M | 3M | 2M | 2M | 3M | 3M | 3M | 2M |
| Tubular protein casts, cortex | | 0 | 0 | 0 | 0 | 3M | 3M | 2M | 2M | 3M | 3M | 3M | 2M |
| Tubular protein casts, medulla | | 0 | 0 | 0 | 0 | 4M | 4M | 2M | 2M | 4M | 4M | 4M | 3M |
| Tubular regeneration, cortex | | 0 | 0 | 0 | 0 | 0 | 0 | 0 | 0 | 0 | 0 | 0 | 3M |
| Vascular congestion, medulla | | 0 | 0 | 0 | 0 | 4M | 4M | 0 | 3M | 5D | 4M | 4M | 4M |

| | | C2'epiAmB:deoxycholate 1:2 | | | | | | | | | | | |
|---|---|---|---|---|---|---|---|---|---|---|---|---|---|
| | | 1 mg/kg | | | | 4 mg/kg | | | | 45 mg/kg | | | |
| Foreign material | Lung | 0 | 0 | 0 | 0 | 0 | 0 | 0 | P | 0 | 0 | 0 | P |
| Hemorrhage, alveolar | | 0 | 0 | 0 | 0 | 0 | 0 | 0 | 0 | 0 | 0 | 0 | 0 |
| Infiltrate, alveolar macrophages | | 0 | 0 | 0 | 0 | 0 | 0 | 0 | 0 | 0 | 0 | 0 | 0 |
| Infiltrate, mixed-cell | | 0 | 0 | 0 | 0 | 0 | 0 | 1F | 2F | 0 | 0 | 0 | 2M |
| Edema, interstitial | Heart | 0 | 0 | 0 | 0 | 0 | 0 | 0 | 0 | 0 | 0 | 0 | 0 |
| Infiltrate, mixed-cell | | 0 | 0 | 0 | 0 | 0 | 0 | 0 | 0 | 0 | 0 | 0 | 0 |
| Myodegeneration | | 0 | 0 | 0 | 0 | 0 | 0 | 0 | 0 | 0 | 0 | 0 | 0 |
| Infiltrate, mixed-cell | Liver | 1M | 2M | 1M | 1M | 1F | 0 | 0 | 1F | 1M | 1M | 1M | 2M |
| Necrosis | | 0 | 0 | 0 | 0 | 0 | 0 | 0 | 0 | 0 | 0 | 0 | 0 |
| Neutrophil infiltration | | 0 | 0 | 0 | 0 | 0 | 0 | 0 | 0 | 0 | 0 | 0 | 0 |
| Contraction | Spleen | 0 | 0 | 0 | 0 | 0 | 0 | 0 | 0 | 0 | 0 | 0 | 0 |

-continued

| | | | | | | | | | | | | | |
|---|---|---|---|---|---|---|---|---|---|---|---|---|---|
| Increased neutrophils, red pulp | | 0 | 0 | 0 | 0 | 0 | 0 | 0 | 0 | 0 | 0 | 0 | 0 |
| Lymphocytolysis | | 0 | 0 | 0 | 0 | 0 | 0 | 0 | 0 | 0 | 0 | 0 | 0 |
| Increased interstitial histiocytes | Kidney | 0 | 0 | 0 | 0 | 0 | 0 | 0 | 0 | 0 | 0 | 0 | 0 |
| Interstital edema, cortex | | 0 | 0 | 0 | 0 | 0 | 0 | 0 | 0 | 0 | 0 | 0 | 0 |
| Interstitial mixed-cell infiltrate | | 0 | 0 | 0 | 0 | 0 | 0 | 0 | 0 | 0 | 0 | 0 | 0 |
| Neutrophil infiltration, renal pelvis | | 0 | 0 | 0 | 0 | 0 | 0 | 0 | 0 | 0 | 0 | 0 | 0 |
| Tubular basophilia, cortex | | 0 | 0 | 0 | 0 | 0 | 0 | 0 | 0 | 0 | 0 | 0 | 0 |
| Tubular cellular casts, cortex | | 0 | 0 | 0 | 0 | 0 | 0 | 0 | 0 | 0 | 0 | 0 | 0 |
| Tubular cellular casts, medulla | | 0 | 0 | 0 | 0 | 0 | 0 | 0 | 0 | 2M | 2M | 0 | 0 |
| Tubular cyst, cortex | | 0 | P | 0 | 0 | 0 | 0 | 0 | 0 | 0 | 0 | 0 | 0 |
| Tubular degeneration and necrosis, cortex | | 0 | 0 | 0 | 0 | 0 | 0 | 0 | 0 | 0 | 0 | 0 | 0 |
| Tubular degeneration and necrosis, medulla | | 0 | 0 | 0 | 0 | 0 | 0 | 0 | 0 | 2M | 2M | 0 | 0 |
| Tubular dilatation, cortex | | 0 | 0 | 0 | 0 | 0 | 0 | 0 | 0 | 0 | 0 | 0 | 0 |
| Tubular protein casts, cortex | | 0 | 0 | 1F | 0 | 0 | 1M | 0 | 0 | 0 | 0 | 0 | 0 |
| Tubular protein casts, medulla | | 0 | 0 | 1M | 0 | 0 | 1M | 0 | 0 | 0 | 1M | 0 | 0 |
| Tubular regeneration, cortex | | 0 | 0 | 0 | 0 | 0 | 0 | 0 | 0 | 0 | 0 | 0 | 0 |
| Vascular congestion, medulla | | 0 | 0 | 0 | 0 | 0 | 0 | 0 | 0 | 0 | 0 | 0 | 0 |

| | | Compound 4 | | | | | | | |
|---|---|---|---|---|---|---|---|---|---|
| | | 1 mg/kg | | | | 2 mg/kg | | | |
| Foreign material | Lung | 0 | 0 | 0 | 0 | 0 | 0 | 0 | 0 |
| Hemorrhage, alveolar | | 0 | 1F | 0 | 0 | 0 | 0 | 1F | 0 |
| Infiltrate, alveolar macrophages | | 0 | 0 | 0 | 0 | 0 | 0 | 0 | 0 |
| Infiltrate, mixed-cell | | 0 | 0 | 0 | 0 | 0 | 0 | 0 | 0 |
| Edema, interstitial | Heart | 0 | 0 | 1F | 0 | 0 | 1F | 0 | 0 |
| Infiltrate, mixed-cell | | 0 | 0 | 2M | 0 | 0 | 2F | 0 | 0 |
| Myodegeneration | | 0 | 0 | IF | 0 | 0 | 0 | 0 | 0 |
| Infiltrate, mixed-cell | Liver | 1M | 0 | 1M | 1M | 1F | 0 | 0 | 1M |
| Necrosis | | 0 | 2M | 0 | 0 | 0 | 0 | 0 | 0 |
| Neutrophil infiltration | | 0 | 2M | 0 | 0 | 0 | 0 | 0 | 0 |
| Contraction | Spleen | 0 | 0 | 0 | 0 | 0 | 0 | 0 | 0 |
| Increased neutrophils, red pulp | | 0 | 0 | 0 | 0 | 0 | 0 | 0 | 0 |
| Lymphocytolysis | | 0 | 0 | 0 | 0 | 0 | 0 | 0 | 0 |
| Increased interstitial histiocytes | Kidney | 0 | 0 | 0 | 0 | 0 | 0 | 0 | 0 |
| Interstital edema, cortex | | 0 | 0 | 0 | 0 | 0 | 0 | 0 | 0 |
| Interstitial mixed-cell infiltrate | | 1M | 2F | 0 | 1M | 1M | 0 | 0 | 0 |
| Neutrophil infiltration, renal pelvis | | 0 | 0 | 0 | 0 | 0 | 0 | 0 | 0 |
| Tubular basophilia, cortex | | 0 | 2F | 1F | 0 | 0 | 0 | 0 | 0 |
| Tubular cellular casts, cortex | | 0 | 0 | 0 | 0 | 0 | 0 | 2M | 0 |
| Tubular cellular casts, medulla | | 0 | 3M | 0 | 0 | 2M | 1M | 2M | 0 |
| Tubular cyst, cortex | | 0 | 0 | 0 | 0 | 0 | 0 | 0 | 0 |
| Tubular degeneration and necrosis, cortex | | 0 | 0 | 0 | 0 | 0 | 0 | 2M | 0 |
| Tubular degeneration and necrosis, medulla | | 0 | 3M | 0 | 0 | 3M | 2M | 3M | 0 |
| Tubular dilatation, cortex | | 1M | 2M | 0 | 0 | 0 | 0 | 3M | 0 |
| Tubular protein casts, cortex | | 0 | 2M | 0 | 0 | 0 | 0 | 3M | 0 |
| Tubular protein casts, medulla | | 0 | 2M | 0 | 0 | 0 | 1M | 3M | 0 |
| Tubular regeneration, cortex | | 0 | 0 | 0 | 0 | 0 | 0 | 0 | 0 |
| Vascular congestion, medulla | | 0 | 3M | 0 | 0 | 0 | 0 | 3M | 0 |

| | | Compound 3 | | | | | | | | | | | |
|---|---|---|---|---|---|---|---|---|---|---|---|---|---|
| | | 1 mg/kg | | | | 4 mg/kg | | | | 45 mg/kg | | | |
| Foreign material | Lung | 0 | 0 | 0 | 0 | 0 | 0 | 0 | 0 | 0 | 0 | 0 | 0 |
| Hemorrhage, alveolar | | 0 | 0 | 0 | 0 | 0 | 0 | 0 | 2M | 2M | 0 | 0 | 0 |
| Infiltrate, alveolar macrophages | | 0 | 0 | 0 | 0 | 0 | 0 | 0 | 0 | 0 | 0 | 0 | 0 |
| Infiltrate, mixed-cell | | 0 | 0 | 0 | 0 | 0 | 0 | 0 | 0 | 0 | 0 | 0 | 0 |
| Edema, interstitial | Heart | 0 | 0 | 0 | 0 | 0 | 0 | 0 | 0 | 0 | 0 | 0 | 0 |
| Infiltrate, mixed-cell | | 0 | 0 | 0 | 0 | 0 | 0 | 0 | 0 | 0 | 0 | 0 | 0 |
| Myodegeneration | | 0 | 0 | 0 | 0 | 0 | 0 | 0 | 0 | 0 | 0 | 0 | 0 |
| Infiltrate, mixed-cell | Liver | 1M | 0 | 0 | 1M | 1M | 1M | 1M | 1F | 0 | 2M | 0 | 0 |
| Necrosis | | 0 | 0 | 0 | 0 | 0 | 0 | 0 | 0 | 0 | 0 | 0 | 0 |
| Neutrophil infiltration | | 0 | 0 | 0 | 0 | 0 | 0 | 0 | 0 | 0 | 0 | 0 | 0 |
| Contraction | Spleen | 0 | 0 | 0 | 0 | 0 | 0 | 0 | 0 | 0 | 0 | 0 | 0 |
| Increased neutrophils, red pulp | | 0 | 0 | 0 | 0 | 0 | 0 | 0 | 0 | 0 | 0 | 0 | 0 |

-continued

| | | | | | | | | | | | | | |
|---|---|---|---|---|---|---|---|---|---|---|---|---|---|
| Lymphocytolysis | | 0 | 0 | 0 | 0 | 0 | 0 | 0 | 0 | 0 | 0 | 0 | 0 |
| Increased interstitial histiocytes | Kidney | 0 | 0 | 0 | 0 | 0 | 0 | 0 | 0 | 0 | 0 | 0 | 0 |
| Interstital edema, cortex | | 0 | 0 | 0 | 0 | 0 | 0 | 0 | 0 | 0 | 0 | 0 | 0 |
| Interstitial mixed-cell infiltrate | | 0 | 0 | 0 | 0 | 0 | 0 | 0 | 0 | 0 | 0 | 0 | 0 |
| Neutrophil infiltration, renal pelvis | | 0 | 0 | 0 | 0 | 0 | 0 | 0 | 0 | 0 | 0 | 0 | 0 |
| Tubular basophilia, cortex | | 0 | 0 | 0 | 0 | 0 | 0 | 0 | 0 | 0 | 0 | 0 | 0 |
| Tubular cellular casts, cortex | | 0 | 0 | 0 | 0 | 0 | 0 | 0 | 0 | 0 | 0 | 0 | 0 |
| Tubular cellular casts, medulla | | 0 | 0 | 0 | 0 | 0 | 0 | 0 | 0 | 2M | 0 | 0 | 0 |
| Tubular cyst, cortex | | 0 | 0 | 0 | 0 | 0 | 0 | 0 | 0 | 0 | 0 | 0 | 0 |
| Tubular degeneration and necrosis, cortex | | 0 | 0 | 0 | 0 | 0 | 0 | 0 | 0 | 0 | 0 | 0 | 0 |
| Tubular degeneration and necrosis, medulla | | 0 | 0 | 0 | 0 | 0 | 0 | 0 | 0 | 0 | 0 | 0 | 0 |
| Tubular dilatation, cortex | | 0 | 0 | 0 | 0 | 0 | 0 | 0 | 0 | 0 | 0 | 0 | 0 |
| Tubular protein casts, cortex | | 0 | 0 | 0 | 0 | 0 | 1F | 1F | 0 | 1M | 0 | 0 | 0 |
| Tubular protein casts, medulla | | 0 | 0 | 0 | 0 | 0 | 1F | 1F | 1F | 0 | 0 | 0 | 0 |
| Tubular regeneration, cortex | | 0 | 0 | 0 | 0 | 0 | 0 | 0 | 0 | 0 | 0 | 0 | 0 |
| Vascular congestion, medulla | | 0 | 0 | 0 | 0 | 0 | 0 | 0 | 0 | 0 | 0 | 0 | 0 |

0 = histologically unremarkable;
1 = minimal;
2 = mild;
3 = moderate;
4 = marked;
5 = severe
D = diffuse;
F = focal;
M = multifocal:
P = present

Example 18: In Vitro Efficacy of Compound 3 Against Azole and Echinocandin Resistant Fungal Strains This experiment was performed following the standard CLSI protocol.

| | | MIC (mM) | | | | |
|---|---|---|---|---|---|---|
| STRAIN | Strain Info | Compound 3 | AmBisome | Voriconazole | Caspofungin | Posaconazole |
| CEA10 | clinical isolate | 1.00 | 0.54 | 1.43 | 0.41 | 0.18 |
| Af 3626 | ATCC strain | 1.00 | 0.54 | 0.72 | 0.41 | |
| Af F12776 | azole resistant (Y431C) | 0.50 | 0.54 | >11.46 | 0.41 | |
| Af F14946 | azole resistant (G138C) | 1.00 | 0.54 | >11.46 | 0.41 | |
| Af F16134 | azole resistant (M220K) | 1.00 | 1.08 | >11.46 | 0.21 | |
| Af F16216 | azole resistant (L98H + TR) | 0.50 | 0.54 | >11.46 | 0.41 | 1.43 |
| Af F7075 | azole resistant (G54E) | 1.00 | 0.54 | 5.73 | 0.82 | |
| EMFR-S678P | echinocandin resistant | 2.01 | 0.54 | 1.43 | >3.3 | |

Figure 22:
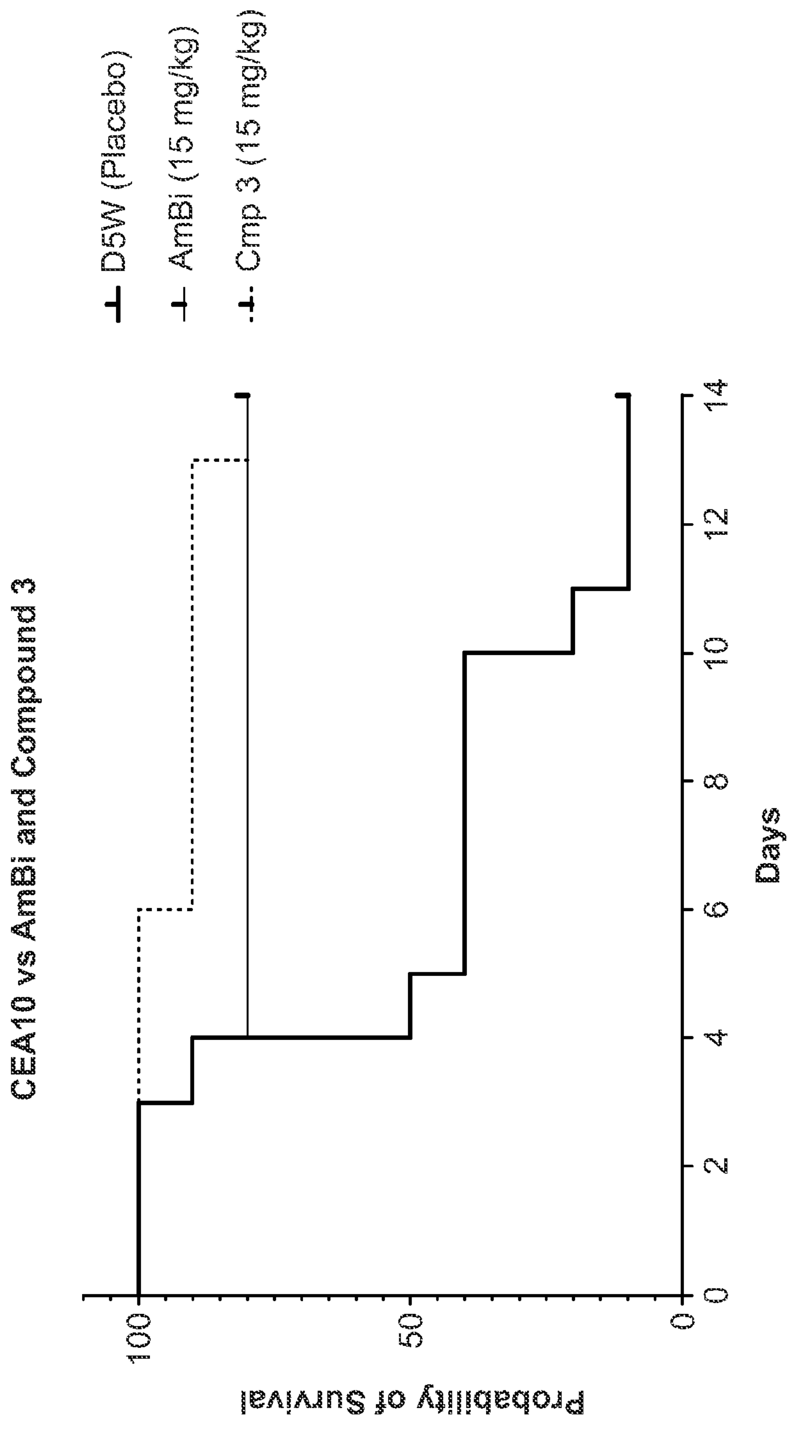
FIG. 22 depicts the in vivo efficacy of Compound 3 against pulmonary aspergillosis in mice.
Figure 23:
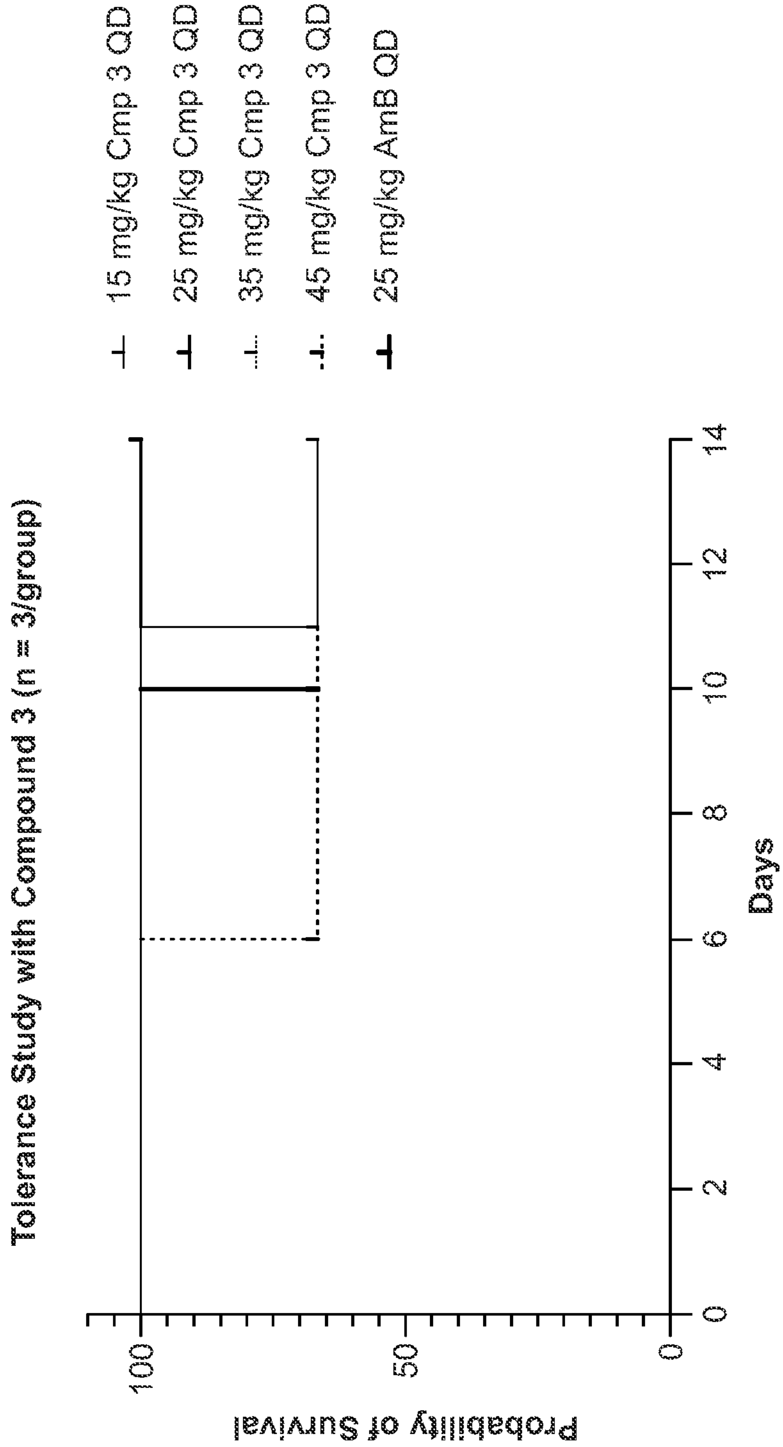
FIG. 23 depicts the in vivo tolerance of Compound 3 against pulmonary aspergillosis in mice.

Example 19: Protocol Development for Efficacy Study of Compound 3 Against Pulmonary Aspergillosis in Mice (FIGS. 22 and 23)

Efficacy study (FIG. 22): Healthy mice were divided as 10 mice/group. All the animals were treated with cyclophosphamide (150 mg/kg) on day −2 and +3 and Cortisone acetate (250 mg/kg) on day −1 and +6 to convert them neutropenic. Animals were infected with *A. funigatus* (CEA10 strain) (intranasal) on day 0. All animal were given 15 mg/kg/day (IP) of Ambisome or Compound 3 for 7 days and monitored until day 14 post-infection. Survivability of the animals were monitored during the course of the study.

Objective: Test Compound 3 and AmB against CEA10 (wild-type) IA

1e8 spores/mL (40 uL) intranasal CEA10 n=10 mice/group

Cyclophosphamide: 150 mg/kg Days −2 and −3

Cortisone Acetate: 250 mg/kg Days −1 and +6

Survival:

D5W only: 10%

Compound 3 15 mg/kg QD: 80%

AmB 15 mg/kg QD:80%

Log Rank Statistics:

D5W vs Compound 3 15 mg/kg QD: p=0.0005

D5W vs AmB 15 mg/kg QD: p=0.0044

Notes:

Compound 3 and AmB at 15 mg/kg dosed daily for 7 days post infection IP protects against CEA10 IA infection equally after 14 days. Amb IP dosing of 15 mg/kg estimated as at least as much as 5 mg/kg IV. Since IP dosing is new for Compound 3 and AmB, we want to understand tolerability of both in immunosuppressed mouse model.

Tolerance Study (FIG. 23):

Healthy mice were divided as 3 mice/group. All the animals were treated with cyclophosphamide (150 mg/kg) on day −2 and +3 and Cortisone acetate (250 mg/kg) on day −1 and +6 to convert them neutropenic. Target dosage of compound 3 and Ambisome were given as IP for 7 days daily and the survivability was monitored for 14 days.

Objective:

Tolerance of Compound 3 and AmB dosing IP in immunocompromised model

NO INFECTION, Tolerability study only n=3 mice/group

Cyclophosphamide 150 mg/kg Days −2 and +3

Cortisone Acetate: 250 mg/kg Days −1 and +6

Respective drugs dosed IP for 7 days

Mice observed for 14 days

Survival:

Compound 3 15 mg/kg QD: 66%

Compound 3 25 mg/kg QD: 100%

Compound 3 35 mg/kg QD: 100%

Compound 3 45 mg/kg QD: 66%

AmB 25 mg/kg QD: 66%

Notes:

Clinically, 45 mg/kg Compound 3 and 25 mg/kg AmB IP showed similar signs of lethargy and ruffled fur starting D3 to D12. 25 to 35 mg/kg of Compound 3 did not affect mice's ability to eat, keep clean, nor their activity throughout the experiment, but 45 m/kg did. We can use 35 mg/kg Compound 3 dosing IP for 7 days in infection model.

We claim:

1. A compound selected from the group consisting of:

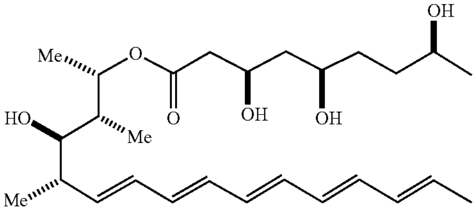

-continued

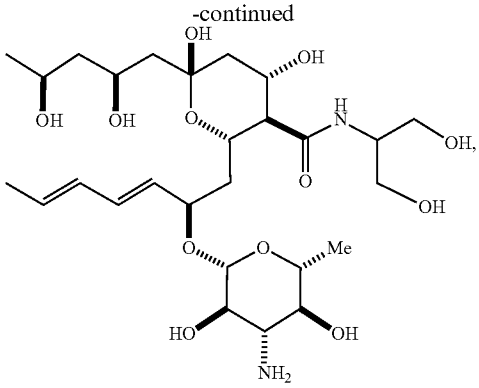

and

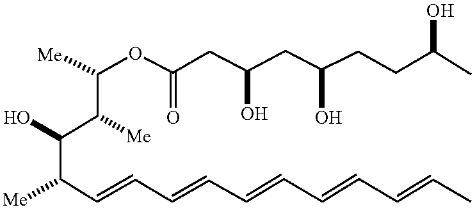

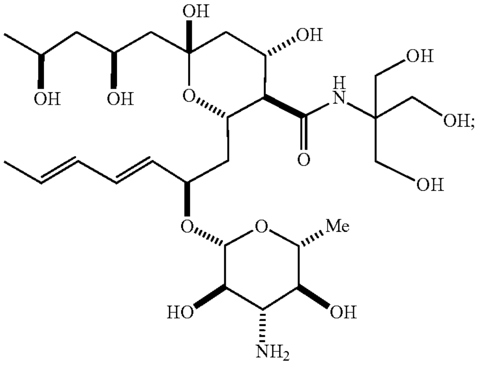

or a pharmaceutically acceptable salt thereof.

2. The compound of claim 1, wherein the compound is:

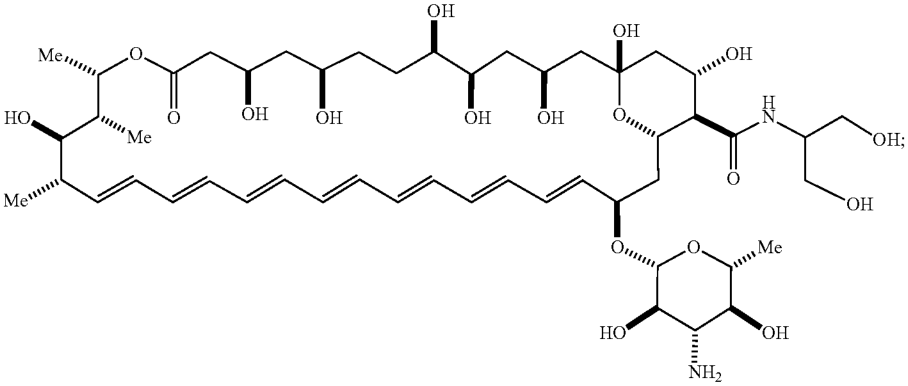

or a pharmaceutically acceptable salt thereof.

3. The compound of claim 1, wherein the compound is:
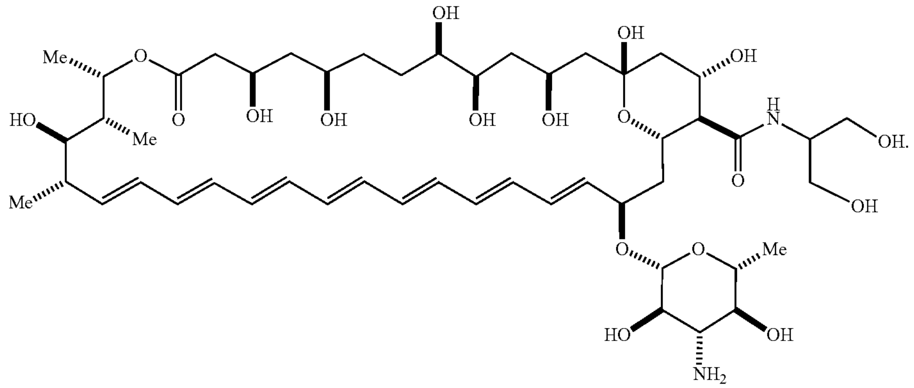
4. The compound of claim 1, wherein the compound is:
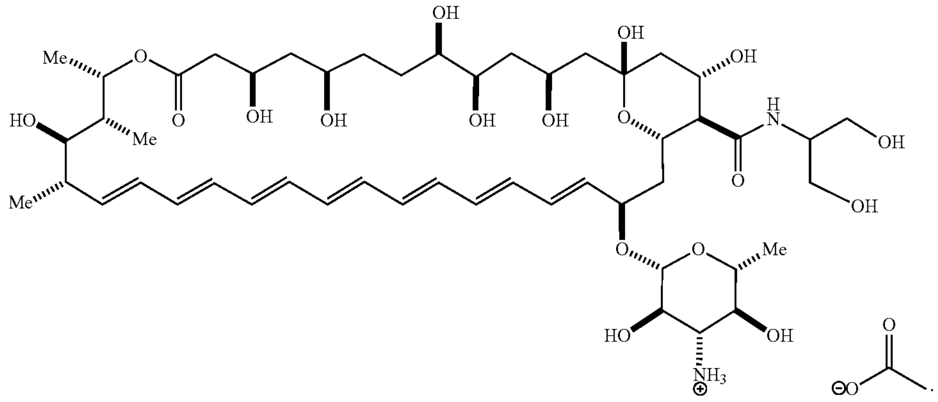
5. The compound of claim 1, wherein the compound is:
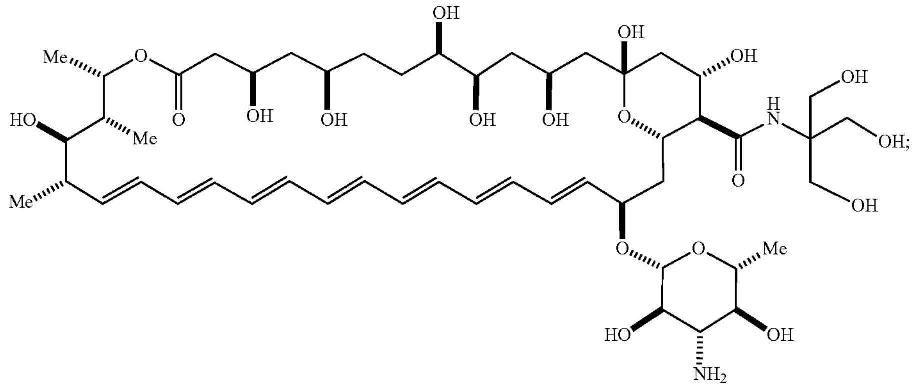
or a pharmaceutically acceptable salt thereof.

6. The compound of claim 1, wherein the compound is:

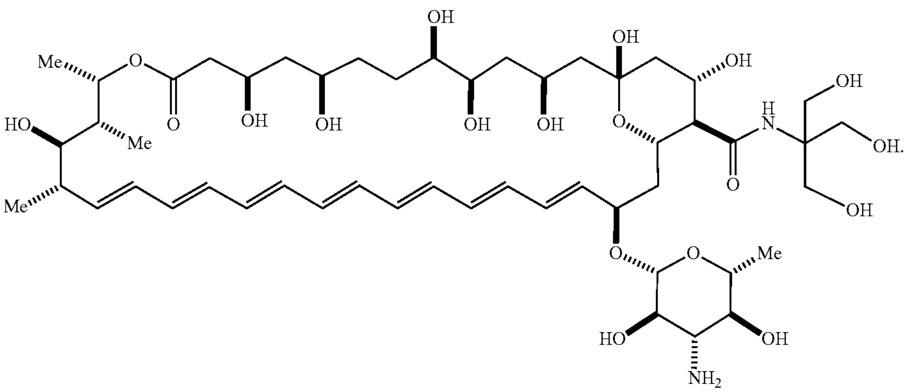

7. The compound of claim 1, wherein the compound is:

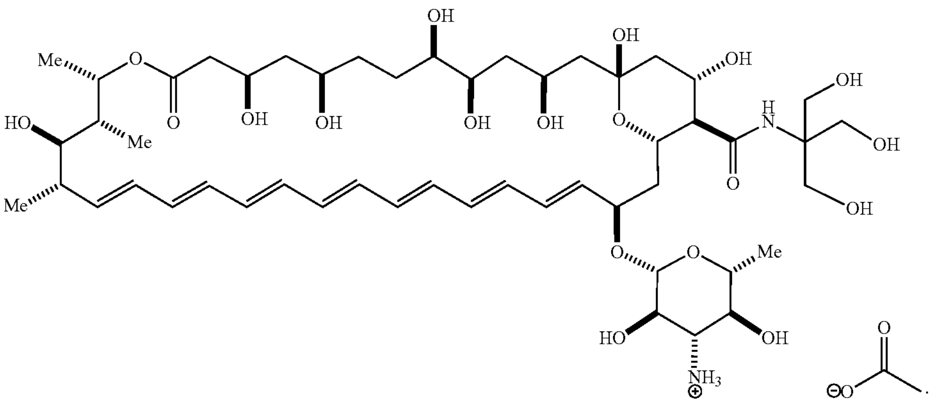

8. A pharmaceutical composition, comprising a compound of claim 1; and a pharmaceutically acceptable carrier.

9. The pharmaceutical composition of claim 8, wherein the pharmaceutical composition is an intravenous dosage form.

10. The pharmaceutical composition of claim 8, wherein the pharmaceutical composition is an oral dosage form.

11. A method of treating a fungal infection, comprising administering to a subject in need thereof a therapeutically effective amount of a compound of claim 1, thereby treating the fungal infection.

12. The method of claim 11, wherein the compound is administered intravenously.

13. The method of claim 11, wherein the compound is administered orally.

* * * * *